United States Patent
Sato et al.

(10) Patent No.: US 8,486,606 B2
(45) Date of Patent: Jul. 16, 2013

(54) ACRYLATE DERIVATIVE, HALOESTER DERIVATIVE, POLYMER COMPOUND AND PHOTORESIST COMPOSITION

(75) Inventors: Junko Sato, Niigata (JP); Osamu Nakayama, Niigata (JP); Takashi Fukumoto, Niigata (JP)

(73) Assignee: Kuraray Co., Ltd., Kurashiki-shi (JP)

( * ) Notice: Subject to any disclaimer, the term of this patent is extended or adjusted under 35 U.S.C. 154(b) by 154 days.

(21) Appl. No.: 13/001,738

(22) PCT Filed: Jun. 30, 2009

(86) PCT No.: PCT/JP2009/062016
§ 371 (c)(1),
(2), (4) Date: Dec. 28, 2010

(87) PCT Pub. No.: WO2010/001913
PCT Pub. Date: Jan. 7, 2010

(65) Prior Publication Data
US 2011/0117497 A1    May 19, 2011

(30) Foreign Application Priority Data

Jun. 30, 2008 (JP) .................. 2008-171859
Jul. 11, 2008 (JP) .................. 2008-182072

(51) Int. Cl.
*G03F 7/039* (2006.01)
*C07D 327/04* (2006.01)
*C07D 497/08* (2006.01)
*C08F 20/38* (2006.01)

(52) U.S. Cl.
USPC ........ 430/270.1; 430/910; 430/907; 430/326; 430/311; 526/257; 549/31; 549/32; 549/33; 549/40

(58) Field of Classification Search
None
See application file for complete search history.

(56) References Cited

U.S. PATENT DOCUMENTS
2005/0266351 A1  12/2005  Takemoto et al.

FOREIGN PATENT DOCUMENTS

| JP | 2005 331918 | 12/2005 |
|---|---|---|
| JP | 2007 31355 | 2/2007 |
| JP | 2007 119696 | 5/2007 |
| JP | 2008 83158 | 4/2008 |
| JP | 2008 83159 | 4/2008 |
| JP | 2008 107793 | 5/2008 |

OTHER PUBLICATIONS

Machine assisted English translation of JP2007-119696 (2007).*
International Search Report issued Aug. 4, 2009 in PCT/JP09/62016 filed Jun. 30, 2009.
U.S. Appl. No. 13/617,023, filed Sep. 14, 2012, Nakayama et al.

* cited by examiner

*Primary Examiner* — Sin J. Lee
(74) *Attorney, Agent, or Firm* — Oblon, Spivak, McClelland, Maier & Neustadt, L.L.P.

(57) ABSTRACT

An acrylate derivative represented by the following general formula (1):

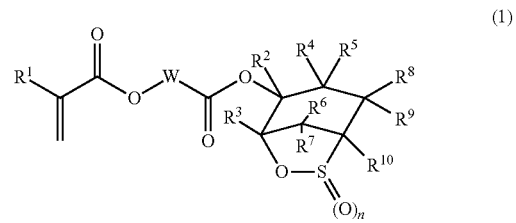

(1)

(in the formula, $R^1$ represents a hydrogen atom, a methyl group or a trifluoromethyl group; each of $R^2$, $R^3$, $R^5$, $R^7$, $R^8$, $R^9$ and $R^{10}$ independently represents a hydrogen atom, an alkyl group, a cycloalkyl group or an alkoxy group; each of $R^4$ and $R^6$ independently represents a hydrogen atom, an alkyl group, a cycloalkyl group or an alkoxy group, or $R^4$ and $R^6$ are bonded to each other to represent an alkylene group, —O— or —S—; n represents 0, 1 or 2; and W represents an alkylene group or a cycloalkylene group); an intermediate thereof; a method for producing the same; a polymer compound which is obtainable from polymerization of a raw material containing the foregoing acrylate derivative and which is excellent in solubility in an organic solvent used for the preparation of a photoresist composition; and a photoresist composition containing the polymer compound, an organic solvent and a photo acid generator and having excellent adhesion to substrate and less pattern collapse, are provided.

20 Claims, No Drawings

ACRYLATE DERIVATIVE, HALOESTER DERIVATIVE, POLYMER COMPOUND AND PHOTORESIST COMPOSITION

TECHNICAL FIELD

The present invention relates to an acrylate derivative, a haloester derivative and a method for producing the same, to a polymer compound obtainable from polymerization of a raw material containing the subject acrylate derivative and to a photoresist composition containing the subject polymer compound.

BACKGROUND ART

In recent years, in the electronic device manufacturing field represented by the integrated circuit device manufacture, demands for high integration of a device are increasing, and for that reason, a photolithography technology for the formation of a fine pattern is considered to be needed.

As techniques for microfabrication, in general, wavelength shortening of an exposure light source is carried out. Specifically, though an ultraviolet ray represented by a g-ray or an i-ray have been conventionally used, at present, the mass production of semiconductors using a KrF excimer laser or an ArF excimer layer is commenced. Also, the manufacture of semiconductors using an $F_2$ excimer laser, an electron beam, EUV (extreme ultraviolet ray), an X-ray or the like each having a shorter wavelength than such an excimer laser is studied.

A resist material is required to have lithographic characteristics such as sensitivity to such an exposure light source, resolution capable of reproducing a pattern with a fine dimension, etc. As the resist material satisfying such a requirement, chemical amplification type resists composed of an acid dissociable functional group-containing polymer compound and a compound capable of generating an acid upon irradiation with radiations (hereinafter referred to as "exposure") (the latter compound will be hereinafter referred to as "photo acid generator") are used.

This acid dissociable functional group-containing polymer compound is based on a structure in which a part of an alkali easily soluble site of an alkali soluble polymer compound is protected by an appropriate acid dissociable functional group, and the selection of such an acid dissociable functional group is very important in view of regulating a function as a photoresist composition.

For example, there are known photoresist compositions containing, as a component, a polymer compound obtaining by polymerizing a raw material containing an adamantyl group-containing acrylate as the acid dissociable functional group-containing polymer compound (see Non-Patent Document 1 and Patent Document 1); and photoresist compositions containing, as a component, a polymer compound containing an acrylate having a lactone ring or the like as a constituent unit (see Patent Document 2).

Furthermore, there are proposed photoresist compositions containing, as a component, a polymer compound containing a norbornane lactone-containing constituent unit and having high etching resistance and enhanced adhesion to substrate (see Patent Document 3). Also, there are proposed photoresist compositions containing, as a component, a polymer compound containing a constituent unit in which a connecting group is introduced, and norbornane lactone is present far from a main chain thereof (see Patent Documents 4 and 5).

PRIOR ART DOCUMENT

Patent Document

[Patent Document 1] JP-A-9-73173
[Patent Document 2] JP-A-9-90637
[Patent Document 3] JP-A-2000-26446
[Patent Document 4] JP-A-2001-188346
[Patent Document 5] JP-A-2000-31298

Non-Patent Document

[Non-Patent Document 1] *Journal of Photopolymer Science and Technology*, Vol. 9, No. 3, pages 475 to 487 (1996)

SUMMARY OF THE INVENTION

Problem That the Invention is to Solve

However, among the conventionally known (oxa)norbornane lactone-containing acrylate derivatives, there were included those involving problems such as difficulty in handling during the polymerization reaction because solubility in various solvents is low; inferior operability because polymer compounds obtainable from polymerization of the subject acrylate derivative are sparingly soluble in solvents; and the like.

Then, an object of the present invention is to provide (i) an acrylate derivative which is useful as a raw material of a polymer compound having excellent solubility in an organic solvent to be used for the preparation of a photoresist composition and an efficient production method thereof; (ii) a polymer compound obtainable from polymerization of a raw material containing the subject acrylate derivative; and (iii) a photoresist composition containing the subject polymer compound, which is less in pattern collapse.

Means for Solving the Problem

In order to solve the foregoing problems, the present inventors made extensive and intensive investigations. As a result, it has been found that an acrylate derivative having a sulfur atom in an alicyclic structure gives a polymer compound having excellent solubility in an organic solvent to be used for the preparation of a photoresist composition; and that a polymer compound obtainable from polymerization of a raw material containing the foregoing acrylate derivative gives a photoresist composition which is excellent in adhesion to substrate and less in pattern collapse.

That is, the object of the present invention is achieved by providing the following [1] to [7].

[1] A method for producing an acrylate derivative represented by the following general formula (1) [hereinafter referred to as "acrylate derivative (1)"]:

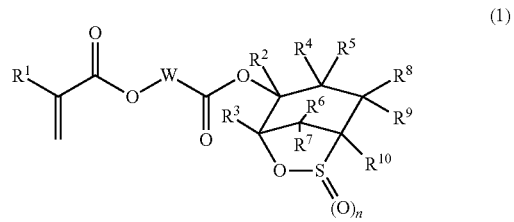

(in the formula, $R^1$ represents a hydrogen atom, a methyl group or a trifluoromethyl group; each of $R^2$, $R^3$, $R^5$, $R^7$, $R^8$, $R^9$ and $R^{10}$ independently represents a hydrogen atom, an alkyl group having from 1 to 6 carbon atoms, a cycloalkyl group having from 3 to 6 carbon atoms or an alkoxy group having from 1 to 6 carbon atoms; each of $R^4$ and $R^6$ independently represents a hydrogen atom, an alkyl group having from 1 to 6 carbon atoms, a cycloalkyl group having from 3 to 6 carbon atoms or an alkoxy group having from 1 to 6 carbon atoms, or $R^4$ and $R^6$ are bonded to each other to represent an alkylene group having from 1 to 3 carbon atoms, —O— or —S—; n represents 0, 1 or 2; and W represents an alkylene group having from 1 to 10 carbon atoms or a cycloalkylene group having from 5 to 10 carbon atoms), including steps of allowing an alcohol represented by the following general formula (2) [hereinafter referred to as "alcohol (2)"]:

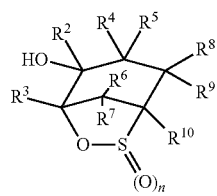

(2)

(in the formula, $R^2$, $R^3$, $R^4$, $R^5$, $R^6$, $R^7$, $R^8$, $R^9$, $R^{10}$ and n are the same as defined above) and a halocarboxylic acid halide represented by the following general formula (3) [hereinafter referred to as "halocarboxylic acid halide (3)"]:

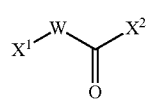

(3)

(in the formula, W is the same as defined above; and each of $X^1$ and $X^2$ independently represents a chlorine atom, a bromine atom or an iodine atom) to react with each other in the presence of a basic substance, to obtain a haloester derivative represented by the following general formula (4) [hereinafter referred to as "haloester derivative (4)"];

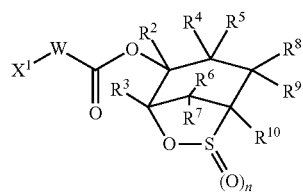

(4)

(in the formula, $R^2$, $R^3$, $R^4$, $R^5$, $R^6$, $R^7$, $R^8$, $R^9$, $R^{10}$, n, W and $X^1$ are the same as defined above); and allowing the obtained haloester derivative (4) to react with an acrylic acid based compound represented by the following general formula (5) [hereinafter referred to as "acrylic acid based compound (5)"]:

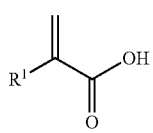

(5)

(in the formula, $R^1$ is the same as defined above) in the presence of a basic substance.

[2] A method for producing an acrylate derivative (1) including a step of allowing a haloester derivative (4) to react with an acrylic acid based compound (5) in the presence of a basic substance.

[3] A method for producing a haloester derivative (4) including a step of allowing an alcohol (2) and a halocarboxylic acid halide (3) to react with each other in the presence of a basic substance.

[4] An acrylate derivative (1).

[5] A haloester derivative (4).

[6] A polymer compound [hereinafter referred to as "polymer compound (A)"] obtainable from polymerization of a raw material containing the acrylate derivative (1) as set forth above in [4].

[7] A photoresist composition containing the polymer compound (A) as set forth above in [6], an organic solvent and a photo acid generator.

Advantage of the Invention

According to the present invention, it is possible to provide (i) an acrylate derivative which is useful as a raw material of a polymer compound having excellent solubility in an organic solvent to be used for the preparation of a photoresist composition and an efficient production method thereof; (ii) a polymer compound obtainable from polymerization of a raw material containing the subject acrylate derivative; and (iii) a photoresist composition containing the subject polymer compound and having excellent adhesion to substrate and less pattern collapse.

MODE FOR CARRYING OUT THE INVENTION

Acrylate Derivative (1)

In the acrylate derivative (1) of the present invention, $R^1$ represents a hydrogen atom, a methyl group or a trifluoromethyl group. $R^1$ is preferably a hydrogen atom or a methyl group.

In the acrylate derivative (1) of the present invention, each of $R^2$, $R^3$, $R^5$, $R^7$, $R^8$, $R^9$ and $R^{10}$ independently represents a hydrogen atom, an alkyl group having from 1 to 6 carbon atoms, a cycloalkyl group having from 3 to 6 carbon atoms or an alkoxy group having from 1 to 6 carbon atoms.

Also, in the acrylate derivative (1) of the present invention, each of $R^4$ and $R^6$ independently represents a hydrogen atom, an alkyl group having from 1 to 6 carbon atoms, a cycloalkyl group having from 3 to 6 carbon atoms or an alkoxy group having from 1 to 6 carbon atoms, or $R^4$ and $R^6$ are bonded to each other to represent an alkylene group having from 1 to 3 carbon atoms, —O— or —S—.

The alkyl group having from 1 to 6 carbon atoms which each of $R^2$, $R^3$, $R^4$, $R^5$, $R^6$, $R^7$, $R^8$, $R^9$ and $R^{10}$ independently represents may be straight chain or branched chain, and examples thereof include a methyl group, an ethyl group, a n-propyl group, an isopropyl group, a n-butyl group, an isobutyl group, a sec-butyl group, a n-pentyl group, a n-hexyl group and so forth. Of these, an alkyl group having from 1 to 3 carbon atoms is preferable.

Examples of the cycloalkyl group having from 3 to 6 carbon atoms which each of $R^2$, $R^3$, $R^4$, $R^5$, $R^6$, $R^7$, $R^8$, $R^9$ and $R^{10}$ independently represents include a cyclopropyl group, a cyclobutyl group, a cyclopentyl group and a cyclohexyl group.

The alkoxy group having from 1 to 6 carbon atoms which each of $R^2$, $R^3$, $R^4$, $R^5$, $R^6$, $R^7$, $R^8$, $R^9$ and $R^{10}$ independently represents may be straight chain or branched chain, and examples thereof include a methoxy group, an ethoxy group, a propoxy group, an isopropoxy group, a n-butoxy group, an isobutoxy group, a tert-butoxy group, a n-pentyloxy group, a n-hexyloxy group and so forth. Of these, an alkoxy group having from 1 to 3 carbon atoms is preferable.

Examples of the alkylene group having from 1 to 3 carbon atoms which $R^4$ and $R^6$ are bonded to each other to form include a methylene group, an ethane-1,1-diyl group, an ethane-1,2-diyl group, a propane-1,1-diyl group, a propane-1,2-diyl group, a propane-1,3-diyl group and a propane-2,2-diyl group. Of these, a methyl group or an ethane-1,2-diyl group is preferable, and a methylene group is more preferable.

In the acrylate derivative (1), n is 0, 1 or 2, and preferably 2.

In the acrylate derivative (1), W represents an alkylene group having from 1 to 10 carbon atoms or a cycloalkylene group having from 5 to 10 carbon atoms.

The alkylene having from 1 to 10 carbon atoms which W represents may be straight chain or branched chain, and examples thereof include a methylene group, an ethane-1,1-diyl group, an ethane-1,2-diyl group, a propane-1,1-diyl group, a propane-1,2-diyl group, a propane-1,3-diyl group, a propane-2,2-diyl group, a pentane-1,5-diyl group, a hexane-1,6-diyl group and so forth. Of these, a methylene group, an ethane-1,1-diyl group or an ethane-1,2-diyl group is preferable.

Also, examples of the cycloalkylene group having from 1 to 10 carbon atoms which W represents include a cyclohexane-1,4-diyl group and so forth.

In this connection, $R^1$, $R^2$, $R^3$, $R^4$, $R^5$, $R^6$, $R^7$, $R^8$, $R^9$, $R^{10}$, n and W shown in the alcohol (2), the halocarboxylic acid halide (3), the haloester derivative (4) and the acrylic acid based compound (5) as described later are the same as $R^1$, $R^2$, $R^3$, $R^4$, $R^5$, $R^6$, $R^7$, $R^8$, $R^9$, $R^{10}$, n and W in the acrylate derivative (1), respectively.

Specific examples of the acrylate derivative (1) are shown below, but the acrylate derivative (1) is not particularly limited thereto.

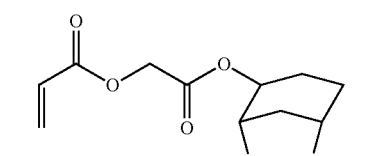

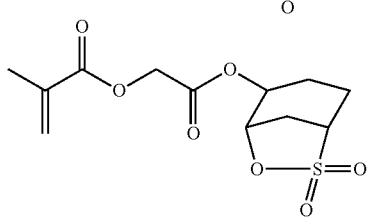

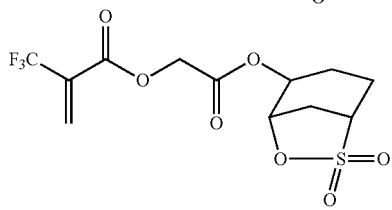

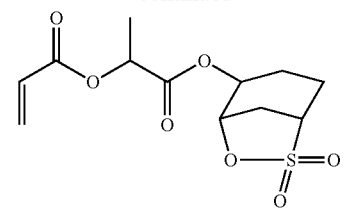

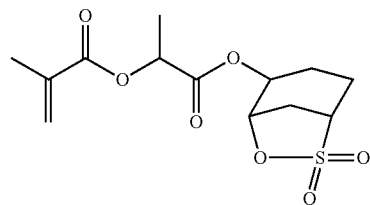

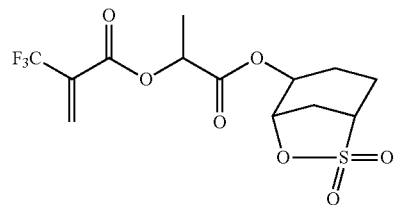

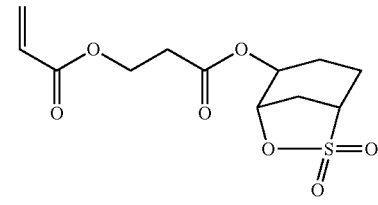

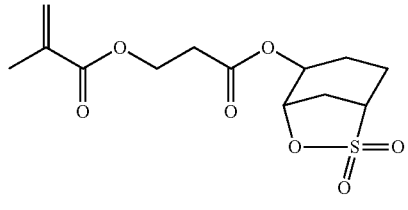

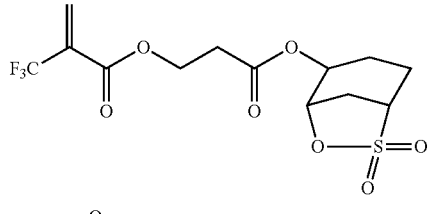

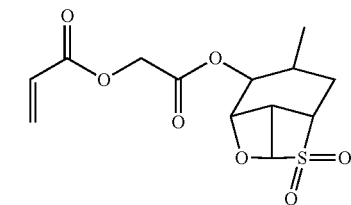

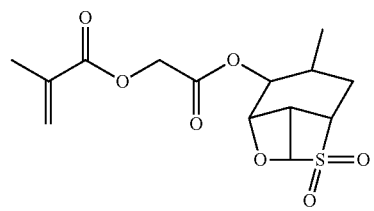

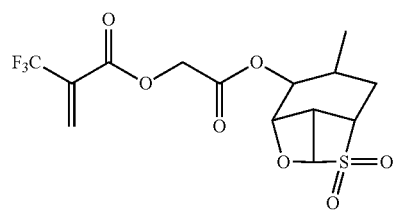
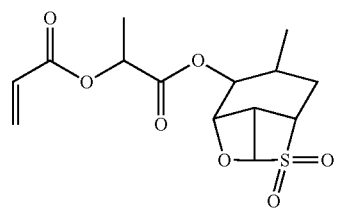
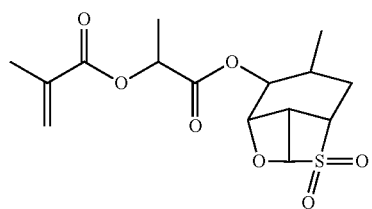
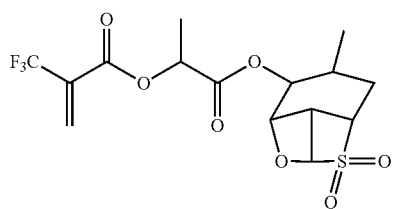
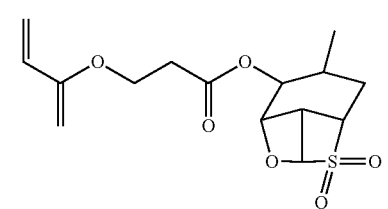
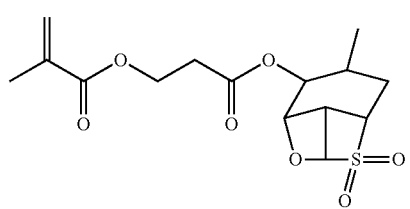
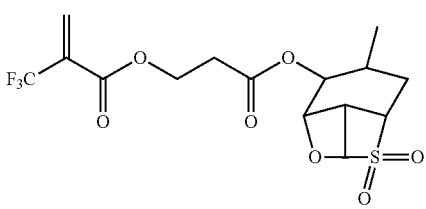
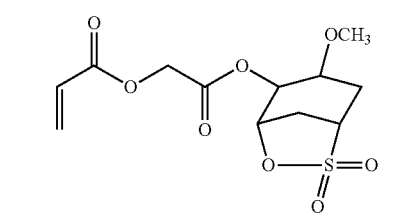
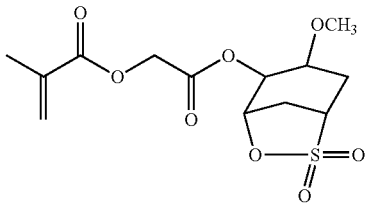
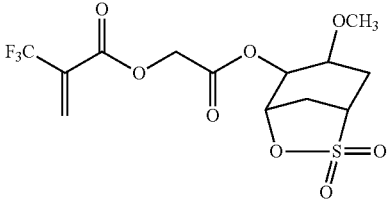
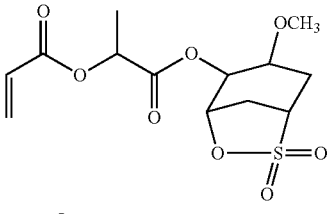
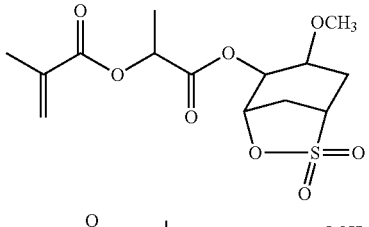
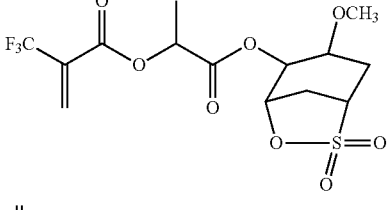
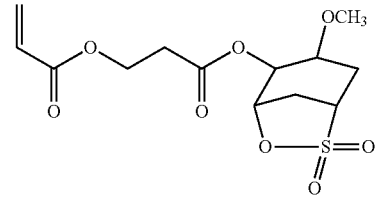
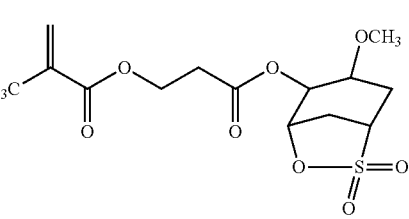

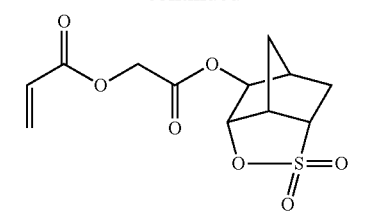
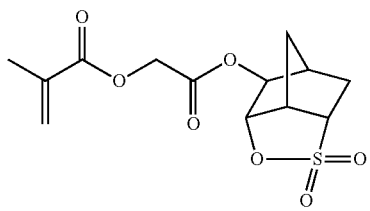
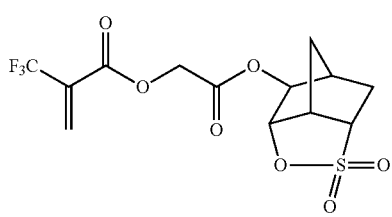
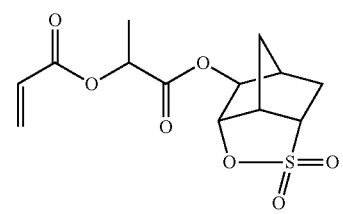
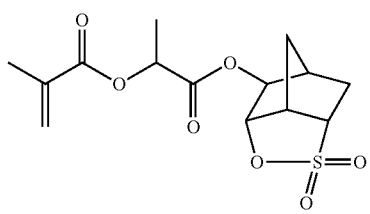
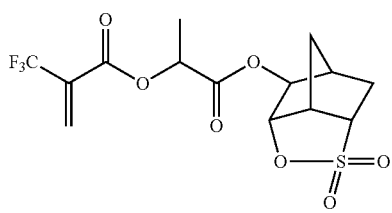
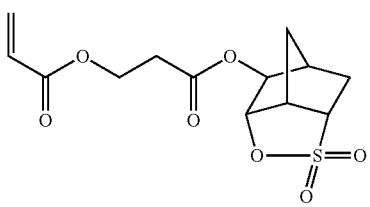
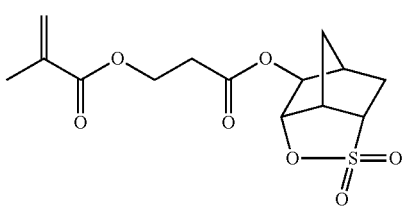
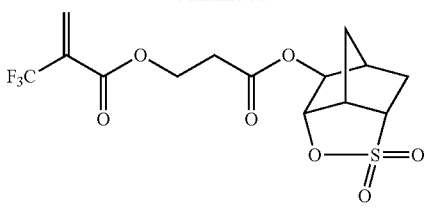
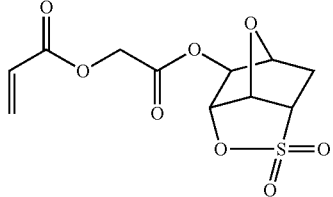
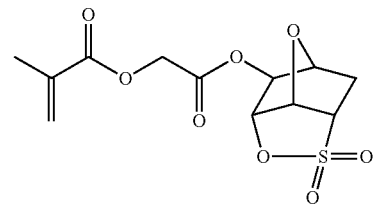
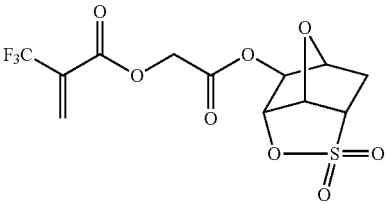
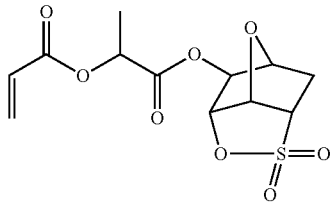
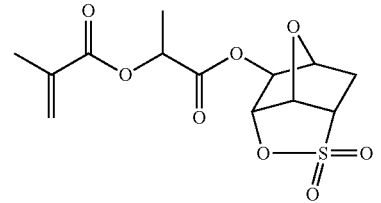
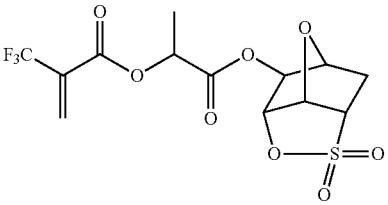
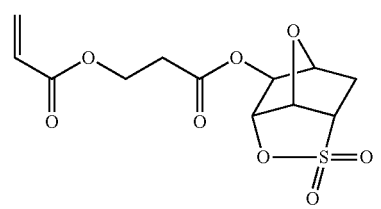

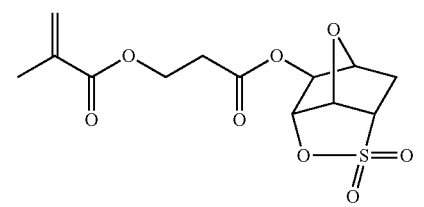
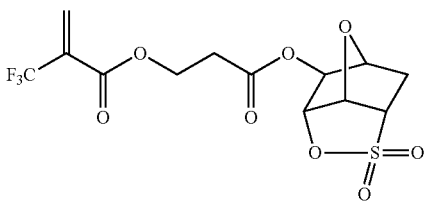
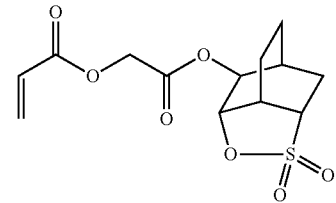
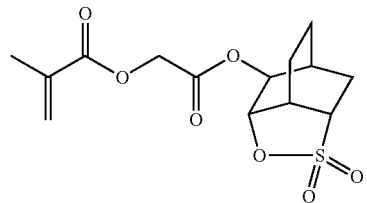
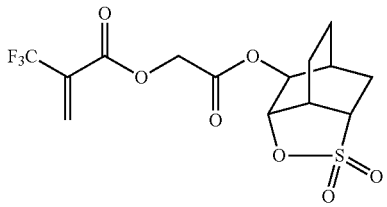
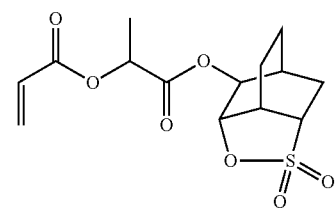
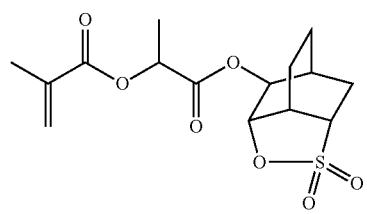
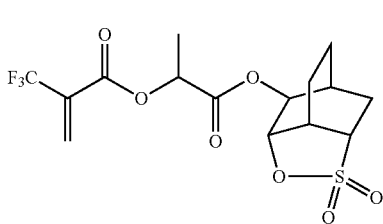

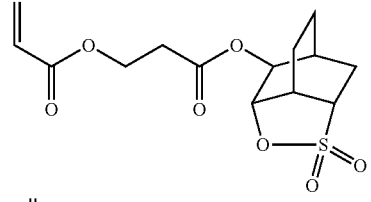
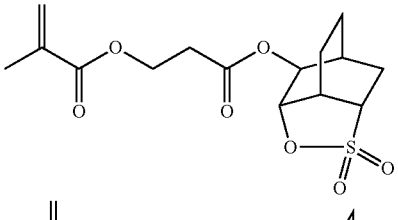
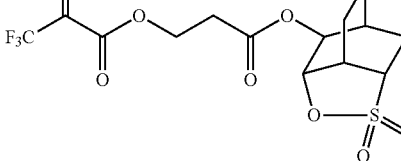

From the viewpoint of obtaining a polymer compound having excellent solubility in an organic solvent to be used for the preparation of a photoresist composition and the viewpoint of obtaining a photoresist composition having excellent adhesion to substrate and less pattern collapse, the acrylate derivative (1) is preferably one in which $R^1$ is a hydrogen atom or a methyl group; W is a methylene group or an ethane-1,1-diyl group; n is 2; all of $R^2$, $R^3$, $R^5$, $R^7$, $R^8$, $R^9$ and $R^{10}$ are a hydrogen atom; and $R^4$ and $R^6$ are bonded to each other to form a methylene group or —O—.

[Production Method of Acrylate Derivative (1)]

Though the production method of the acrylate derivative (1) of the present invention is not particularly limited, for example, the acrylate derivative (1) can be produced by allowing the alcohol (2) to react with a connection group introducing agent represented by the halocarboxylic acid halide (3) to obtain the haloester derivative (4) [hereinafter referred to as "first step"]; and allowing the haloester derivative (4) to react with the acrylic acid based compound (5) in the presence of a basic substance [hereinafter referred to as "second step"].

The first step regarding the production method of the haloester derivative (4) is hereunder described.

Examples of the foregoing connecting group introducing agent which is used in the first step include, in addition to the halocarboxylic acid halide (3), compounds represented by a formula of $(X^1$—W—$CO)_2O$, a formula of $X^1$—W—$COOC(=O)R^{11}$, or a formula of $X^1$—W—$COOSO_2R^{12}$.

In the foregoing formulae, $X^1$ represents a chlorine atom, a bromine atom or an iodine atom, and preferably a chlorine atom or a bromine atom. W is the same as defined above. $R^{11}$ represents a t-butyl group or a 2,4,6-trichlorophenyl group; and $R^{12}$ represents a methyl group or a p-tolyl group. Also, $X^2$ shown in the foregoing general formula (3) representing the halocarboxylic acid halide (3) represents a chlorine atom, a bromine atom or an iodine atom, and preferably a chlorine atom or a bromine atom.

Of these connecting group introducing agents, specific examples of the halocarboxylic acid halide (3) include chloroacetic acid chloride, bromoacetic acid bromide, 3-chloropropionic acid chloride, 3-bromopropionic acid chloride, 4-chlorobutyric acid chloride, 4-bromobutyric acid chloride, 5-chlorovaleric acid chloride, 2-chloropropionic acid chloride, 2-bromopropionic acid chloride, 2-bromopropionic acid bromide, 2-bromoisobutyric acid bromide, 3-chloropivalic acid chloride and so forth.

Examples of the compound represented by the formula of $(X^1-W-CO)_2O$ include chloroacetic anhydride, 2-chloropropionic anhydride and so forth.

Examples of the compound represented by the formula of $X^1-W-COOC(=O)R^{11}$ include chloroacetic acid pivalic anhydride, chloroacetic acid 2,4,6-trichlorobenzoic anhydride, 2-chloropropionic acid pivalic anhydride, 2-chloropropionic acid 2,4,6-trichlorobenzoic anhydride and so forth.

Examples of the compound represented by the formula of $X^1-W-COOSO_2R^{12}$ include chloroacetic acid methanesulfonic anhydride, chloroacetic acid p-toluenesulfonic anhydride, 2-chloropropionic acid methanesulfonic anhydride, 2-chloropropionic acid p-toluenesulfonic anhydride and so forth.

Of the foregoing, the halocarboxylic acid halide (3) is preferable as the connecting group introducing agent.

A use amount of the connecting group introducing agent is preferably in the range of from 0.5 to 5.0 moles per mole of the alcohol (2); and from the viewpoints of economy and easiness of post-treatment, it is more preferably in the range of from 0.8 to 3.0 moles.

Examples of the basic substance which is used in the first step include alkali metal hydrides such as sodium hydride, potassium hydride, etc.; alkaline earth metal hydrides such as magnesium hydride, calcium hydride, etc.; alkali metal hydroxides such as sodium hydroxide, potassium hydroxide, etc.; alkaline earth metal hydroxides such as magnesium hydroxide, calcium hydroxide, etc.; alkali metal carbonates such as sodium carbonate, potassium carbonate, etc.; alkaline earth metal carbonates such as magnesium carbonate, calcium carbonate, etc.; alkali metal hydrogencarbonates such as sodium hydrogencarbonate, potassium hydrogencarbonate, etc.; tertiary amines such as triethylamine, tributylamine, diisopropylethylamine, 1,4-diazabicyclo[2.2.2]octane, etc.; nitrogen-containing heterocyclic aromatic compounds such as pyridine, 2-picolin, 2,6-lutidine, 4-dimethylaminopyridine, etc.; and so forth. Of these, the nitrogen-containing heterocyclic aromatic compounds are preferable, and pyridine is more preferable.

A use amount of the basic substance is preferably in the range of from 0.5 to 5 moles per mole of the alcohol (2); and from the viewpoints of economy and easiness of post-treatment, it is more preferably in the range of from 0.8 to 3 moles.

The first step can be carried out in the presence or absence of a solvent. The solvent is not particularly limited so far as it does not hinder the reaction, and examples thereof include aliphatic hydrocarbons such as hexane, heptane, octane, etc.; aromatic hydrocarbons such as benzene, toluene, xylene, mesitylene, etc.; halogenated aromatic hydrocarbons such as chlorobenzene, fluorobenzene, etc.; ethers such as diethyl ether, diisopropyl ether, dibutyl ether, tetrahydrofuran, dioxane, 1,2-dimethoxyethane, diglyme, triglyme, tetraglyme, etc.; halogenated aliphatic hydrocarbons such as dichloromethane, chloroform, 1,2-dichloroethane, etc.; nitriles such as acetonitrile, etc.; and so forth. These may be used singly or in combinations of two or more kinds thereof.

In the case of carrying out the first step in the presence of a solvent, from the viewpoint of reducing the amount of waste solvent while keeping a reaction rate at a certain value or more, a use amount of the solvent is preferably not more than 100 parts by mass, more preferably not more than 50 parts by mass, and further preferably not more than 10 parts by mass per part by mass of the alcohol (2).

Though a reaction temperature of the first step varies depending upon the kind of the used alcohol (2), connecting group introducing agent or basic substance, in general, it is preferably in the range of from −50 to 200° C., and more preferably in the range of from −30 to 100° C.

The reaction of the first step can be terminated by the addition of water or an alcohol.

Examples of the alcohol include methanol, ethanol, n-propanol, isopropanol and so forth. It is also possible to use a mixture of water or an alcohol.

As to a use amount of water or the alcohol, water or the alcohol is preferably used in an amount of 1.0 molar time or more relative to the excessive connecting group introducing agent relative to the alcohol (2). So far as the use amount falls within this range, the excessive connecting group introducing agent relative to the alcohol (2) can be completely decomposed, so that the formation of a by-product can be suppressed.

Though a reaction pressure of the first step is not particularly limited, it is simple and easy that the reaction is carried out at atmospheric pressure, and such is preferable.

Though a reaction time of the first step varies depending upon the kind of the used alcohol (2), connecting group introducing agent or basic substance and the reaction temperature, in general, it is preferably in the range of from 0.5 hours to 48 hours, and more preferably in the range of from 1 hour to 24 hours.

A reaction operation method in the first step is not particularly limited. Also, charging method and order of the respective reagents are not particularly limited, and the reagents can be added in arbitrary method and order.

As a specific reaction operation method, for example, a method in which the alcohol (2) and the basic substance and optionally, the solvent are charged into a batchwise reactor, and the connecting group introducing agent is added to this mixed solution at a desired reaction temperature under a desired reaction pressure is preferable.

Separation and purification of the haloester derivative (4) from the reaction mixture obtained by the foregoing method can be carried out by a method which is generally adopted for separation and purification of an organic compound.

For example, after completion of the reaction, water is added to the reaction mixture, the mixture is then extracted with an organic solvent, and the obtained organic phase is concentrated, so that the haloester derivative (4) can be separated. Then, if desired, the purification is carried out by means of recrystallization, distillation, silica gel chromatography or the like, so that the haloester derivative (4) with a high purity can be obtained. In this connection, the haloester derivative (4) obtained in the first step can also be used as it is for the next step (the second step as described later) without being separated or purified from the reaction mixed solution.

Specific examples of the haloester derivative (4) obtained in the first step are shown below, but the haloester derivative (4) is not particularly limited thereto.

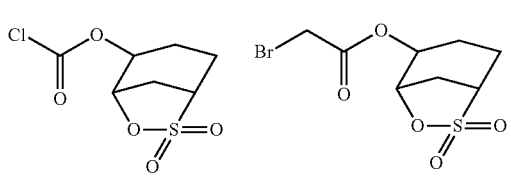

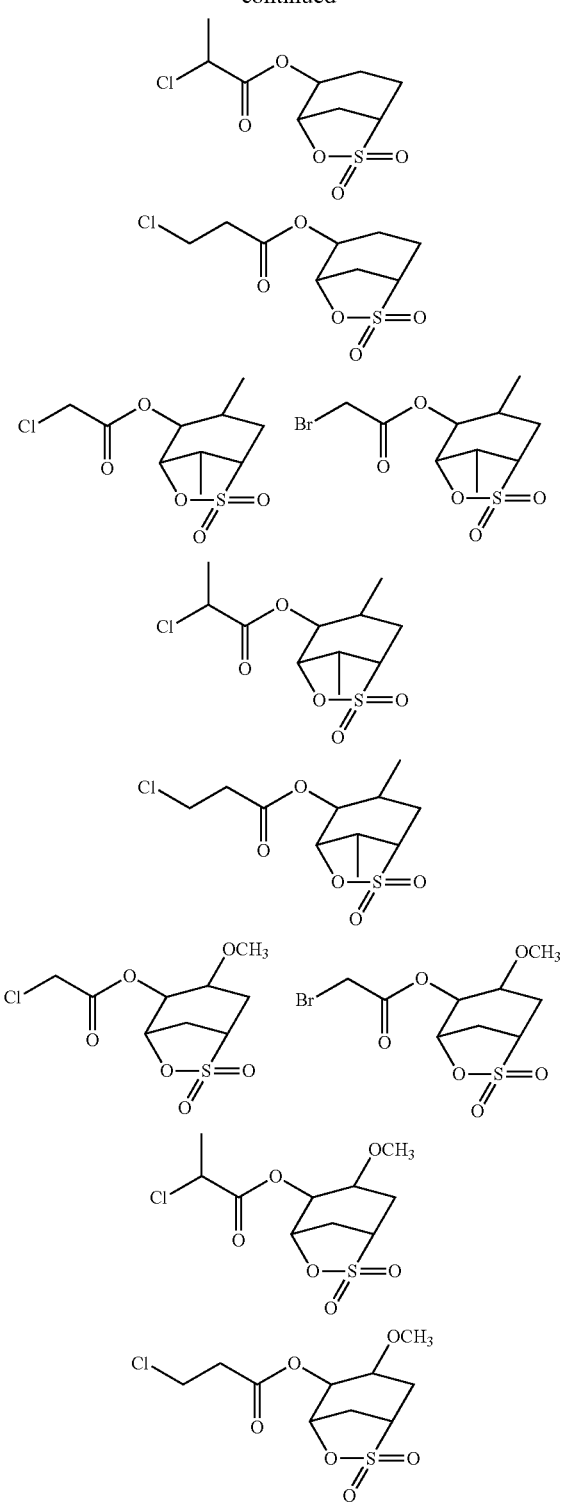

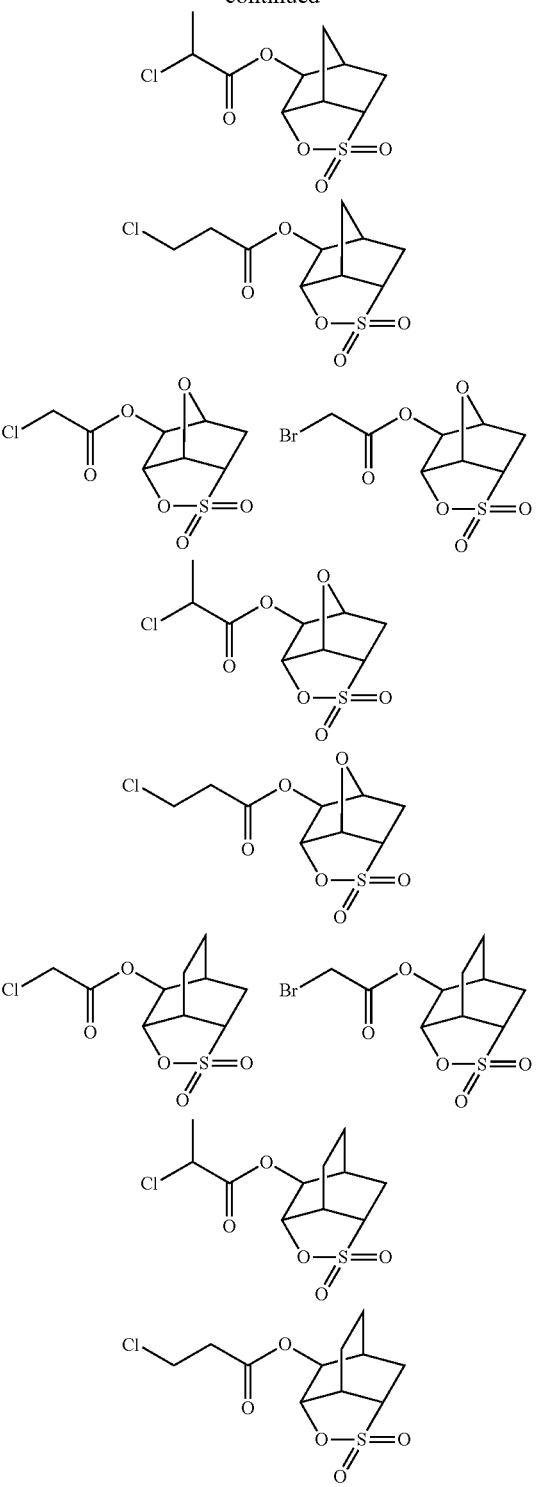

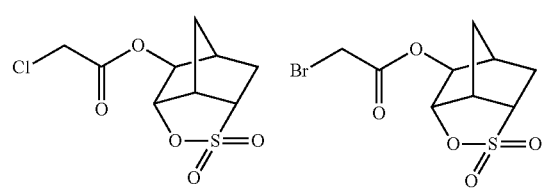

From the viewpoint of obtaining a polymer compound having excellent solubility in an organic solvent to be used for the preparation of a photoresist composition and the viewpoint of obtaining a photoresist composition having excellent adhesion to substrate and less pattern collapse, the thus obtained haloester derivative (4) is preferably one in which $X^1$ is a chlorine atom or a bromine atom; W is a methylene group or an ethane-1,1-diyl group; n is 2; all of $R^2$, $R^3$, $R^5$, $R^7$, $R^8$, $R^9$ and $R^{10}$ are a hydrogen atom; and $R^4$ and $R^6$ are bonded to each other to form a methylene group or —O—.

In this connection, though the production method of the alcohol (2) which is used as the raw material of the first step is not particularly limited, for example, the alcohol (2) can be synthesized by epoxidizing methyl norbornene sulfonate which can be synthesized from vinyl thioacetate and cyclopentadiene, with peracetic acid and subsequently allowing a perchloric acid aqueous solution to act thereon (see *Zhurnal Organicheskoi Khimii*, 1966, Vol. 2, No. 11, pages 1954 to 1961).

Next, the second step is described.

Examples of the acrylic acid based compound (5) which is used in the second step include acrylic acid, methacrylic acid and 2-(trifluoromethyl)acrylic acid.

A use amount of the acrylic acid based compound (5) is preferably in the range of from 0.8 to 10 moles, and more preferably in the range of from 1 to 5 moles per mole of the haloester derivative (4).

Examples of the basic substance which is used in the second step include the same materials as those in the basic substance which is used in the first step. Of these, alkali metal carbonates such as sodium carbonate, potassium carbonate, lithium carbonate, etc.; alkaline earth metal carbonates such as calcium carbonate, etc.; and alkali metal hydrides such as sodium hydride, etc. are preferable. Such a material can be used in a solid form or an aqueous solution form.

A use amount of the basic substance is preferably in the range of from 0.5 to 10 moles, and more preferably in the range of from 0.7 to 3 moles per mole of the haloester derivative (4).

In the second step, it is preferable to use an activator such as potassium iodide, sodium iodide, tetrabutylammonium iodide, tetrabutylammonium bromide, etc., if desired.

A use amount of the activator is preferably in the range of from 0.001 to 1 mole per mole of the haloester derivative (4); and from the viewpoints of easiness of post-treatment and economy, it is more preferably in the range of from 0.005 to 0.5 moles.

The second step can be carried out in the presence or absence of a polymerization inhibitor. The polymerization inhibitor is not particularly limited, and examples thereof include quinone based compounds such as hydroquinone, methoxyphenol, benzoquinone, toluquinone, p-tert-butyl catechol, etc.; alkylphenol based compounds such as 2,6-di-tert-butylphenol, 2,4-di-tert-butylphenol, 2-tert-butyl-4,6-dimethylphenol, etc.; amine based compounds such as phenothiazine, etc.; n-oxyl compounds such as 2,2,6,6-tetramethylpiperidin-N-oxyl, etc.; and so forth. These may be used singly or in combinations of two or more kinds thereof.

In the case of using the polymerization inhibitor, its use amount is preferably not more than 5% by mass, more preferably not more than 1% by mass, and further preferably not more than 0.5% by mass relative to the mass of the whole of the reaction mixture.

The second step can be carried out in the presence or absence of a solvent. Though the solvent is not particularly limited so far as it does not hinder the reaction, examples thereof include aliphatic hydrocarbons such as hexane, heptane, octane, etc.; aromatic hydrocarbons such as benzene, toluene, xylene, mesitylene, etc.; halogenated aromatic hydrocarbons such as chlorobenzene, fluorobenzene, etc.; ethers such as diethyl ether, diisopropyl ether, dibutyl ether, tetrahydrofuran, dioxane, 1,2-dimethoxyethane, diglyme, triglyme, tetraglyme, etc.; halogenated aliphatic hydrocarbons such as dichloromethane, chloroform, 1,2-dichloroethane, etc.; and amides such as N,N-dimethylformamide, N,N-dimethylacetamide, N-methylpyrrolidone, etc. These may be used singly or in combinations of two or more kinds thereof.

In the case of carrying out the second step in the presence of a solvent, from the viewpoint of reducing the amount of waste solvent while keeping a reaction rate at a certain value or more, a use amount of the solvent is preferably not more than 100 parts by mass, more preferably not more than 50 parts by mass, and further preferably not more than 10 parts by mass per part by mass of the haloester derivative (4).

Though a reaction temperature of the second step varies depending upon the kind of the used haloester derivative (4), acrylic acid based compound (5), basic substance or activator and the like, in general, it is preferably in the range of from −50 to 180° C., and more preferably in the range of from −30 to 130° C.

Though a reaction pressure of the second step is not particularly limited, it is simple and easy that the reaction is carried out at atmospheric pressure, and such is preferable.

Though a reaction time of the second step varies depending upon the kind of the used haloester derivative (4), acrylic acid based compound (5), basic substance or activator, the reaction temperature and the like, in general, it is preferably in the range of from 0.5 hours to 48 hours, and more preferably in the range of from 1 hour to 24 hours.

A reaction operation method in the second step is not particularly limited. Also, charging method and order of the respective reagents are not particularly limited, and the reagents can be added in arbitrary method and order.

As a specific reaction operation method, for example, a method in which the basic substance, the haloester derivative (4), the activator and the polymerization inhibitor and optionally, the solvent are charged into a batchwise reactor, and the acrylic acid based compound (5) is added to this mixed solution at a desired reaction temperature under a desired reaction pressure is preferable.

Separation and purification of the acrylate derivative (1) from the reaction mixture obtained by the second step can be carried out by a method which is generally adopted for separation and purification of an organic compound.

For example, after completion of the reaction, water is added to the reaction mixture, the mixture is then extracted with an organic solvent, and the obtained organic phase is concentrated, so that the acrylate derivative (1) can be separated. Furthermore, if desired, the purification is carried out by means of recrystallization, distillation, silica gel chromatography or the like, so that the acrylate derivative (1) with a high purity can be obtained.

Also, if desired, it is possible to reduce a content of the metal in the obtained acrylate derivative (1) by adding a chelating agent such as nitrilotriacetic acid, ethylenediaminetetraacetic acid, etc., followed by filtration or treatment with a metal removal filter, for example, ZETA PLUS (registered trademark) (a trade name, manufactured by Sumitomo 3M Limited), PROTEGO (a trade name, manufactured by Nihon Entegris K.K.), ION CLEAN (a trade name, manufactured by Nihon Pall Ltd.), etc.

[Polymer Compound (A)]

The polymer compound (A) obtainable from polymerization of a raw material containing the acrylate derivative (1) of the present invention can be used as a component of the photoresist composition.

The polymer compound (A) of the present invention is a polymer obtainable from homopolymerization of the acrylate derivative (1) as a raw material or a copolymer obtained copolymerizing the acrylate derivative (1) and other polymerizable compound as raw materials, and it may have a constituent unit on the basis of the acrylate derivative (1) [hereinafter referred to as "constituent unit (a0)"]. In general, a content proportion of the constituent unit (a0) in the subject polymer compound is preferably in the range of from 10 to 80% by mole, and more preferably in the range of from 20 to 70% by mole.

Specific examples of the constituent unit (a0) include the following constituent units (a0-1) to (a0-20), but the constituent unit (a0) is not particularly limited thereto.

(a0-1)

(a0-2)

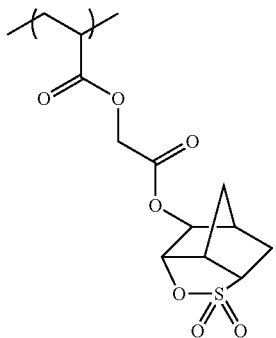

(a0-3)

(a0-4)

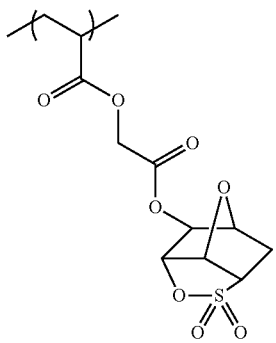

(a0-5)

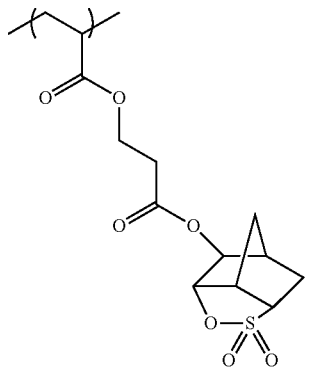

(a0-6)

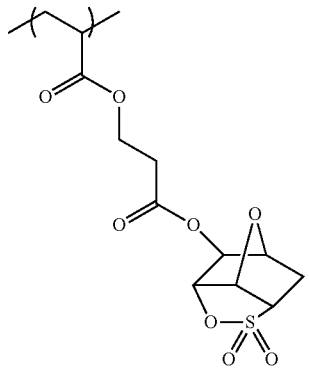

(a0-7)

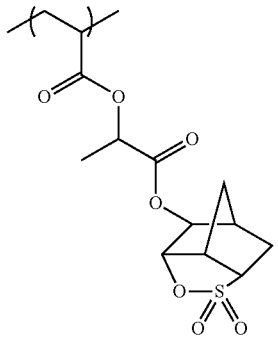

(a0-8)

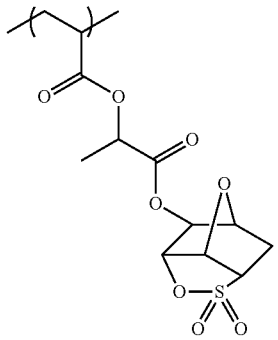

(a0-9)
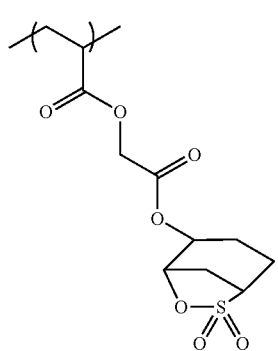
(a0-13)
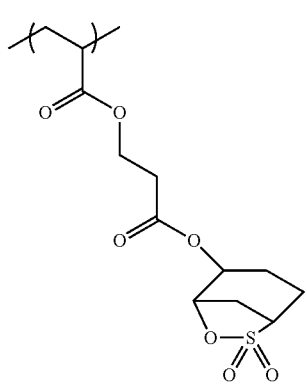
(a0-10)
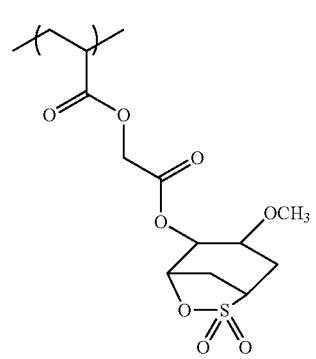
(a0-14)
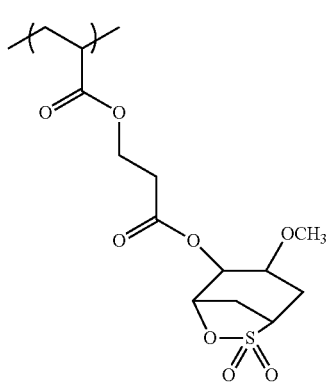
(a0-11)
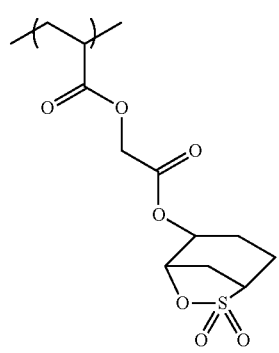
(a0-15)
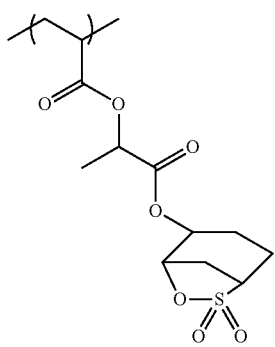
(a0-12)
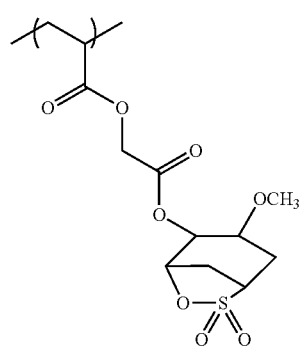
(a0-16)
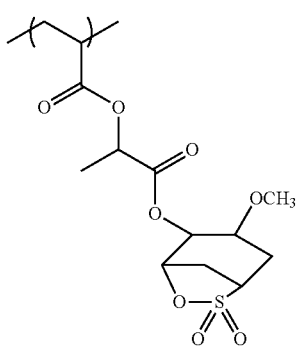

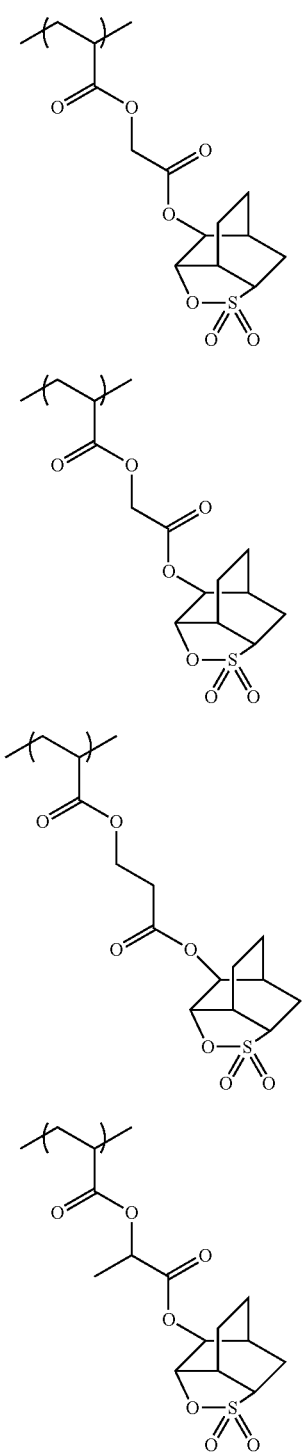

(a0-17)

(a0-18)

(a0-19)

(a0-20)

In the case where the polymer compound (A) of the present invention is a copolymer containing other constituent unit in addition to the constituent unit (a0), examples of other constituent unit include a constituent unit (a1), a constituent unit (a2), a constituent unit (a3), a constituent unit (a4) and a constituent unit (a5) as listed below.

Of these respective constituent units, the constituent unit which is combined with the constituent unit (a0) in the subject copolymer may be properly chosen among the constituent units (a1) to (a5) depending upon the application of the subject resist composition and desired characteristics.

(Constituent Unit (a1))

The constituent unit (a1) is a constituent unit (a1) derived from an acid dissociable dissolution inhibiting group-containing acrylate.

The acid dissociable dissolution inhibiting group in the constituent unit (a1) is a group in which in forming a resist pattern as a resist composition, has alkali dissolution inhibiting properties so as to make the whole of the polymer compound (A) sparingly soluble in an alkaline developer prior to dissociation and is dissociated by an acid generated from an acid generator component upon exposure, thereby increasing dissolution of the whole of this polymer compound (A) in the alkaline developer, and groups which have been proposed as an acid dissociable dissolution inhibiting group of a base resin for chemical amplification type resist so far can be used. In general, there are widely known groups capable of forming a cyclic or chain, tertiary alkyl ester together with a carboxy group in (meth)acrylic acid or the like; acetal type acid dissociable dissolution inhibiting groups such as an alkoxyalkyl group, etc.; and so forth.

The "tertiary alkyl ester" as referred to herein expresses a structure obtainable from substitution of a hydrogen atom of the carboxy group with a chain or cyclic alkyl group to form an ester, and a tertiary carbon atom of the chain or cyclic alkyl group is bonded to an oxygen atom of a terminal of its carbonyloxy group (—C(O)—O—). In this tertiary alkyl ester, when an acid acts thereon, the bond between the oxygen atom and the tertiary carbon atom is cleaved.

In this connection, the foregoing chain or cyclic alkyl group may have a substituent.

For the sake of convenience, the group which has become acid dissociable upon constituting a tertiary alkyl ester together with the carboxy group is hereinafter referred to as "tertiary alkyl ester type acid dissociable dissolution inhibiting group".

Examples of the tertiary alkyl group in the tertiary alkyl ester include aliphatic branched chain tertiary alkyl groups having from 4 to 8 carbon atoms, such as a tert-butyl group, a tert-pentyl group, a tert-heptyl group, etc.; alicyclic hydrocarbon groups such as a 2-methyl-2-adamantyl group, a 2-ethyl-2-adamantyl group, etc.; and so forth.

In general, the foregoing "acetal type acid dissociable dissolution inhibiting group" substitutes a hydrogen atom of a terminal of an alkali soluble group such as a carboxy group, a hydroxyl group, etc., thereby bonding to an oxygen atom. Then, when an acid is generated upon exposure, this acid acts, so that the bond between the acetal type acid dissociable dissolution inhibiting group and the oxygen atom to which the subject acetal type acid dissociable dissolution inhibiting group is bonded is cleaved.

Examples of the acetal type acid dissociable dissolution inhibiting group include groups represented by the following general formula (p1).

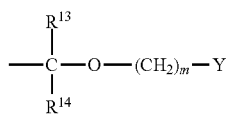

(p1)

In the foregoing formula (p1), each of $R^{13}$ and $R^{14}$ independently represents a hydrogen atom or an alkyl group having from 1 to 5 carbon atoms; m represents an integer of from 0 to 3; and Y represents an alkyl group having from 1 to 5 carbon atoms or an alicyclic hydrocarbon group having from 3 to 15 carbon atoms.

m is preferably an integer of from 0 to 2, more preferably 0 or 1, and further preferably 0.

Examples of the alkyl group having from 1 to 5 carbon atoms which each of $R^{13}$, $R^{14}$ and Y independently represents include a methyl group, an ethyl group, various propyl groups (the term "various" means that the group includes a straight chain and all branched chains; hereinafter the same), various butyl groups and so forth. Of these, a methyl group or an ethyl group is preferable, and a methyl group is more preferable. As the alicyclic hydrocarbon group having from 3 to 15 carbon atoms which Y represents, a group can be properly chosen and used among a large number of monocyclic or polycyclic alicyclic hydrocarbon groups which have hitherto been proposed in ArF resists or the like, and examples thereof include groups obtainable from subtraction of one hydrogen atom from cyclopentane, cyclohexane, cycloheptane, bornane, isobornane, norbornane, 1,3,3-trimethylbicyclo[2.2.1]heptane, adamantane or tetracyclo[3.2.0.0$^{2,7}$.0$^{4,6}$]heptane.

As the acid dissociable dissolution inhibiting group (p1), it is preferable that at least one of $R^{13}$ and $R^{14}$ is a hydrogen atom. That is, it is preferable that the acid dissociable dissolution inhibiting group (p1) is a group represented by the following general formula (p1-1).

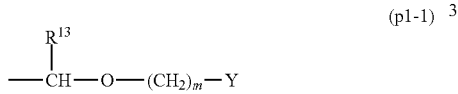

(p1-1)

In the foregoing (p1-1), $R^{13}$, m and Y are the same as those in the formula (p1), respectively.

Also, as the acetal type acid dissociable dissolution inhibiting group, a group represented by the following general formula (p2) is exemplified.

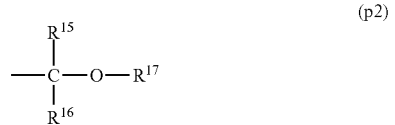

(p2)

In the foregoing formula (p2), each of $R^{15}$ and $R^{16}$ independently represents a hydrogen atom or an alkyl group having from 1 to 15 carbon atoms; and $R^{17}$ represents an alkyl group having from 1 to 15 carbon atoms or a cycloalkyl group having from 4 to 15 carbon atoms. $R^{15}$ and $R^{17}$ may be bonded to each other to form a ring.

The alkyl group having from 1 to 15 carbon atoms which each of $R^{15}$ and $R^{16}$ independently represents may be straight chain or branched chain, and examples thereof include a methyl group, an ethyl group, various propyl groups, various butyl groups, various pentyl groups, various hexyl groups, various heptyl group, various octyl groups, various decyl groups and so forth. Of these, a methyl group or an ethyl group is preferable, and a methyl group is more preferable.

In this connection, as $R^{15}$ and $R^{16}$, it is preferable that both of $R^{15}$ and $R^{16}$ are a hydrogen atom, or either one of $R^{15}$ or $R^{16}$ is a hydrogen atom, with the other being a methyl group; and it is more preferable that both of $R^{15}$ and $R^{16}$ are a hydrogen atom.

The alkyl group having from 1 to 15 carbon atoms which $R^{17}$ represents may be straight chain or branched chain, and examples thereof include the same groups as those in the alkyl group having from 1 to 15 carbon atoms which $R^{15}$ or $R^{16}$ represents. Of these, a methyl group or an ethyl group is preferable, and an ethyl group is more preferable.

Examples of the cycloalkyl group having from 4 to 15 carbon atoms (preferably from 4 to 12 carbon atoms, and more preferably from 5 to 10 carbon atoms) which $R^{17}$ represents include groups obtainable from subtraction of one hydrogen atom from a monocycloalkane or a polycycloalkane such as a bicycloalkane, a tricycloalkane, a tetracycloalkane, etc., which is substituted or not substituted with a fluorine atom or a fluorinated alkyl group; and so forth. More specifically, there are exemplified groups obtainable from subtraction of one hydrogen atom from a monocycloalkane such as cyclopentane, cyclohexane, etc., which is substituted or not substituted with a fluorine atom or a fluorinated alkyl group, or a polycycloalkane such as adamantane, norbornane, isobornane, tricyclodecane, tetracyclododecane, etc., which is substituted or not substituted with a fluorine atom or a fluorinated alkyl group; and so forth. Of these, a group obtainable from subtraction of one hydrogen atom from adamantane is preferable.

Also, $R^{15}$ and $R^{17}$ may be bonded to each other to form a ring. In that case, the ring is formed by $R^{15}$ and $R^{17}$, an oxygen atom to which $R^{17}$ is bonded and a carbon atom to which the subject oxygen atom and $R^{15}$ are bonded. The subject ring is preferably a 4- to 7-membered ring, and more preferably a 4- to 6-membered ring. Examples of the subject ring include a tetrahydropyranyl group, a tetrahydrofuranyl group and so forth.

It is preferable to use at least one member selected from the group consisting of the following constituent unit (a1-0-1) and the following constituent unit (a1-0-2) as the constituent unit (a1).

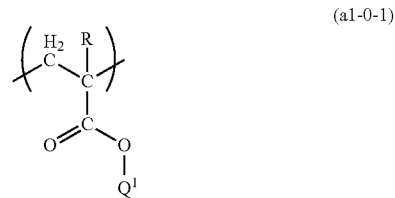

(a1-0-1)

In the foregoing constituent unit (a1-0-1), R represents a hydrogen atom or a halogenated or non-halogenated alkyl group having from 1 to 5 carbon atoms; and $Q^1$ represents an acid dissociable dissolution inhibiting group.

In the constituent unit (a1-0-1), examples of the non-halogenated alkyl group having from 1 to 5 carbon atoms which R represents include a methyl group, an ethyl group, various propyl groups, various butyl groups, various pentyl groups and so forth.

Also, examples of the halogenated alkyl group having from 1 to 5 carbon atoms which R represents include groups obtainable from substitution of a part or the whole of hydrogen atoms in the foregoing alkyl group having from 1 to 5 carbon atoms (preferably an ethyl group or a methyl group) with a halogen atom (preferably a fluorine atom).

$Q^1$ is not particularly limited so far as it is an acid dissociable dissolution inhibiting group, and examples thereof include the foregoing tertiary alkyl ester type acid dissociable dissolution inhibiting group and acetal type acid dissociable dissolution inhibiting group and so forth.

(a1-0-2)

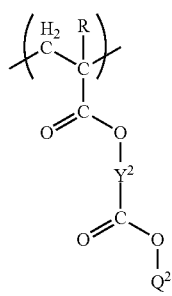

In the foregoing constituent unit (a1-0-2), R is the same as defined for R in the foregoing constituent unit (a1-0-1); $Q^2$ represents an acid dissociable dissolution inhibiting group; and $Y^2$ represents an alkylene group having from 1 to 4 carbon atoms or a divalent alicyclic hydrocarbon group having from 3 to 15 carbon atoms.

$Q^2$ is the same as defined for $Q^1$ in the constituent unit (a1-0-1).

Examples of the alkylene group having from 1 to 4 carbon atoms which $Y^2$ represents include a methylene group, an ethane-1,1-diyl group, an ethane-1,2-diyl group, a propane-1,1-diyl group, a propane-1,2-diyl group, a propane-1,3-diyl group, a butane-1,4-diyl group and so forth. Examples of the divalent alicyclic hydrocarbon group having from 3 to 15 carbon atoms which $Y^2$ represents include groups obtainable from subtraction of two hydrogen atoms from a monocycloalkane such as cyclopentane, cyclohexane, etc., or a polycycloalkane such as adamantane, norbornane, isobornane, tricyclodecane, tetracyclododecane, etc.

More specifically, there are exemplified the following constituent units (a1-1) to (a1-5) as the constituent unit (a1).

(a1-1)

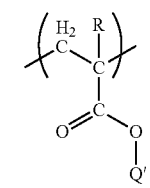

(a1-2)

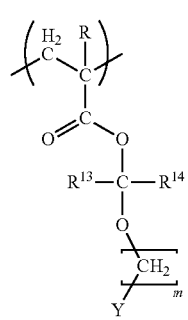

(a1-3)

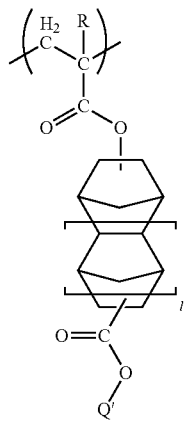

(a1-4)

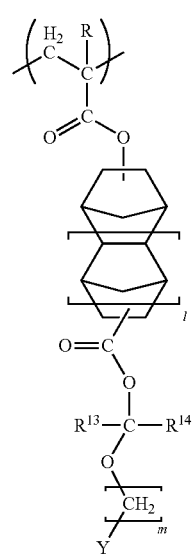

(a1-5)

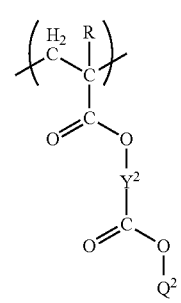

In the foregoing constituent units (a1-1) and (a1-3), Q' represents a tertiary alkyl ester type acid dissociable dissolution inhibiting group; and in the foregoing constituent units (a1-3) and (a1-4), l represents 0 or 1. Also, in the constituent units (a1-1) to (a1-5), R, Y, $Y^2$, m, R, $Q^2$, $R^{13}$ and $R^{14}$ are the same as defined for those in the foregoing general formula (p1) and constituent unit (a1-0-1), respectively.

It is preferable that at least one of $R^{13}$ and $R^{14}$ is a hydrogen atom; and it is more preferable that both of them are a hydrogen atom. m is preferably 0 or 1.

In this connection, examples of the tertiary alkyl ester type acid dissociable dissolution inhibiting group which Q' represents include the same groups as those in the tertiary alkyl ester type acid dissociable dissolution inhibiting group as described in the foregoing constituent unit (a1).

Specific examples of the foregoing constituent units (a1-1) to (a1-5) are shown below.
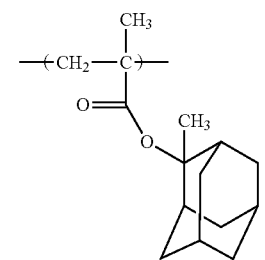 (a1-1-1)
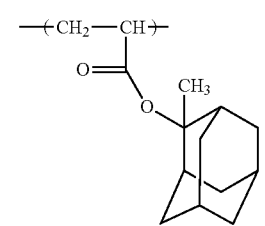 (a1-1-2)
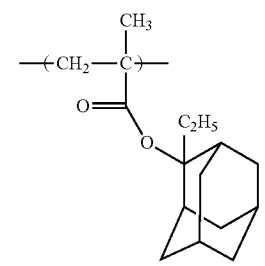 (a1-1-3)
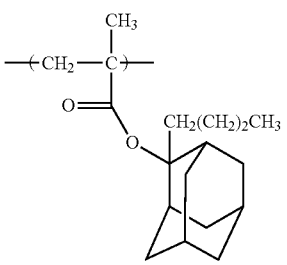 (a1-1-4)
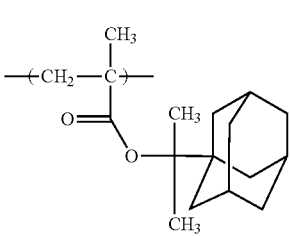 (a1-1-5)
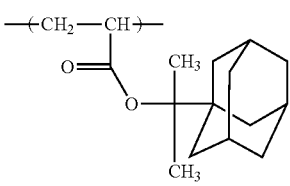 (a1-1-6)
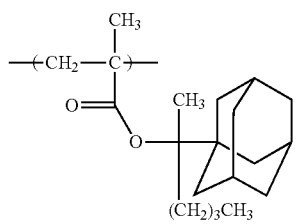 (a1-1-7)
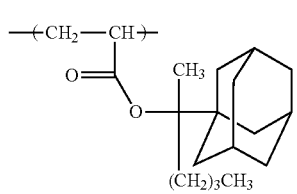 (a1-1-8)
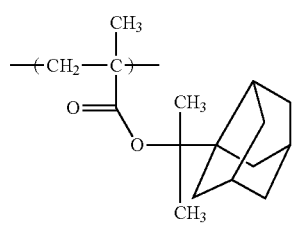 (a1-1-9)
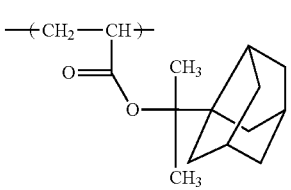 (a1-1-10)
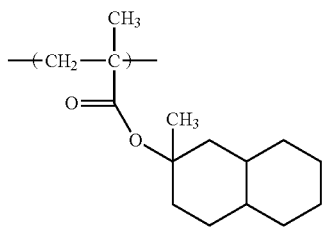 (a1-1-11)
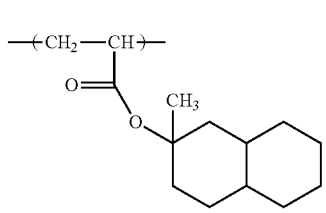 (a1-1-12)
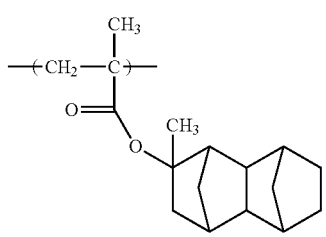 (a1-1-13)

-continued
(a1-1-14)
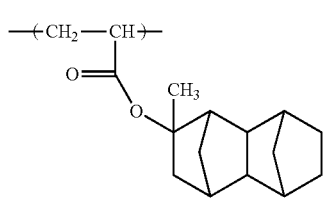
(a1-1-15)
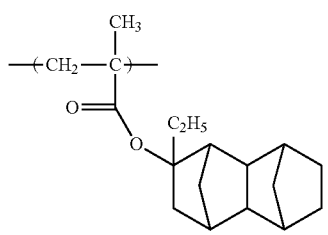
(a1-1-16)
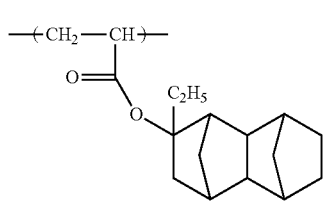
(a1-1-17)
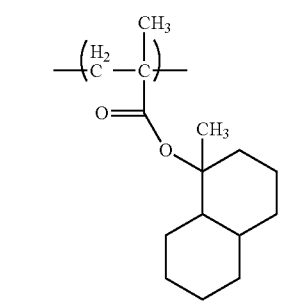
(a1-1-18)
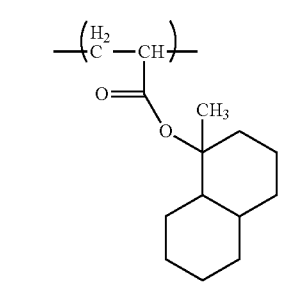
(a1-1-19)
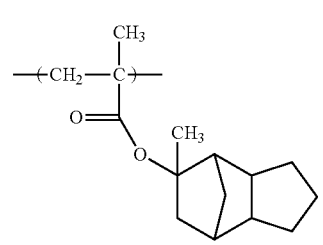
(a1-1-20)
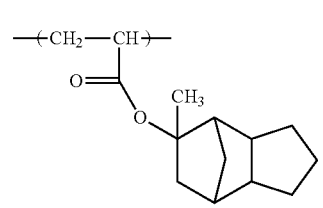
-continued
(a1-1-21)
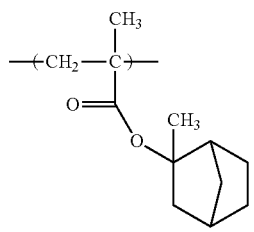
(a1-1-22)
(a1-1-23)
(a1-1-24)
(a1-1-25)
(a1-1-26)
(a1-1-27)
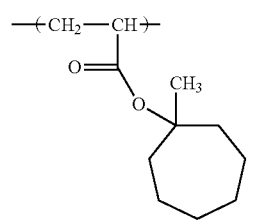

-continued
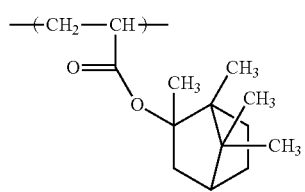
(a1-1-28)
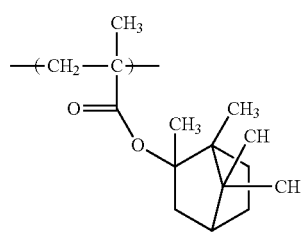
(a1-1-29)
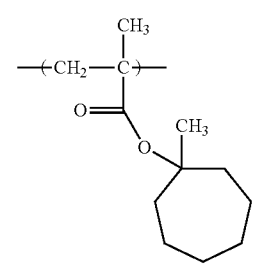
(a1-1-30)
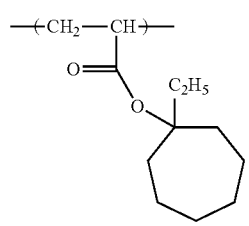
(a1-1-31)
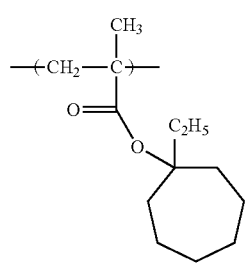
(a1-1-32)
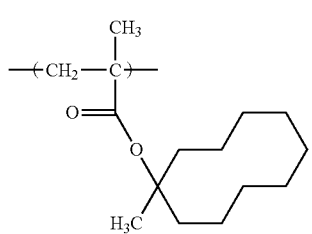
(a1-1-33)
-continued
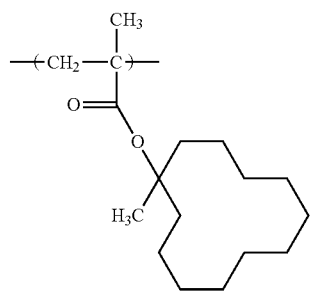
(a1-1-34)
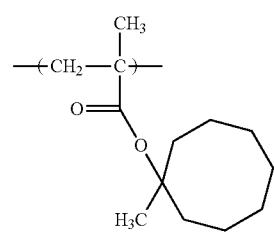
(a1-1-35)
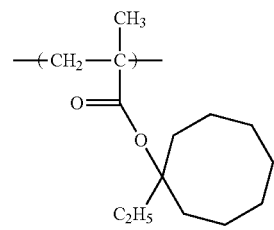
(a1-1-36)
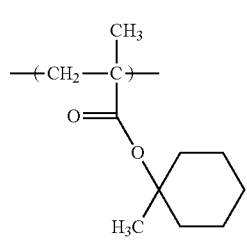
(a1-1-37)
(a1-1-38)
(a1-1-39)

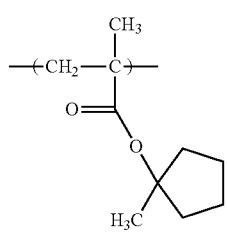 (a1-1-40)
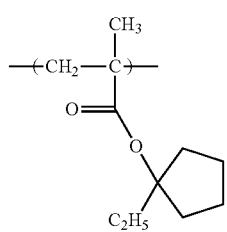 (a1-1-41)
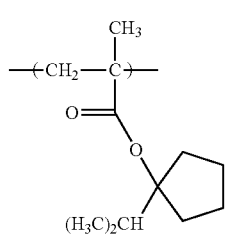 (a1-1-42)
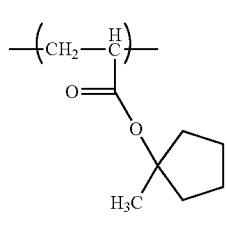 (a1-1-43)
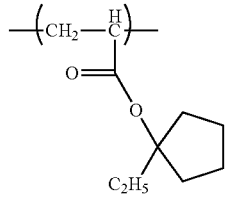 (a1-1-44)
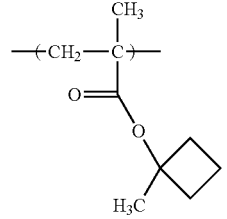 (a1-1-45)
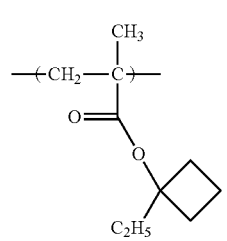 (a1-1-46)
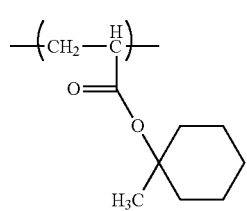 (a1-1-47)
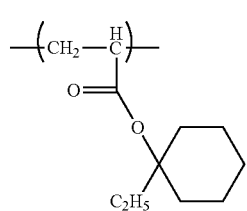 (a1-1-48)
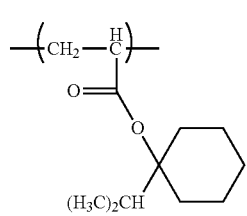 (a1-1-49)
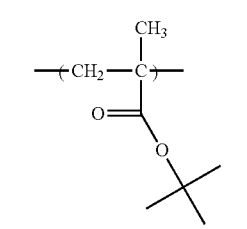 (a1-1-50)
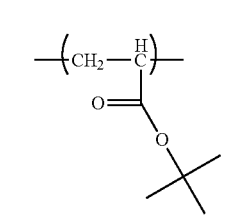 (a1-1-51)
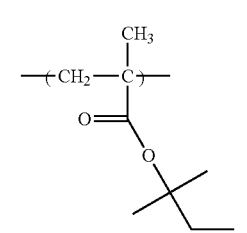 (a1-1-52)
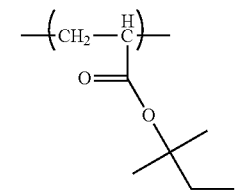 (a1-1-53)

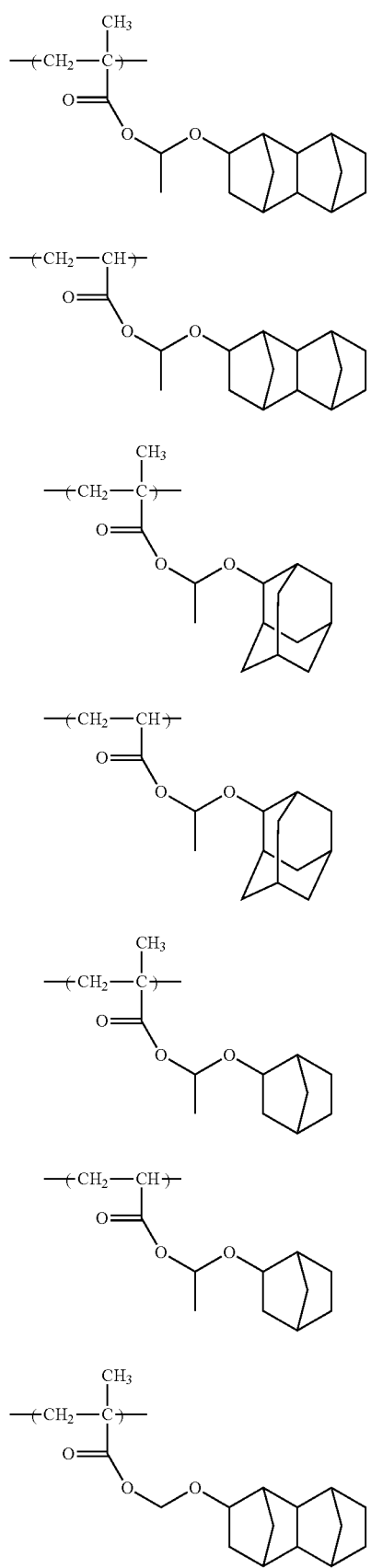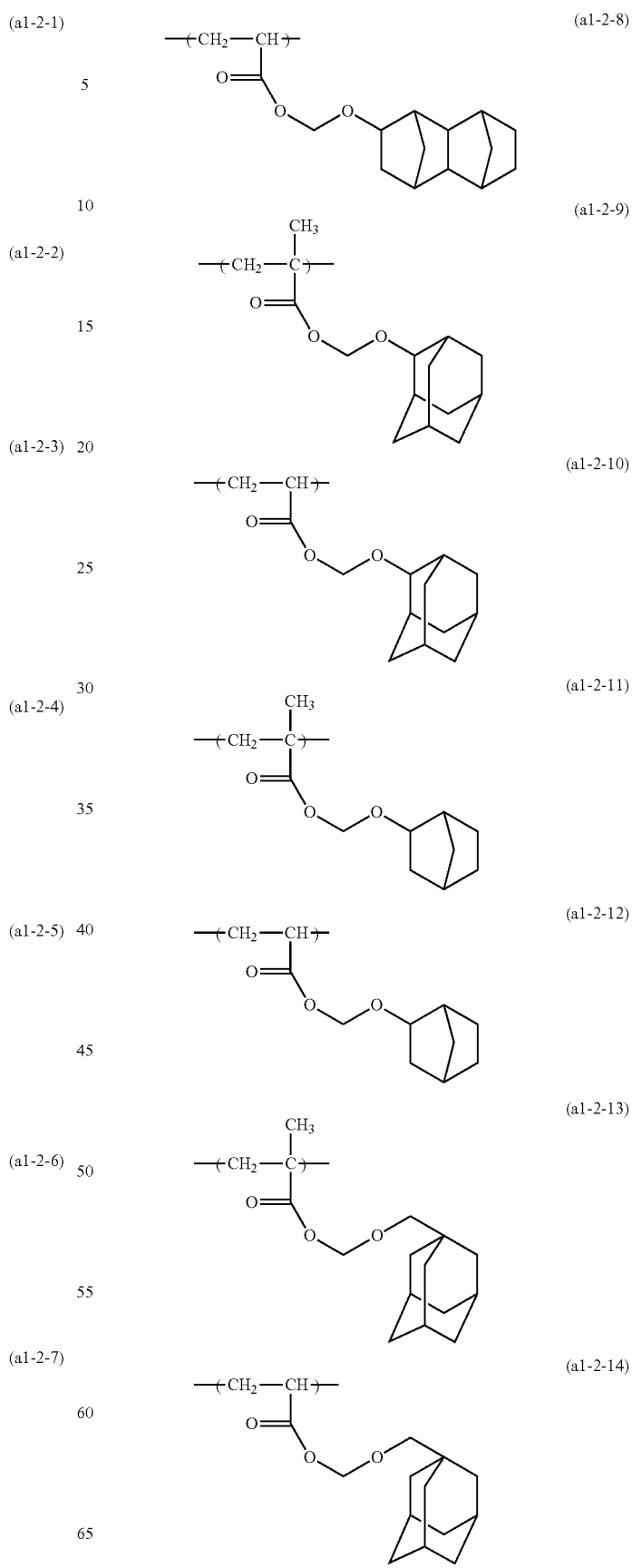

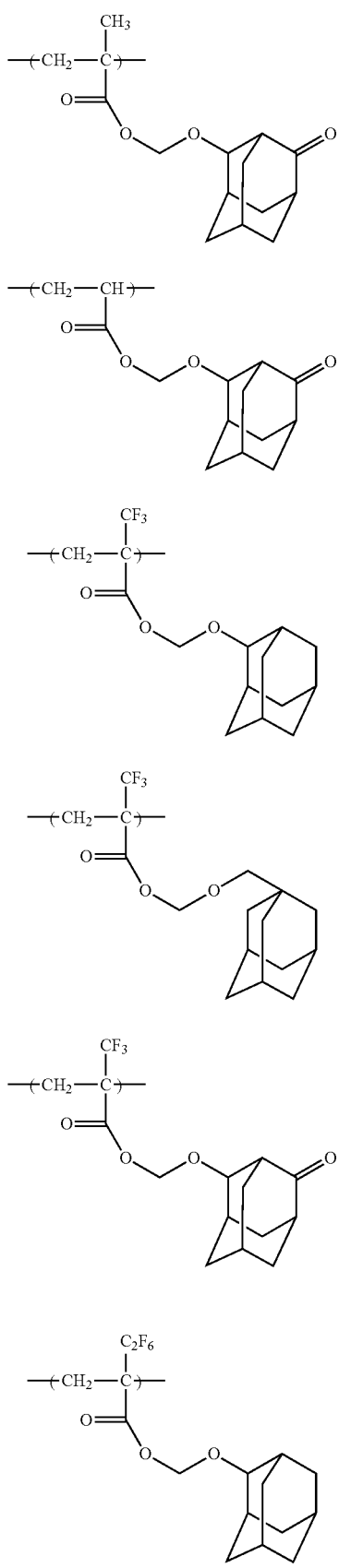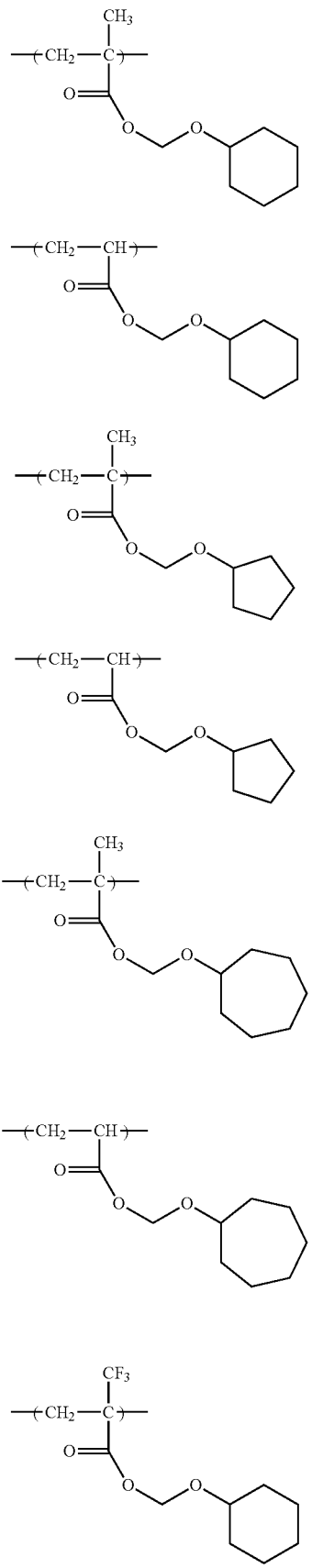

-continued
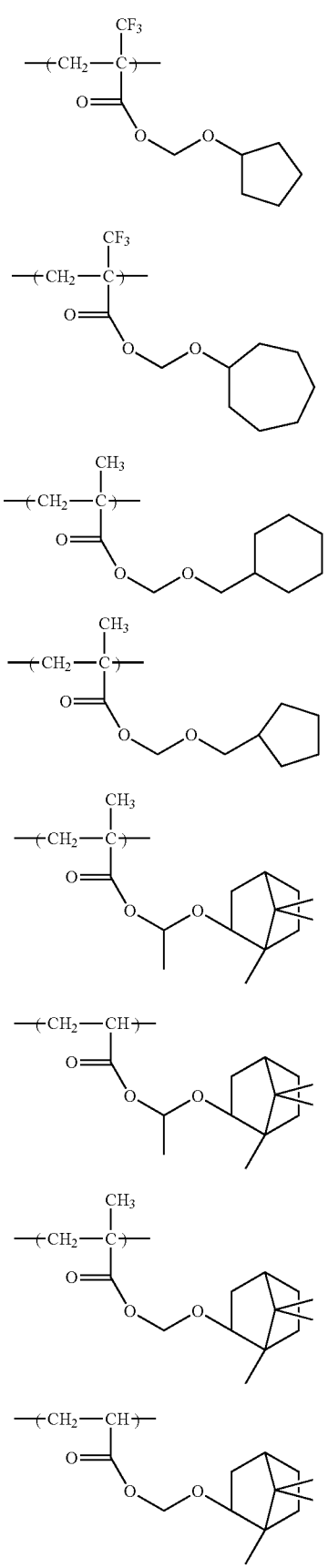
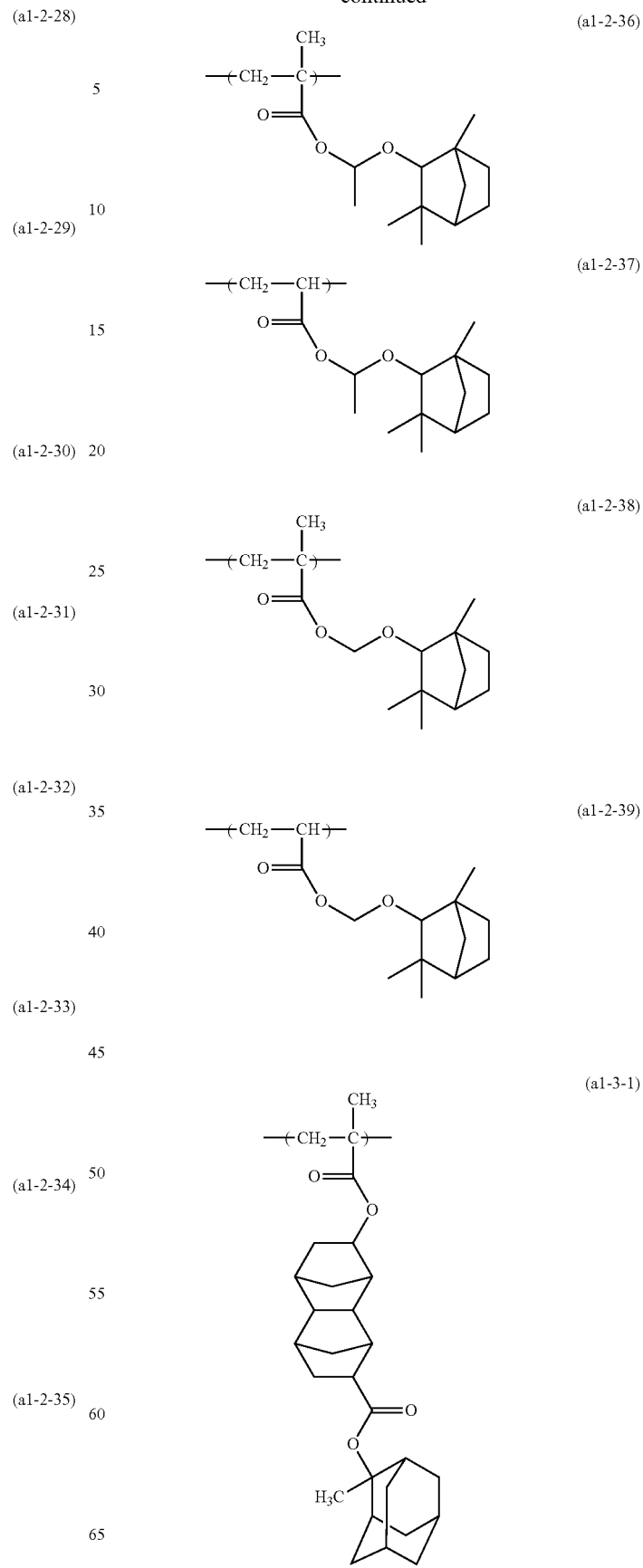

-continued
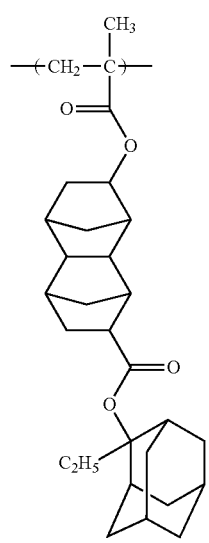
(a1-3-2)
(a1-3-3)
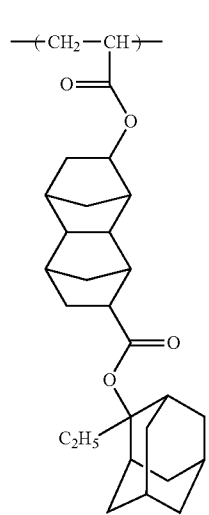
(a1-3-4)
-continued
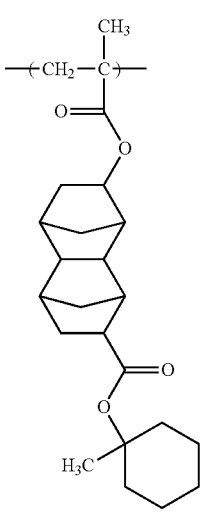
(a1-3-5)
(a1-3-6)
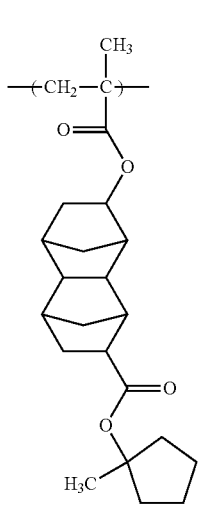
(a1-3-7)

(a1-3-8)
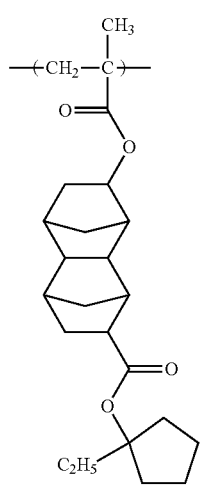
(a1-3-11)
(a1-3-9)
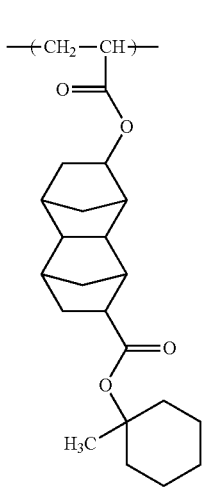
(a1-3-12)
(a1-3-10)
(a1-3-13)

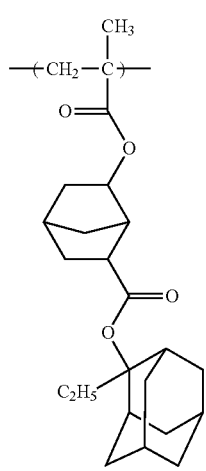
(a1-3-14)
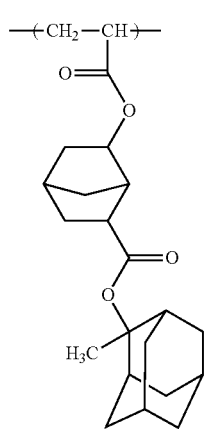
(a1-3-15)
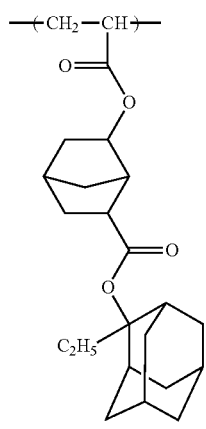
(a1-3-16)
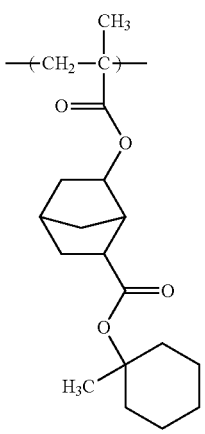
(a1-3-17)
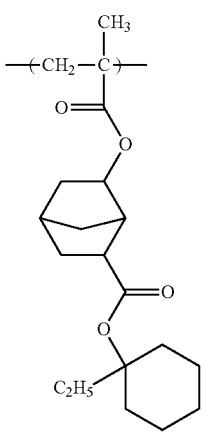
(a1-3-18)
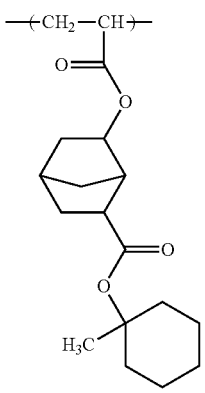
(a1-3-19)
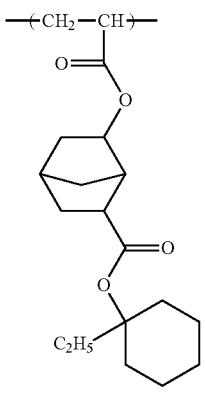
(a1-3-20)

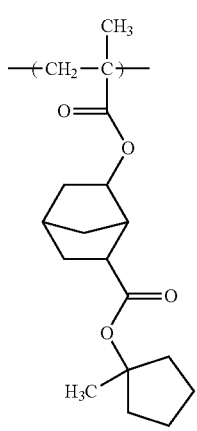 (a1-3-21)
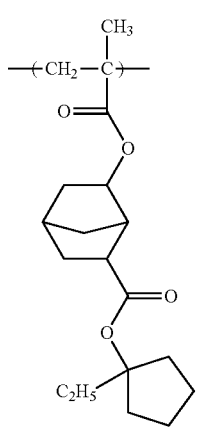 (a1-3-22)
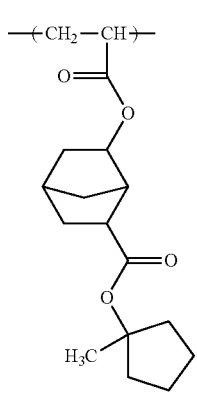 (a1-3-23)
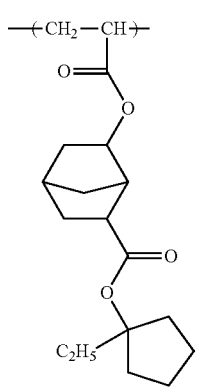 (a1-3-24)
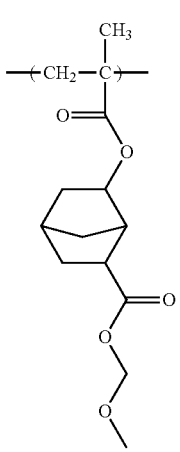 (a1-4-1)
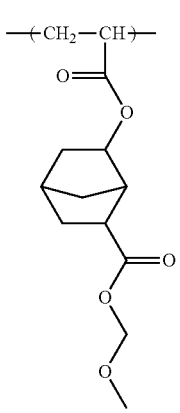 (a1-4-2)
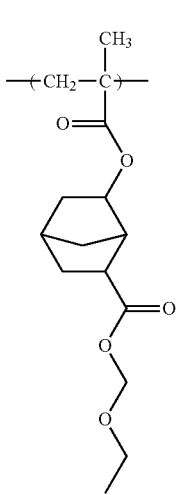 (a1-4-3)

(a1-4-4)
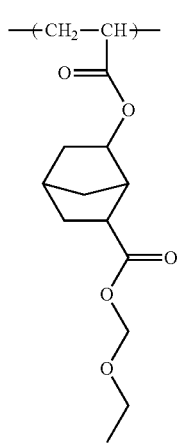
(a1-4-7)
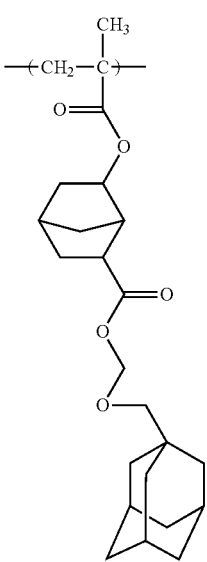
(a1-4-5)
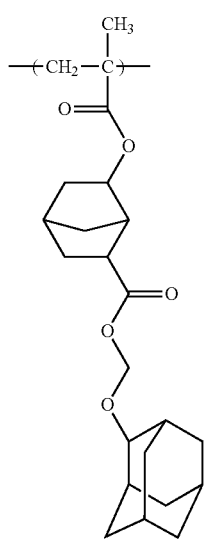
(a1-4-8)
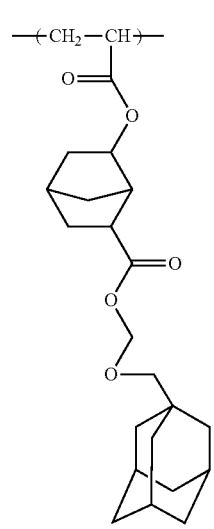
(a1-4-6)
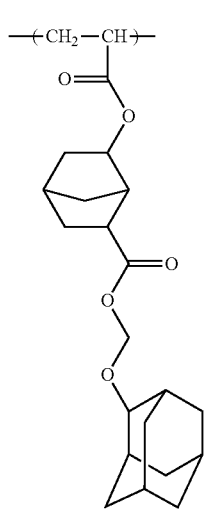
(a1-4-9)
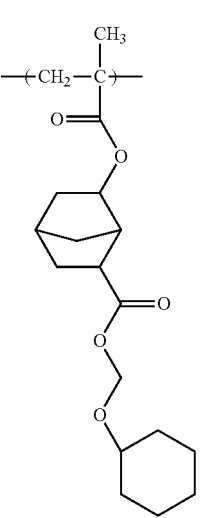

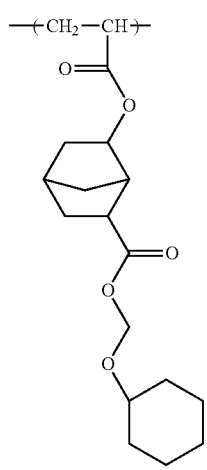
(a1-4-10)
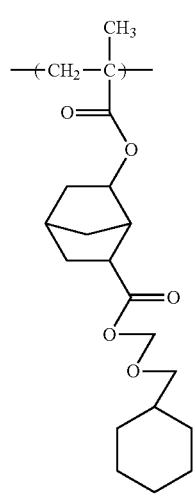
(a1-4-11)
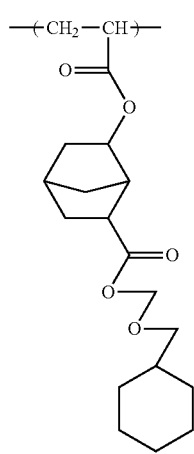
(a1-4-12)
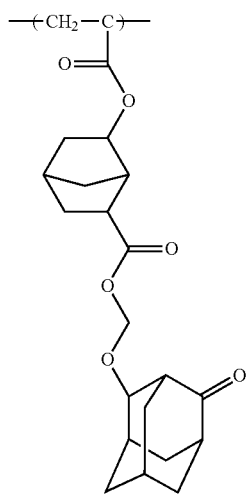
(a1-4-13)
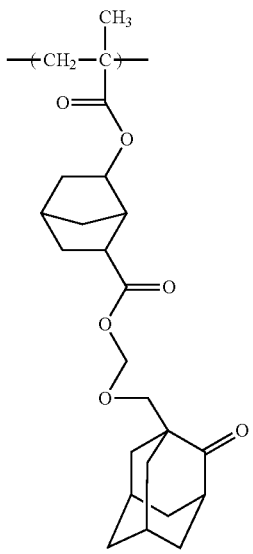
(a1-4-14)
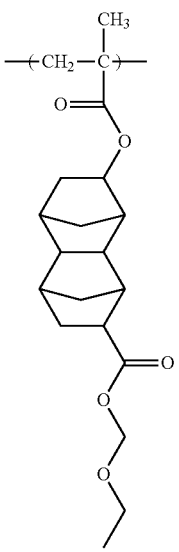
(a1-4-15)

(a1-4-16)
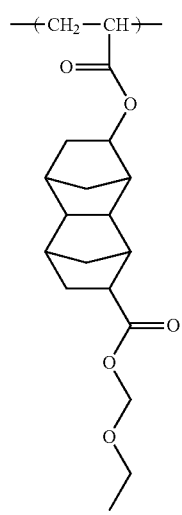
(a1-4-18)
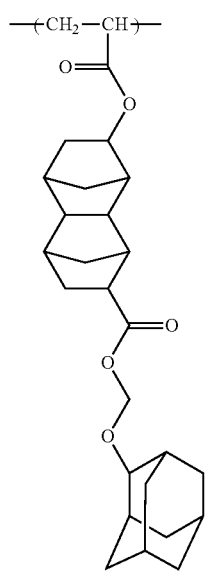
(a1-4-17)
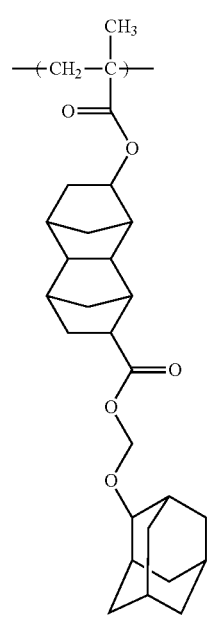
(a1-4-19)
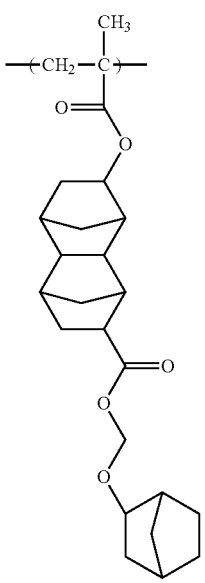

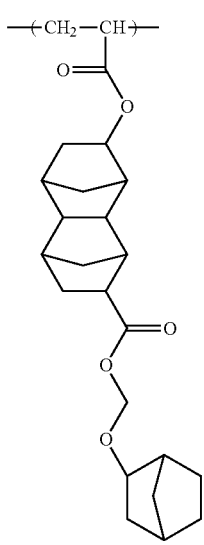
(a1-4-20)
(a1-4-21)
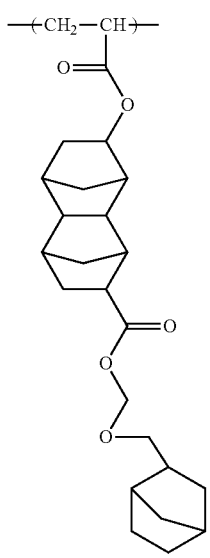
(a1-4-22)
(a1-4-23)

(a1-4-24)

(a1-4-25)

(a1-4-26)

(a1-4-27)

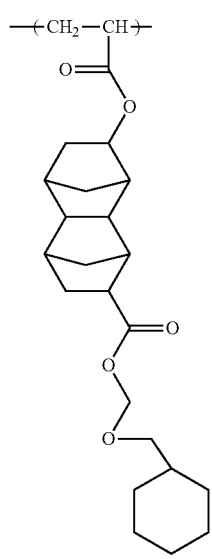
(a1-4-28)
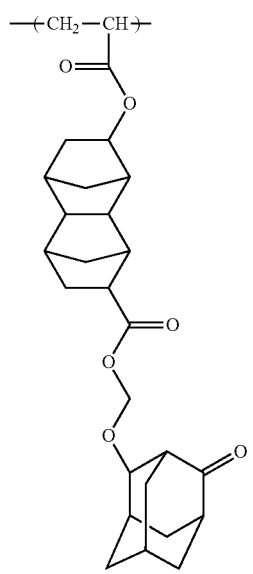
(a1-4-30)
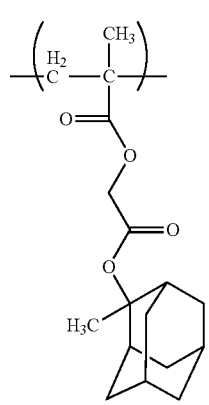
(a1-4-29)
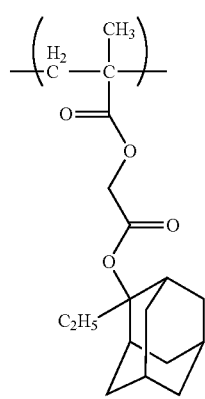
(a1-5-1)
(a1-5-2)

-continued
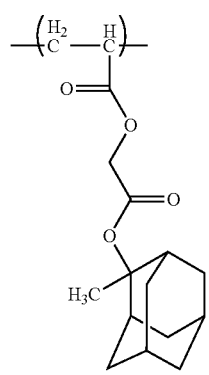 (a1-5-3)
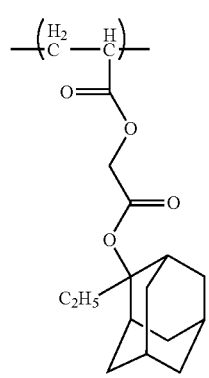 (a1-5-4)
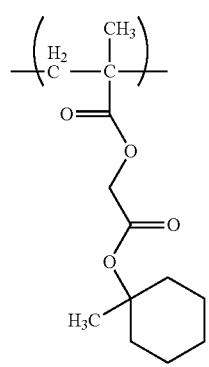 (a1-5-5)
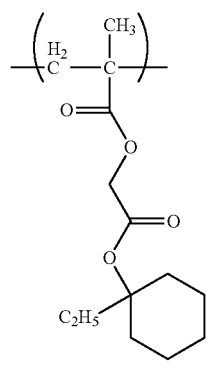 (a1-5-6)
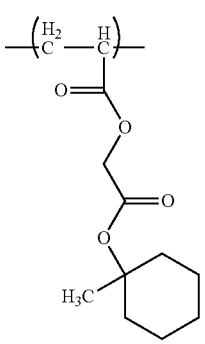 (a1-5-7)
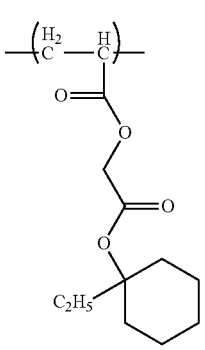 (a1-5-8)
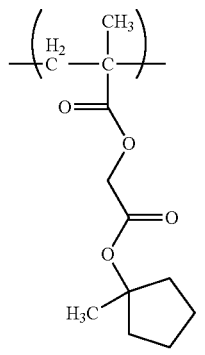 (a1-5-9)
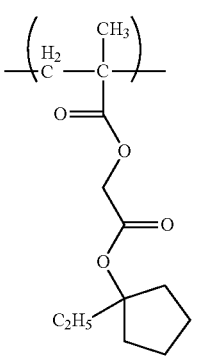 (a1-5-10)

(a1-5-11)

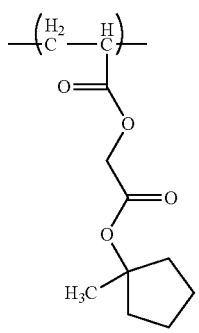

(a1-5-12)

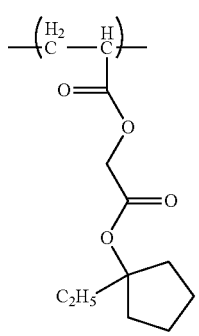

The constituent unit (a1) is preferably the constituent unit (a1-1). Specifically, the constituent unit (a1) is more preferably at least one member selected among the constituent units (a1-1-1) to (a1-1-6) or the constituent units (a1-1-35) to (a1-1-41).

Furthermore, in particular, the following constituent unit (a1-1-01) including the constituent units (a1-1-1) to (a1-1-4) or the following constituent unit (a1-1-02) including the constituent units (a1-1-35) to (a1-1-41) is also preferable as the constituent unit (a1).

(a1-1-01)

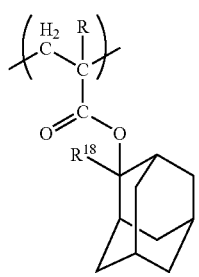

In the foregoing constituent unit (a1-1-01), R is the same as defined for R in the foregoing constituent unit (a1-0-1); and $R^{18}$ represents an alkyl group having from 1 to 5 carbon atoms. $R^{18}$ is preferably a methyl group or an ethyl group.

(a1-1-02)

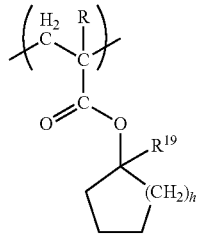

In the foregoing constituent unit (a1-1-02), R is the same as defined for R in the foregoing constituent unit (a1-0-1); and $R^{19}$ represents an alkyl group having from 1 to 5 carbon atoms. Also, h represents an integer of from 1 to 3.

$R^{19}$ is preferably a methyl group or an ethyl group, and more preferably an ethyl group. h is preferably 1 or 2, and more preferably 2.

In the case where the polymer compound (A) has the constituent unit (a1), the polymer compound (A) may have only one kind of the foregoing constituent unit (a1) or may have two or more kinds thereof.

In the case where the polymer compound (A) has the constituent unit (a1), a proportion of the constituent unit (a1) in the polymer compound (A) is preferably from 5 to 70% by mole, more preferably from 20 to 70% by mole, and further preferably from 25 to 55% by mole relative to the whole of the constituent units constituting the polymer compound (A). By regulating the proportion of the constituent unit (a1) in the polymer compound (A) to the lower limit value or more, when formed into a resist composition, a pattern can be easily obtained; whereas by regulating it to the upper limit value or less, the effect of the present invention for obtaining a photoresist composition having excellent adhesion to substrate and less pattern collapse is not impaired.

(Constituent Unit (a2))

The constituent unit (a2) is a constituent unit derived from a lactone-containing group-containing acrylate. The lactone-containing group as referred to herein expresses a group containing one lactone ring having an —O—C(O)— structure. In the constituent unit (a2), the case where the ester group of the foregoing acrylate has only the subject lactone ring as a cyclic structure is referred to as a "monocyclic group", and the case where it further has other cyclic structure is referred to as a "polycyclic group" regardless of its structure.

In the case where the polymer compound (A) is used for the formation of a resist film, the lactone-containing group of the constituent unit (a2) is effective for increasing the adhesion to a substrate of the resist film or increasing affinity with a developer containing water.

The constituent unit (a2) is not particularly limited, and an arbitrary unit can be used.

Specifically, a group obtainable from elimination of one hydrogen atom from γ-butyrolactone is exemplified as the lactone-containing monocyclic group. Also, groups obtainable from elimination of one hydrogen atom from a lactone ring-containing bicycloalkane, tricycloalkane or tetracycloalkane are exemplified as the lactone-containing polycyclic group.

More specifically, the following constituent units (a2-1) to (a2-6) are preferably exemplified as examples of the constituent unit (a2), but the constituent unit (a2) is not particularly limited thereto.

(a2-1)
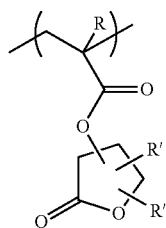

(a2-2)
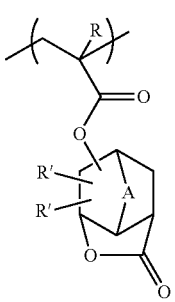

(a2-3)
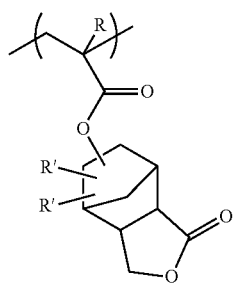

(a2-4)
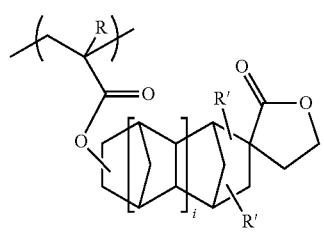

(a2-5)
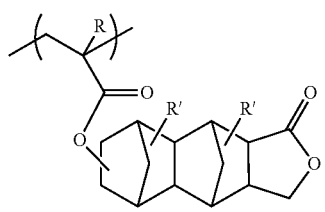

-continued (a2-6)
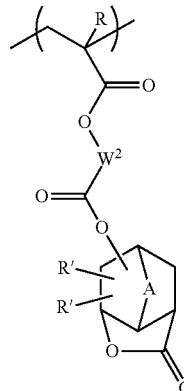

In the formulae, R is the same as defined for R in the constituent unit (a1-0-1). Each of R's independently represents a hydrogen atom, an alkyl group having from 1 to 5 carbon atoms, an alkoxy group having from 1 to 5 carbon atoms or —COOR$^{20}$ (R$^{20}$ represents an alkyl group having from 1 to 3 carbon atoms). W$^2$ represents an alkylene group having from 1 to 10 carbon atoms or a cycloalkylene group having from 3 to 10 carbon atoms. A represents an alkylene group having from 1 to 5 carbon atoms or an oxygen atom. Also, i represents 0 or 1.

R is preferably a methyl group, an ethyl group or a trifluoromethyl group, and more preferably a methyl group or an ethyl group.

Examples of the alkyl group having from 1 to 5 carbon atoms which each of R's represents include a methyl group, an ethyl group, various propyl groups, various butyl groups and so forth. Of these, a methyl group or an ethyl group is preferable.

—COOR$^{20}$ which each of R's represents is preferably —COOCH$_3$. In this connection, from the viewpoint of easiness of industrial availability, all R's are preferably a hydrogen atom.

The alkylene group having from 1 to 10 carbon atoms which W$^2$ represents may be straight chain or branched chain. Examples of the subject alkylene group include a methylene group, an ethane-1,1-diyl group, an ethane-1,2-diyl group, a propane-1,1-diyl group, a propane-1,2-diyl group, a propane-1,3-diyl group, a pentane-1,5-diyl group, a hexane-1,6-diyl group and so forth. Of these, an alkylene group having from 1 to 5 carbon atoms is preferable, an alkylene group having from 1 to 3 carbon atoms is more preferable, and a methylene group is further preferable.

Examples of the cycloalkylene group having from 3 to 10 carbon atoms which W$^2$ represents include a cyclopentanediyl group, a cyclohexanediyl group and so forth.

Examples of the alkylene group having from 1 to 5 carbon atoms which A represents include a methylene group, an ethane-1,1-diyl group, an ethane-1,2-diyl group, a propane-1,1-diyl group, a propane-1,2-diyl group, a propane-1,3-diyl group, a propane-2,2-diyl group, a pentane-1,5-diyl group and so forth. A is preferably a methylene group or an oxygen atom.

Examples of the foregoing constituent units (a2-1) to (a2-6) are shown below, but the constituent units (a2-1) to (a2-6) are not particularly limited thereto.

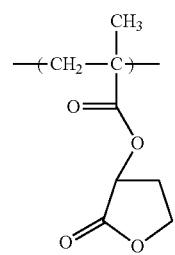 (a2-1-1)
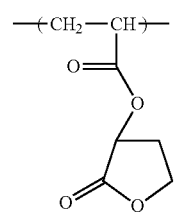 (a2-1-2)
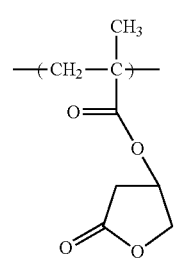 (a2-1-3)
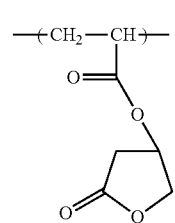 (a2-1-4)
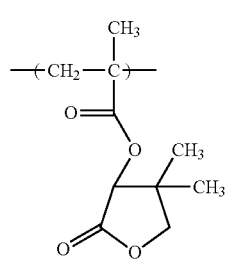 (a2-1-5)
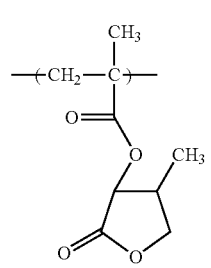 (a2-1-6)
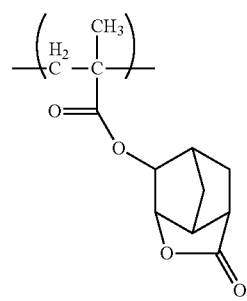 (a2-2-1)
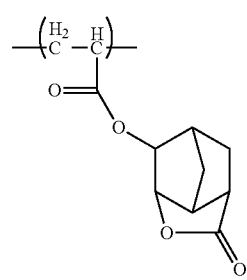 (a2-2-2)
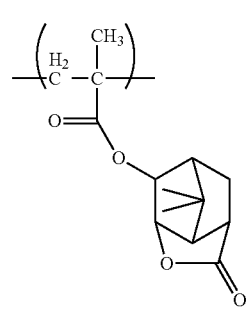 (a2-2-3)
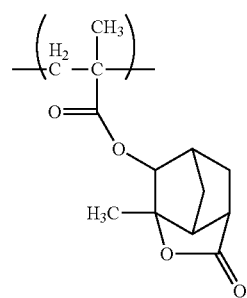 (a2-2-4)
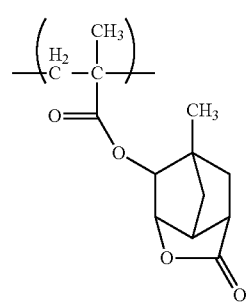 (a2-2-5)

(a2-2-6) 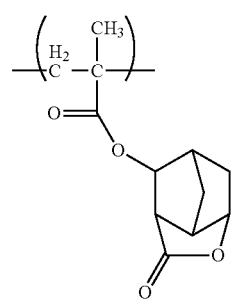
(a2-2-7) 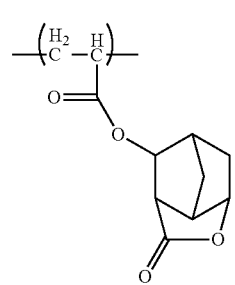
(a2-2-8) 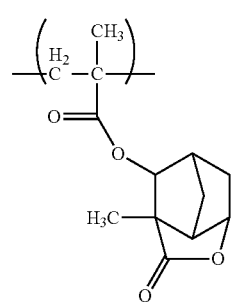
(a2-2-9) 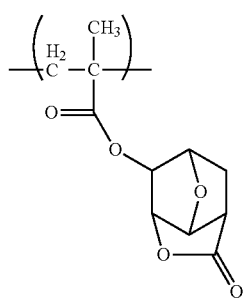
(a2-2-10) 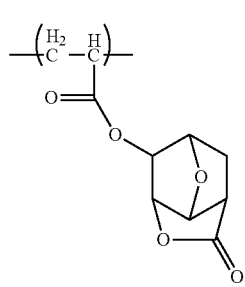
(a2-2-11) 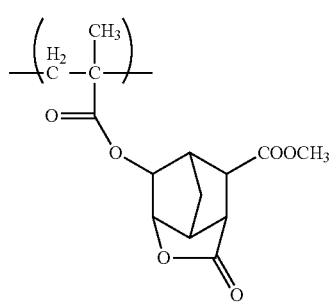
(a2-3-1) 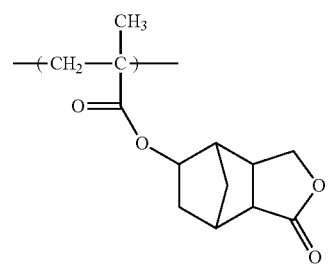
(a2-3-2) 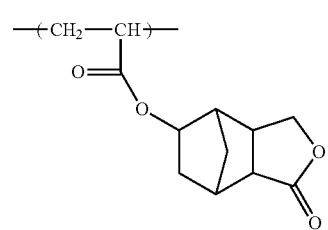
(a2-3-3) 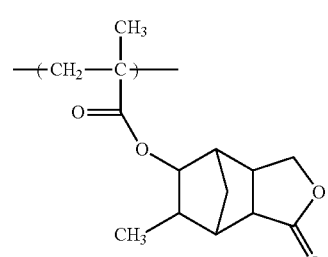
(a2-3-4)
(a2-3-5) 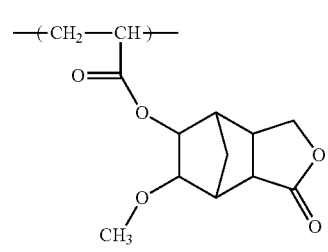

(a2-3-6)
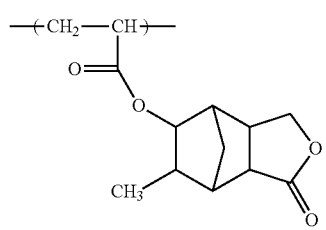
(a2-3-7)
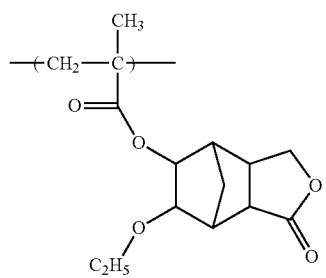
(a2-3-8)
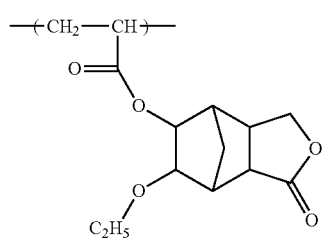
(a2-3-9)
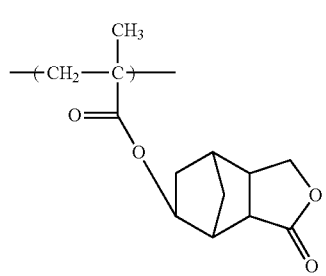
(a2-3-10)
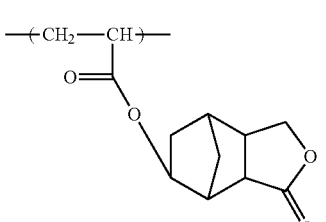
(a2-4-1)
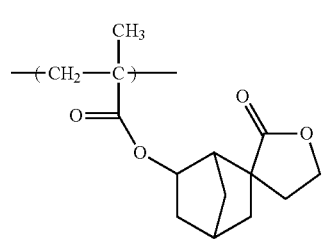
(a2-4-2)
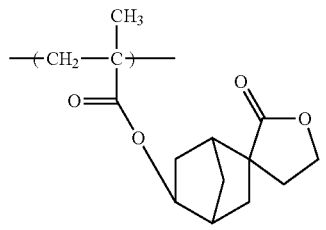
(a2-4-3)
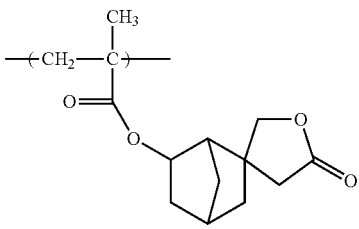
(a2-4-4)
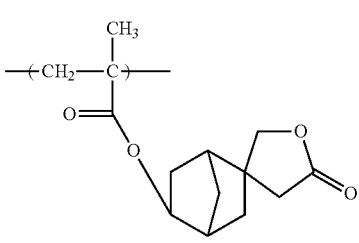
(a2-4-5)
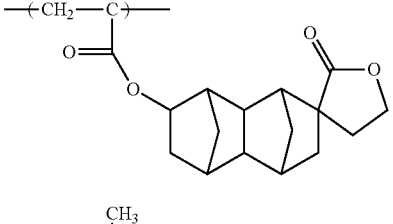
(a2-4-6)
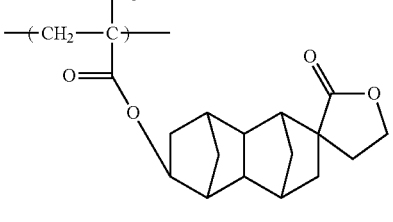
(a2-4-7)
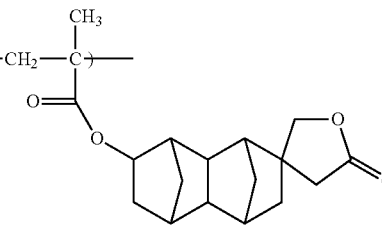
(a2-4-8)
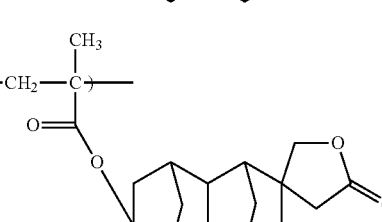

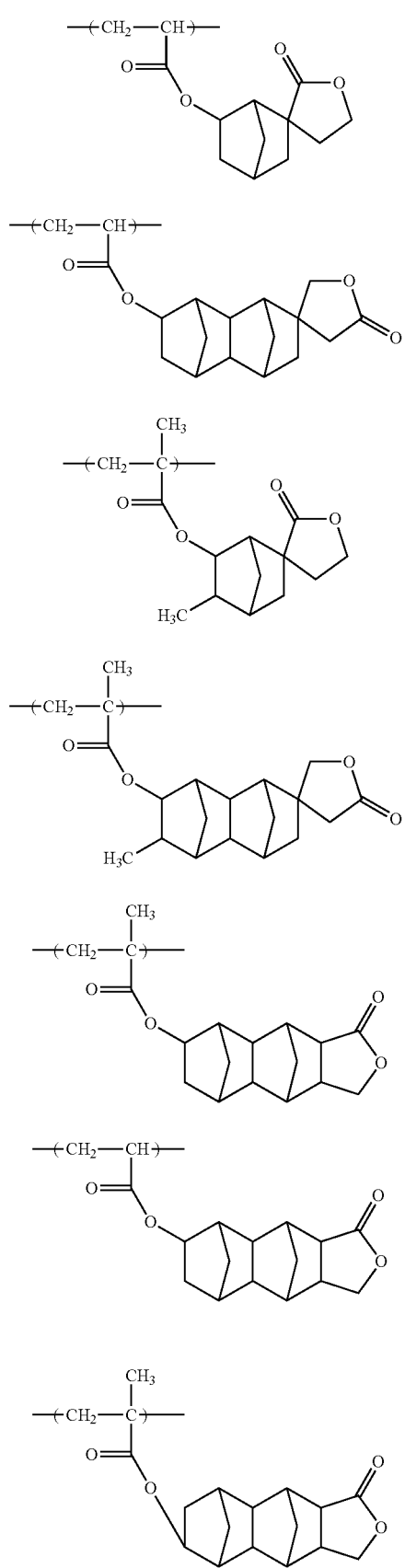
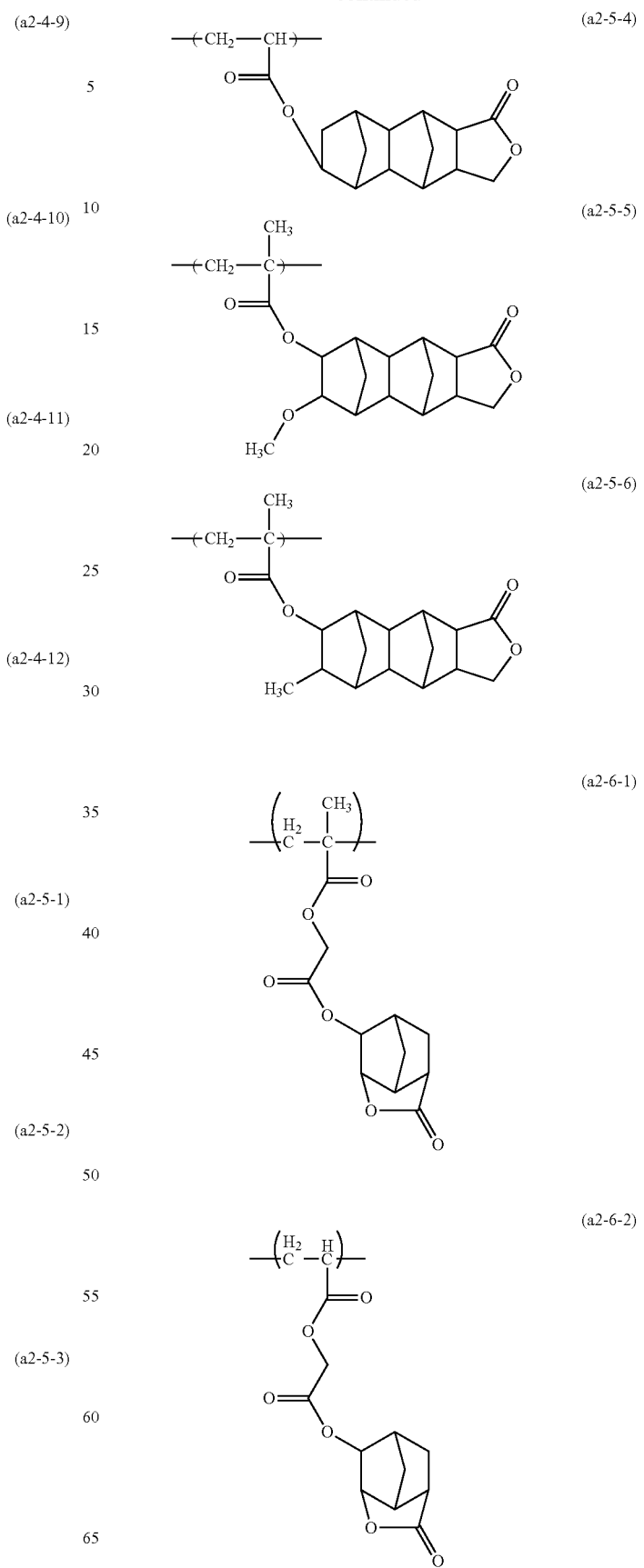

-continued
(a2-6-3)
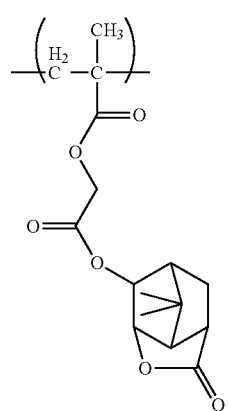
(a2-6-4)
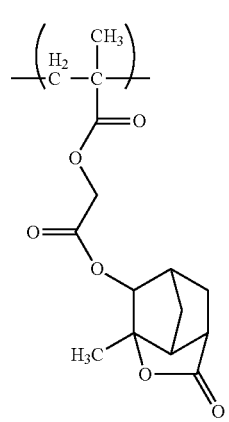
(a2-6-5)
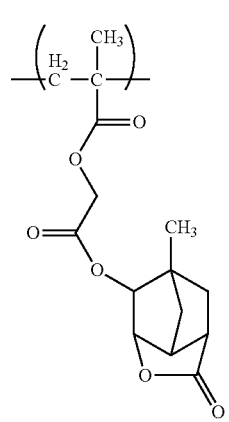
(a2-6-6)
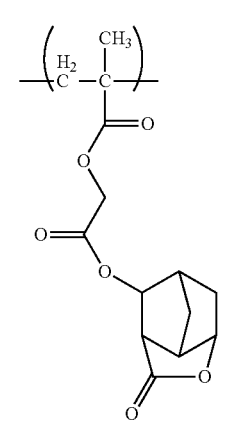
-continued
(a2-6-7)
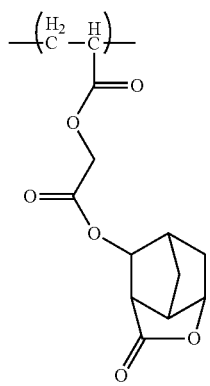
(a2-6-8)
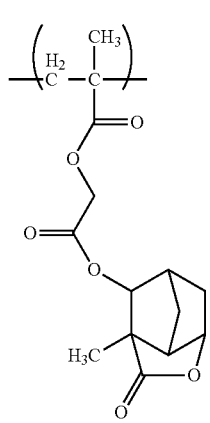
(a2-6-9)
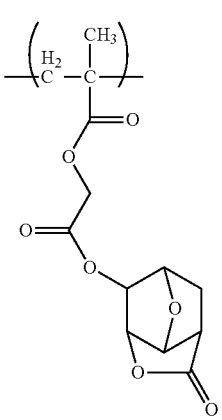
(a2-6-10)
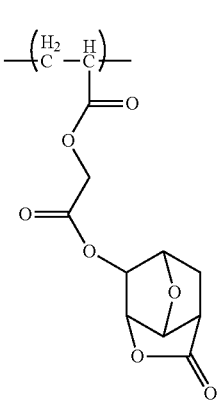

(a2-6-11)

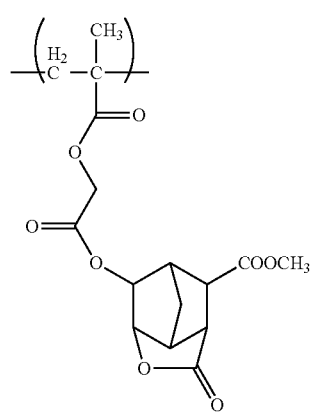

Of these, it is preferable to use at least one member selected among the constituent elements (a2-1) to (a2-3). Specifically, it is preferable to use at least one member selected among the constituent elements (a2-1-1), (a2-1-2), (a2-2-1), (a2-2-2), (a2-3-1), (a2-3-2), (a2-3-9) and (a2-3-10).

In the case where the polymer compound (A) has the constituent unit (a2), the polymer compound (A) may have only one kind of the foregoing constituent unit (a2) or may have two or more kinds thereof.

In the case where the polymer compound (A) has the constituent unit (a2), a proportion of the constituent unit (a2) in the polymer compound (A) is preferably from 1 to 60% by mole, more preferably from 10 to 55% by mole, and further preferably from 20 to 55% by mole relative to the whole of the constituent units constituting the polymer compound (A). By regulating the proportion of the constituent unit (a2) in the polymer compound (A) to the lower limit value or more, the effect to be brought in view of the fact that the constituent unit (a2) is incorporated is sufficiently obtained; whereas by regulating it to an upper limit value or less, the effect of the present invention for obtaining a photoresist composition having excellent adhesion to substrate and less pattern collapse is not impaired.

(Constituent Unit (a3))

The constituent unit (a3) is a constituent unit derived from a polar group-containing aliphatic hydrocarbon group-containing acrylate. In view of the fact that the polymer compound (A) has the constituent unit (a3), hydrophilicity of the polymer compound (A) is increased; and in using the subject polymer compound (A) as a substrate component of a positive type resist composition to form a positive type resist pattern, affinity with a developer (alkaline aqueous solution) is increased, and solubility in alkalis in an exposed area is enhanced, thereby contributing to an enhancement of resolution.

Examples of the polar group include a hydroxyl group, a hydroxyalkyl group, a cyano group, a carboxy group, a fluorinated hydroxyalkyl group (hydroxyalkyl group obtainable from substitution of a part of hydrogen atoms bonded to a carbon atom with a fluorine atom) and so forth, with a hydroxyl group and a hydroxyalkyl group being preferable.

As the constituent unit (a3), the following constituent units (a3') and (a3") are preferable.

The constituent unit (a3') is a constituent unit derived from a hydroxyl group-containing alicyclic group-containing acrylate.

In the "hydroxyl group-containing alicyclic group", the hydroxyl group may be bonded directly to the alicyclic ring, or may be bonded indirectly thereto as, for example, a hydroxyalkyloxy group, etc.

The alkyl group in the hydroxyalkyloxy group may be straight chain or branched chain. Though a carbon number of the subject alkyl group is not particularly limited, it is preferably from 2 to 5, more preferably from 2 to 4, and further preferably 2 or 3. Though a hydroxyl group number in the hydroxyalkyl group is not particularly limited, it is preferably from 1 to 4, more preferably from 1 to 3, and further preferably 1 or 2. The subject hydroxyl group is preferably a primary hydroxyl group or a secondary hydroxyl group, and more preferably a primary hydroxyl group.

The hydroxyalkyloxy group is preferably a monohydroxyalkyloxy group or a dihydroxyalkyloxy group, and more preferably a monohydroxyethyl group, a monohydroxypropyl group or a dihydroxypropyl group.

A hydroxyl group number bonding to the alicyclic group is preferably from 1 to 3, and more preferably 1.

The alicyclic group may have a substituent, or may be unsubstituted. Examples of the subject substituent include an alkyl group having from 1 to 5 carbon atoms, a fluorine atom, a fluorinated alkyl group having from 1 to 5 carbon atoms which is substituted with a fluorine atom, an oxygen atom (=O) and so forth.

The subject alicyclic group includes an alicyclic hydrocarbon group composed of carbon and hydrogen; a heterocyclic group obtainable from substitution of a part of carbon atoms constituting the ring of the subject alicyclic hydrocarbon group with a hetero atom such as an oxygen atom, a nitrogen atom, a sulfur atom, etc.; and so forth. The alicyclic group is preferably an alicyclic hydrocarbon group.

Though the alicyclic group may be either saturated or unsaturated, it is preferably saturated because it is high in transparency against an ArF excimer laser or the like and excellent in resolution, depth of focus (DOF) and the like.

Though the alicyclic group may be either a monocyclic group or a polycyclic group, it is preferably a polycyclic group. Also, a carbon number of the alicyclic group is preferably from 5 to 15.

Specific examples of the alicyclic group (in a state before the hydroxyl group is bonded) include the following.

That is, examples of the monocyclic group include groups obtainable from elimination of two or more hydrogen atoms of a cycloalkane; and so forth. More specifically, groups obtainable from elimination of two or more hydrogen atoms from cyclopentane or cyclohexane are exemplified, and a group obtainable from elimination of two hydrogen atoms from cyclohexane is preferable.

Examples of the polycyclic group include groups obtainable from elimination of two or more hydrogen atoms from a bicycloalkane, a tricycloalkane, a tetracycloalkane or the like; and so forth. More specifically, groups obtainable from elimination of two or more hydrogen atoms from a polycycloalkane such as adamantane, norbornane, isobornane, tricyclodecane, tetracyclododecane, etc.; and so forth are exemplified.

Of these, from the viewpoint of easiness of industrial availability, a group obtainable from elimination of two hydrogen atoms from cyclohexane, adamantane, norbornane or tetracyclododecane is preferable; and a group obtainable from elimination of two hydrogen atoms from adamantane or norbornane is more preferable.

In the constituent unit (a3'), it is preferable that the hydroxyl group-containing alicyclic group is bonded to a terminal oxygen atom of the carbonyloxy group [—C(O)—O—] of the acrylate.

As a preferred specific example of the constituent unit (a3'), the following constituent unit (a3'-1) is exemplified.

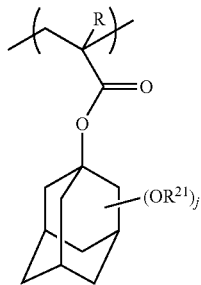

(a3'-1)

In the foregoing constituent unit (a3'-1), R is the same as defined for R in the constituent unit (a1-0-1). $R^{21}$ is a hydrogen atom or a hydroxyalkyl group having from 1 to 5 carbon atoms; and j is an integer of from 1 to 3.

Examples of the alkyl group in the hydroxyalkyl group having from 1 to 5 carbon atoms which $R^{21}$ represents include a methyl group, an ethyl group, various propyl groups, various butyl groups and so forth. A carbon number of the subject alkyl group is preferably from 1 to 4, and more preferably 2 or 3.

Though a hydroxyl group number in the hydroxyalkyl group of $R^{21}$ is not particularly limited, it is preferably from 1 to 4, more preferably from 1 to 3, and further preferably 1 or 2. The subject hydroxyl group is more preferably a primary hydroxyl group or a secondary hydroxyl group, and further preferably a primary hydroxyl group.

In the present invention, $R^{21}$ is preferably a monohydroxyalkyl group, a dihydroxyalkyl group or a hydrogen atom, and more preferably a monohydroxyethyl group, a monohydroxypropyl group, a dihydroxypropyl group or a hydrogen atom.

j is preferably 1 or 2, and more preferably 1. In the case where j is 2, it is preferable that $OR^{21}$ is bonded at the 3-position and 5-position of the adamantyl group; and in the case where j is 1, it is preferable that $OR^{21}$ is bonded at the 3-position of the adamantyl group. The following constituent unit (a3'-11) is preferable as the constituent unit (a3'-1) [in the constituent unit (a3'-11), R and $R^{21}$ are the same as those described above, respectively].

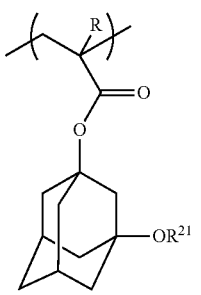

(a3'-11)

Also, the constituent unit (a3") is a constituent unit derived from an acrylic acid which does not have a cyclic structure, namely does not have an alicyclic hydrocarbon group or an aromatic hydrocarbon group and which has an alcoholic hydroxyl group in a side chain thereof.

Examples of the constituent unit having an alcoholic hydroxyl group in a side chain thereof include constituent units having a hydroxyalkyl group.

In the hydroxyalkyl group, the alkyl group may be straight chain or branched chain. Though a carbon number of the subject alkyl group is not particularly limited, it is preferably from 1 to 20, more preferably from 1 to 16, and further preferably from 1 to 12. Though a hydroxyl group number is not particularly limited, it is preferably 1 or 2, and more preferably 1.

The hydroxyalkyl group may be, for example, bonded directly to a carbon atom at the α-position of a main chain thereof (a portion where an ethylenically double bond of acrylic acid is cleaved), or may be substituted on the hydrogen atom of the carboxy group of acrylic acid to constitute an ester. In the constituent unit (a3"), it is preferable that the hydroxyalkyl group is present in at least one or both of them.

In this connection, in the case where the hydroxyalkyl group is not bonded at the α-position, a halogenated or non-halogenated alkyl group may be bonded to the carbon atom at the α-position in place of the hydrogen atom. As to the halogenated or non-halogenated alkyl group, the same explanation for R in the foregoing constituent unit (a1-0-1) is applicable.

The following constituent unit (a3"-1) is preferable as the constituent unit (a3").

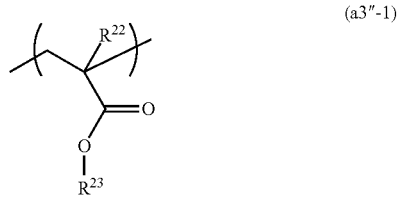

(a3"-1)

In the constituent unit (a3"-1), $R^{22}$ represents a hydrogen atom, a halogenated or non-halogenated alkyl group having from 1 to 10 carbon atoms or a hydroxyalkyl group having from 1 to 10 carbon atoms; and $R^{23}$ represents an alkyl group having from 1 to 20 carbon atoms or a hydroxyalkyl group having from 1 to 20 carbon atoms, provided that at least one of $R^{22}$ and $R^{23}$ represents a hydroxyalkyl group.

The hydroxyalkyl group which $R^{22}$ represents may be straight chain or branched chain, and it is preferably a hydroxyalkyl group having from 1 to 8 carbon atoms.

Though a hydroxyl group number in the subject hydroxyalkyl group is not particularly limited, it is usually 1. Also, the subject hydroxyl group is more preferably a primary or secondary hydroxyl group, and especially preferably a primary hydroxyl group.

The hydroxyalkyl group which $R^{22}$ represents is most preferably a hydroxymethyl group or a hydroxyethyl group.

The non-halogenated alkyl group which $R^{22}$ represents is preferably an alkyl group having from 1 to 8 carbon atoms, and more preferably an ethyl group or a methyl group.

The halogenated alkyl group which $R^{22}$ represents is a group obtainable from substitution of a part of all of hydrogen atoms of the foregoing alkyl group having from 1 to 5 carbon atoms (preferably an ethyl group or a methyl group) with a halogen atom (preferably a fluorine atom).

Examples of the alkyl group having from 1 to 20 carbon atoms which $R^{23}$ represents include a methyl group, an ethyl group, various propyl groups, various butyl groups, various hexyl groups, various octyl groups, various decyl groups, various dodecyl groups and so forth. Of these, an alkyl group having from 1 to 8 carbon atoms is preferable, and an alkyl group having from 1 to 5 carbon atoms is more preferable.

The hydroxyalkyl group which $R^{23}$ represents may be straight chain or branched chain, and a carbon number thereof is preferably not more than 10, and more preferably of 2 to 8. The hydroxyalkyl group is further preferably a hydroxyethyl group. Though the hydroxyl group number is not particularly limited, it is usually 1. Also, the subject hydroxyl group is more preferably a primary or secondary hydroxyl group, and further preferably a primary hydroxyl group.

Also, in addition to the foregoing constituent units (a3') and (a3"), the following constituent unit (a3-2) is preferable as the constituent unit (a3).

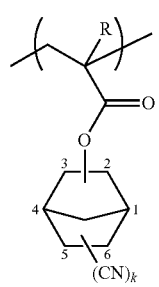

(a3-2)

In the foregoing constituent unit (a3-2), R is the same as defined for R in the constituent unit (a1-0-1). k is an integer of from 1 to 3.

k is preferably 1. It is preferable that the cyano group in the constituent unit (a3-2) is bonded at the 5-position or 6-position of the norbornyl group.

In the case where the polymer compound (A) has the constituent unit (a3), the polymer compound (A) may have only one kind of the foregoing constituent unit (a3) or may have two or more kinds thereof.

In the case where the polymer compound (A) has the constituent unit (a3), a proportion of the constituent unit (a3) in the polymer compound (A) is preferably from 5 to 50% by mole, more preferably from 5 to 40% by mole, and further preferably from 5 to 25% by mole relative to the whole of the constituent units constituting the subject polymer compound (A). By regulating the proportion of the constituent unit (a3) in the polymer compound (A) to the lower limit value or more, the effect to be brought in view of the fact that the constituent unit (a3) is incorporated is sufficiently obtained; whereas by regulating it to an upper limit value or less, the effect of the present invention for obtaining a photoresist composition having excellent adhesion to substrate and less pattern collapse is not impaired.

Also, in the case where the subject polymer compound (A) has the constituent unit (a3), it is preferable that the polymer compound (A) has the foregoing constituent unit (a3') as the constituent unit (a3); it is more preferable that the polymer compound (A) has a constituent unit in which $R^{21}$ in the foregoing constituent unit (a3'-1) is a hydrogen atom; and it is further preferable that the polymer compound (A) has a constituent unit in which $R^{21}$ in the foregoing constituent unit (a3'-11) is a hydrogen atom.

(Constituent Unit (a4))

The constituent unit (a4) is a constituent unit derived from a cycloalkyl(meth)acrylate.

The cycloalkyl group in the cycloalkyl(meth)acrylate is preferably one in which a number of carbons forming a ring is from 3 to 12, and more preferably one in which a number of carbons forming a ring is from 6 to 12; and from the viewpoint of easiness of industrial availability, it is further preferably a tricyclodecanyl group, an adamantyl group, a tetracyclododecanyl group, isobornyl group or a norbornyl group.

Such a cycloalkyl group may have a straight chain or branched chain alkyl group having from 1 to 5 carbon atoms as a substituent.

Specifically, the following constituent units (a4-1) to (a4-24) can be exemplified as the constituent unit (a4), but the constituent unit (a4) is not particularly limited thereto.

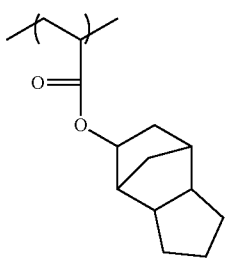

(a4-1)

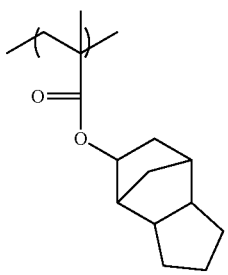

(a4-2)

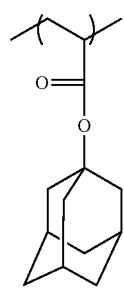

(a4-3)

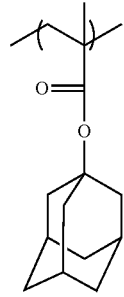

(a4-4)

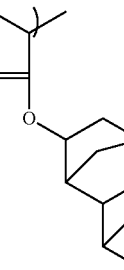

(a4-5)

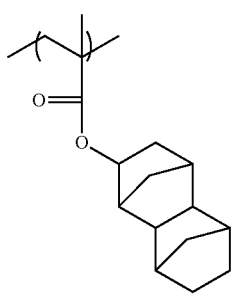 (a4-6)
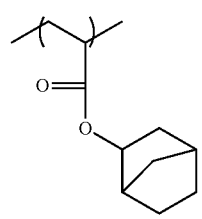 (a4-7)
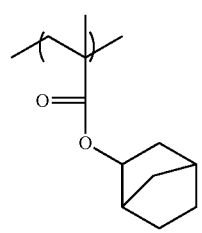 (a4-8)
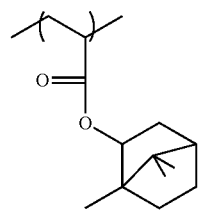 (a4-9)
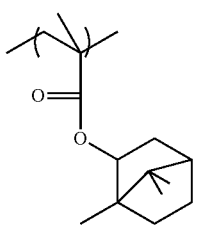 (a4-10)
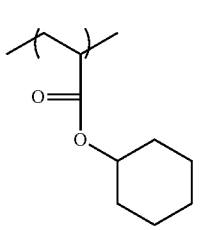 (a4-11)
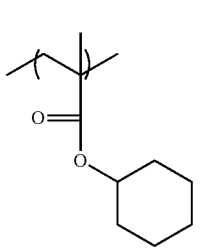 (a4-12)
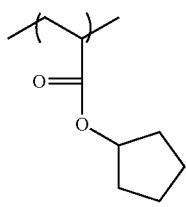 (a4-13)
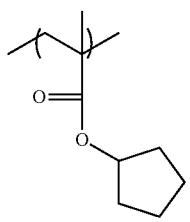 (a4-14)
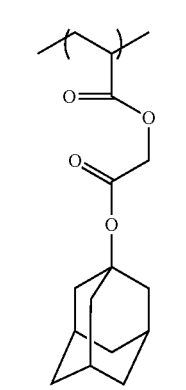 (a4-15)
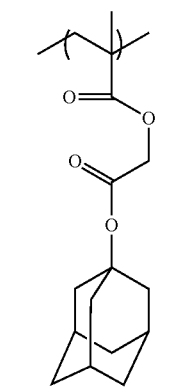 (a4-16)
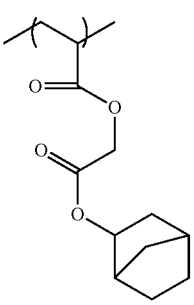 (a4-17)

(a4-18) 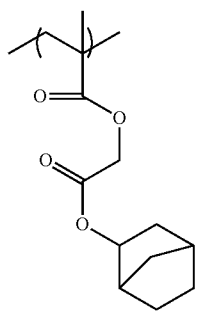

(a4-19) 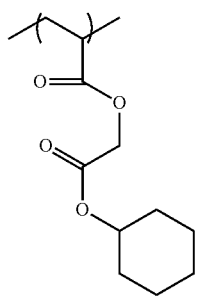

(a4-20) 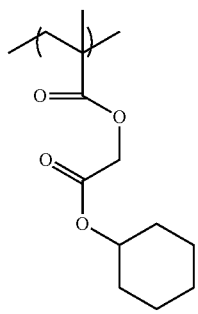

(a4-21) 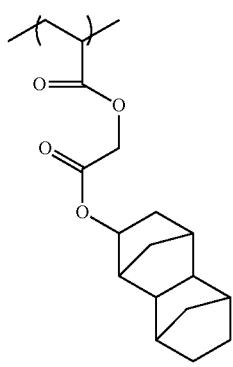

(a4-22) 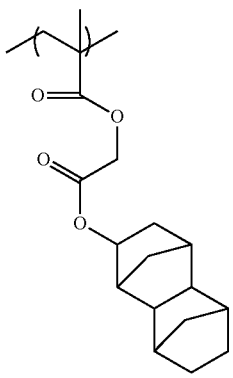

(a4-23) 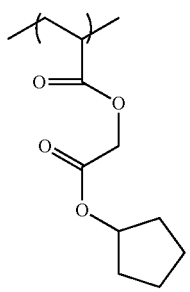

(a4-24) 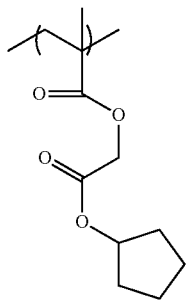

In the case where the polymer compound (A) has the constituent unit (a4), the polymer compound (A) may have only one kind of the foregoing constituent unit (a4) or may have two or more kinds thereof.

In the case where the polymer compound (A) has the constituent unit (a4), a proportion of the constituent unit (a4) in the polymer compound (A) is preferably from 1 to 30% by mole, and more preferably from 10 to 20% by mole relative to the total sum of the whole of the constituent units constituting the polymer compound (A). By regulating the proportion of the constituent unit (a4) in the polymer compound (A) to the lower limit value or more, the effect to be brought in view of the fact that the constituent unit (a4) is incorporated is sufficiently obtained; whereas by regulating it to an upper limit value or less, the effect of the present invention for obtaining a photoresist composition having excellent adhesion to substrate and less pattern collapse is not impaired.

(Other Constituent Unit (a5))

The polymer compound (A) may further have other constituent unit (a5) in addition to the foregoing constituent units (a0) to (a4) within the range where the effect of the present invention is not impaired.

The constituent unit (a5) is other constituent unit which is not classified into the foregoing constituent units (a0) to (a4), and it is a constituent unit which has hitherto been known as a constituent unit of a polymer compound to be used for resist resins for ArF excimer laser or KrF excimer laser (preferably for ArF excimer laser) or the like.

The polymer compound of the present invention is preferably a polymer composed of only the constituent unit (a0) or a copolymer composed of the constituent unit (a0) and at least one constituent unit selected from the group consisting of the constituent units (a1) to (a4).

As the polymer compound (A), the following copolymers (A1) to (A6) and the like are preferable.

Copolymer (A1): Copolymer having the constituent units (a0) and (a1)

Copolymer (A2): Copolymer having the constituent units (a0) and (a2)

Copolymer (A3): Copolymer having the constituent units (a0) and (a3)

Copolymer (A4): Copolymer having the constituent units (a0) and (a4)

Copolymer (A5): Copolymer having the constituent units (a0), (a1) and (a2)

Copolymer (A6): Copolymer having the constituent units (a0), (a1) and (a3)

Of these, the copolymers (A1), (A5) and (A6) are more preferable from the viewpoint of obtaining a polymer compound having excellent solubility in an organic solvent to be used for the preparation of a photoresist composition and the viewpoint of obtaining a photoresist composition having excellent adhesion to substrate and less pattern collapse.
(Production Method of Polymer Compound (A))

The polymer compound (A) of the present invention can be produced by means of radical polymerization according to the usual way. In particular, as a method for synthesizing the polymer compound (A) having small molecular weight distribution, living radical polymerization and the like can be exemplified. In a general radical polymerization method, at least one member of the acrylate derivative (1) and optionally, a monomer corresponding to at least one member of the foregoing constituent units (a1) to (a5) (such a monomer will be hereinafter referred to as "copolymerizable monomer") are polymerized in the presence of a radical polymerization initiator and a solvent and optionally, a chain transfer agent. Such a radical polymerization method is hereunder described.

A method for carrying out the radical polymerization is not particularly limited, and a customary method which is adopted for producing, for example, an acrylate based polymer compound, such as a solution polymerization method, an emulsion polymerization method, a suspension polymerization method, a bulk polymerization method, etc., can be adopted.

Examples of the radical polymerization initiator which is used for the production of the polymer compound (A) of the present invention include hydroperoxide compounds such as t-butyl hydroperoxide, cumene hydroperoxide, etc.; dialkyl peroxide compounds such as di-t-butyl peroxide, t-butyl-α-cumyl peroxide, di-α-cumyl peroxide, etc.; diacyl peroxide compounds such as benzoyl peroxide, diisobutyl peroxide, etc.; azo compounds such as 2,2'-azobisisobutyronitrile, dimethyl 2,2'-azobisisobutyrate, etc.; and so forth.

Though a use amount of the radical polymerization initiator can be properly chosen depending upon a polymerization condition such as the kind and use amount of each of the acrylate derivative (1), the copolymerizable monomer, the chain transfer and the solvent which are used for the polymerization reaction; a polymerization temperature; etc., it is in general in the range of from 0.005 to 0.2 moles, and preferably in the range of from 0.01 to 0.15 moles per mole of the whole of the polymerizable compounds [referring to the total sum of the acrylate derivative (1) and the copolymerizable monomer; hereinafter the same].

Examples of the chain transfer agent which is used for the production of the polymer compound (A) of the present invention include thiol compounds such as dodecanethiol, mercaptoethanol, mercaptopropanol, mercaptoacetic acid, mercaptopropionic acid, etc. These may be used singly or in combinations of two or more kinds thereof.

In the case of using the chain transfer agent, its use amount is in general in the range of 0.005 to 0.2 moles, and preferably in the range of from 0.01 to 0.15 moles per mole of the whole of the polymerizable compounds.

The production of the polymer compound (A) of the present invention can be in general carried out in the presence of a solvent. The solvent is not particularly limited so far as it does not impair the polymerization reaction, and examples thereof include glycol ethers such as propylene glycol monoethyl ether, propylene glycol monomethyl ether acetate, ethylene glycol monomethyl ether, ethylene glycol monomethyl ether acetate, ethylene glycol monomethyl ether propionate, ethylene glycol monobutyl ether, ethylene glycol monobutyl ether acetate, diethylene glycol dimethyl ether, etc.; esters such as ethyl lactate, methyl 3-methoxypropionate, methyl acetate, ethyl acetate, propyl acetate, etc.; ketones such as acetone, methyl ethyl ketone, methyl isopropyl ketone, methyl isobutyl ketone, methyl amyl ketone, cyclopentanone, cyclohexanone, etc.; ethers such as diethyl ether, diisopropyl ether, dibutyl ether, tetrahydrofuran, 1,4-dioxane, etc.; and so forth. The solvent may be used singly or in combinations of two or more kinds thereof.

A use amount of the solvent is in general in the range of from 0.5 to 20 parts by mass per part by mass of the whole of the polymerizable compounds, and from the viewpoint of economy, it is preferably in the range of from 1 to 10 parts by mass.

In the production of the polymer compound (A), a polymerization temperature is in general in the range of from 40 to 150° C., and from the viewpoint of stability of the polymer compound (A) to be formed, it is preferably in the range of from 60 to 120° C.

Though a production time of the polymer compound (A) varies depending upon a polymerization condition such as the kind and use amount of each of the acrylate derivative (1), the copolymerizable monomer, the polymerization initiator and the solvent; the temperature of polymerization reaction; etc., it is in general in the range of from 30 minutes to 48 hours, and more preferably in the range of from 1 hour to 24 hours.

The thus obtained polymer compound (A) can be isolated by a usual operation such as reprecipitation, etc. The isolated polymer compound (A) can also be dried by means of vacuum drying or the like.

Examples of a solvent which is used for the foregoing reprecipitation operation include aliphatic hydrocarbons such as pentane, hexane, etc.; alicyclic hydrocarbons such as cyclohexane, etc.; aromatic hydrocarbons such as benzene, xylene, etc.; halogenated hydrocarbons such as methylene chloride, chloroform, chlorobenzene, dichlorobenzene, etc.; nitrated hydrocarbons such as nitromethane, etc.; nitriles such as acetonitrile, benzonitrile, etc.; ethers such as diethyl ether, diisopropyl ether, tetrahydrofuran, 1,4-dioxane, etc.; ketones such as acetone, methyl ethyl ketone, etc.; carboxylic acids such as acetic acid, etc.; esters such as ethyl acetate, butyl acetate, etc.; carbonates such as dimethyl carbonate, diethyl carbonate, ethylene carbonate, etc.; alcohols such as methanol, ethanol, propanol, isopropyl alcohol, butanol, etc.; and water. Such a solvent may be used singly or in combinations of two or more kinds thereof.

Though a use amount of the solvent in the reprecipitation operation varies depending upon the kind of the polymer compound (A) and the kind of the solvent, it is in general in the range of from 0.5 to 100 parts by mass per part by mass of the polymer compound (A), and from the viewpoint of economy, it is more preferably in the range of from 1 to 50 parts by mass.

Specific examples of the polymer compound (A) obtained by the foregoing method include polymer compounds represented by the following structural formulae [(A)-1] to [(A)-44] (in the formulae, each of $R^{24}$ to $R^{36}$ independently represents a hydrogen atom, a methyl group or a trifluoromethyl group; each of a, b, c, d and e represents a molar ratio of each of the repeating units; and (a+b)=1 and (c+d+e=1)); and so forth, but the polymer compound (A) is not particularly limited thereto.

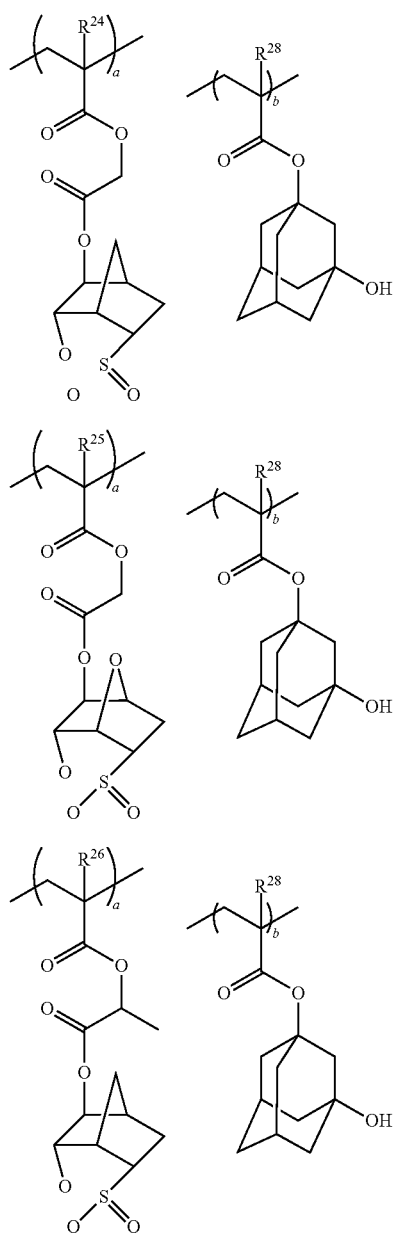

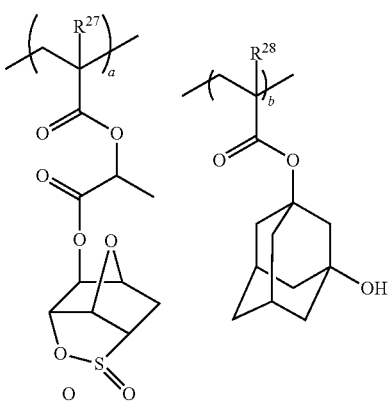

(A)-4

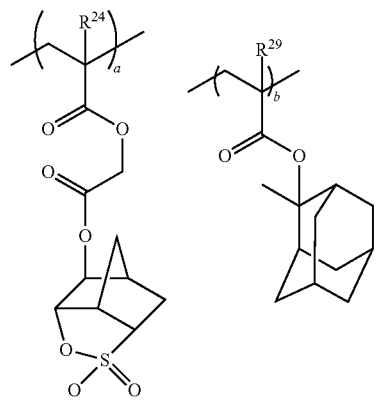

(A)-5

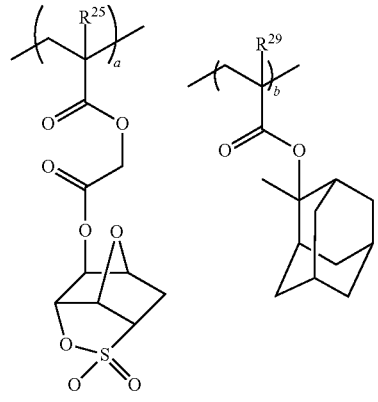

(A)-6

(A)-7

(A)-8
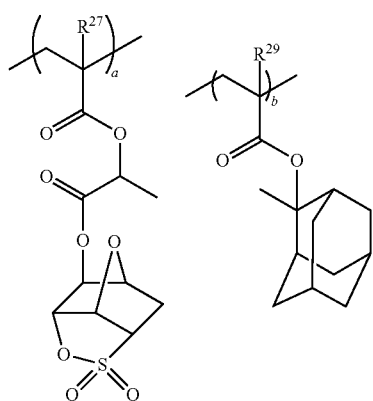
(A)-9
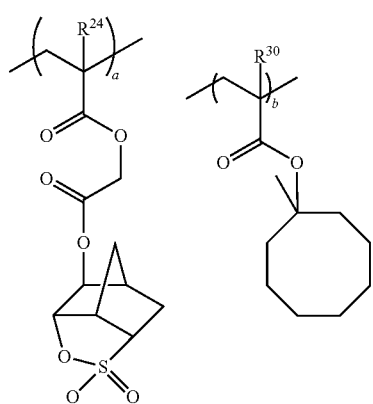
(A)-10
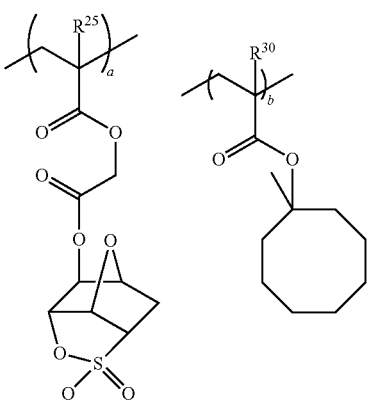
(A)-11
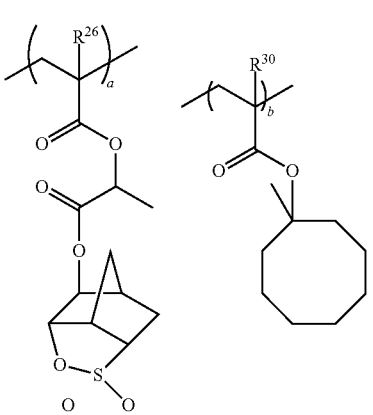
(A)-12
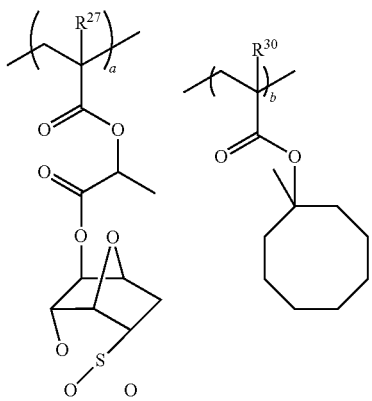
(A)-13
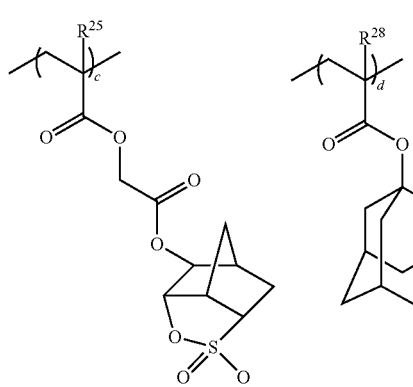
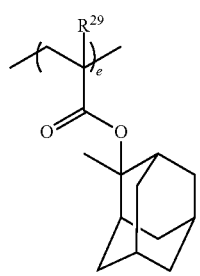
(A)-14
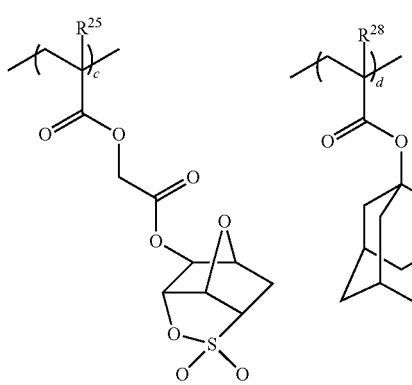

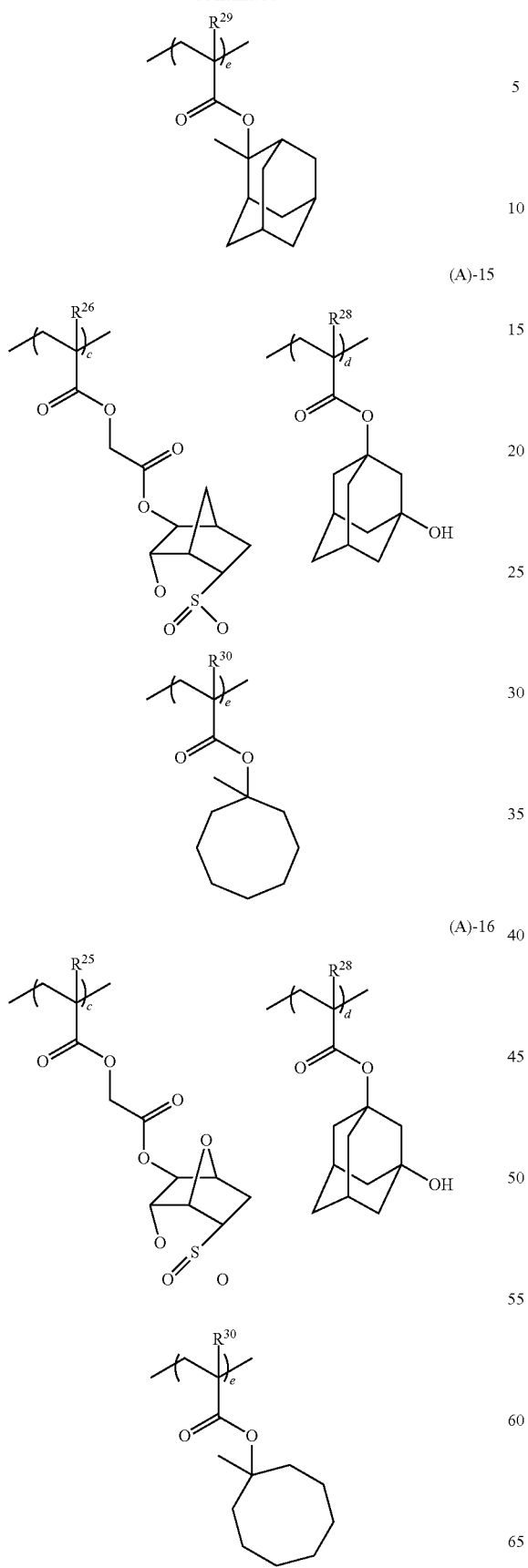
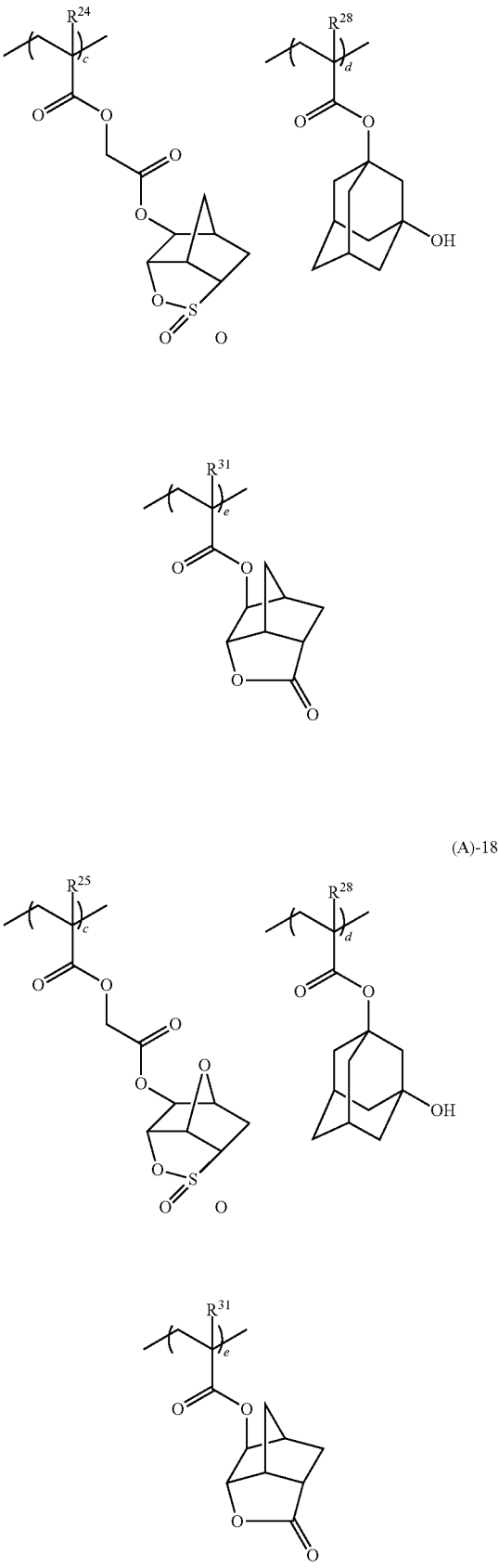

(A)-19
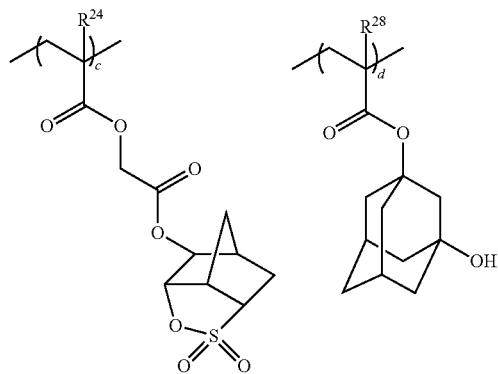
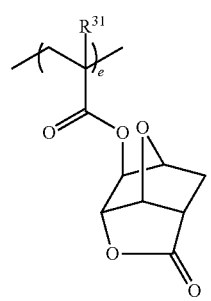
(A)-20
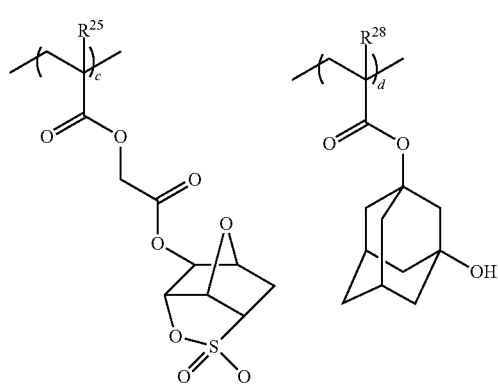
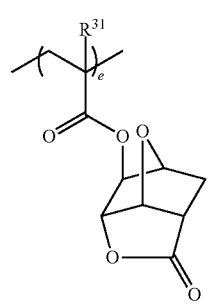
(A)-21
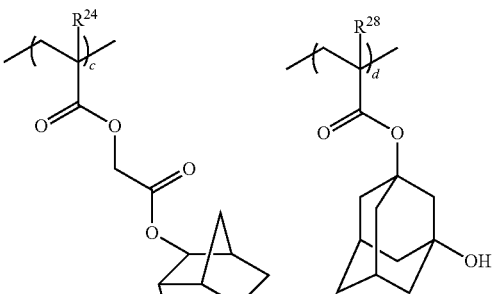
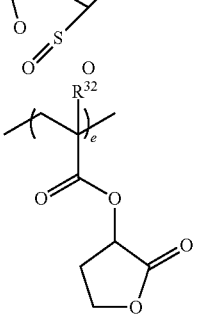
(A)-22
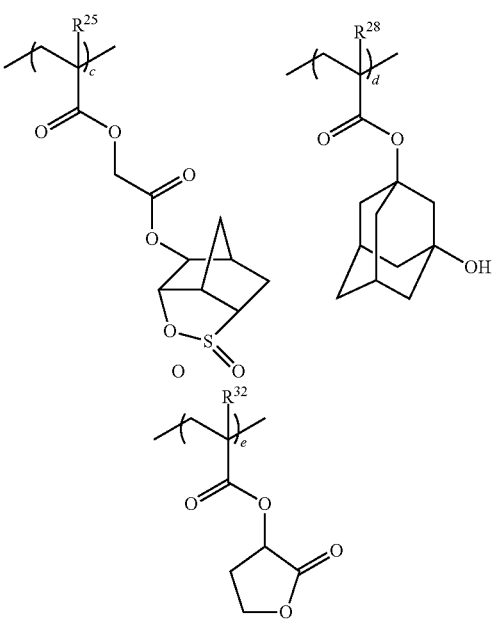
(A)-23
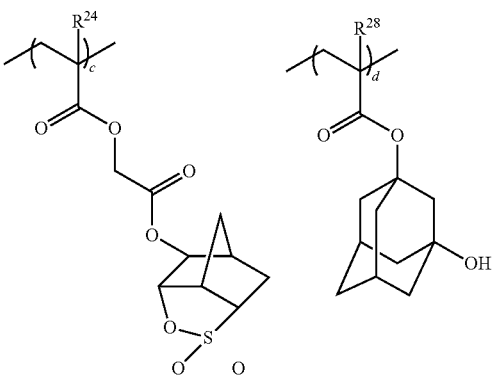

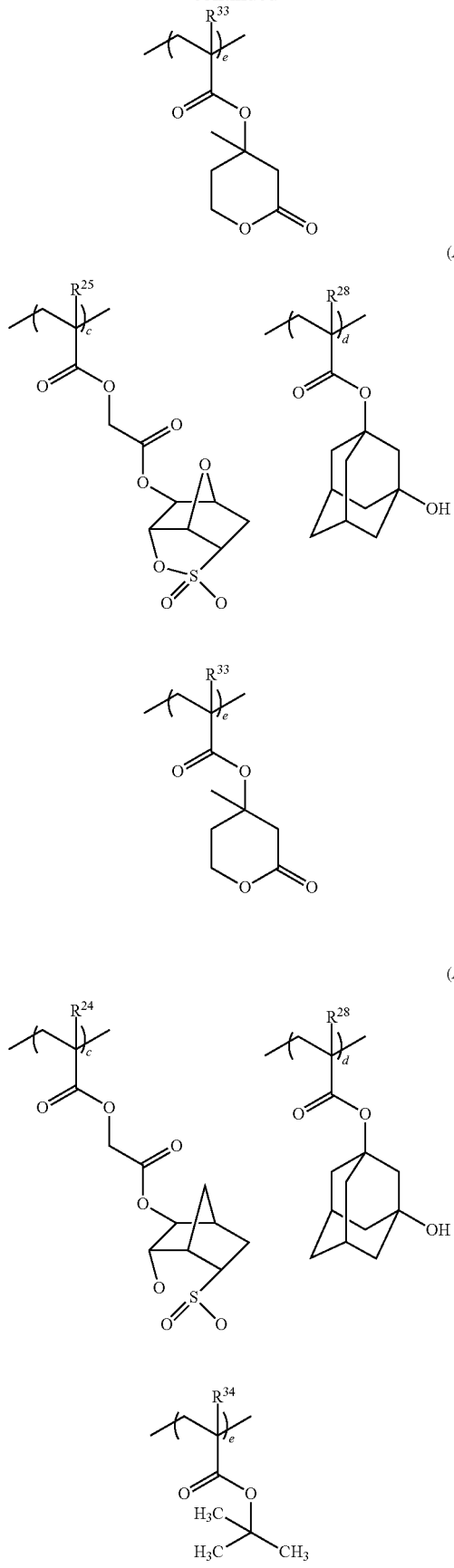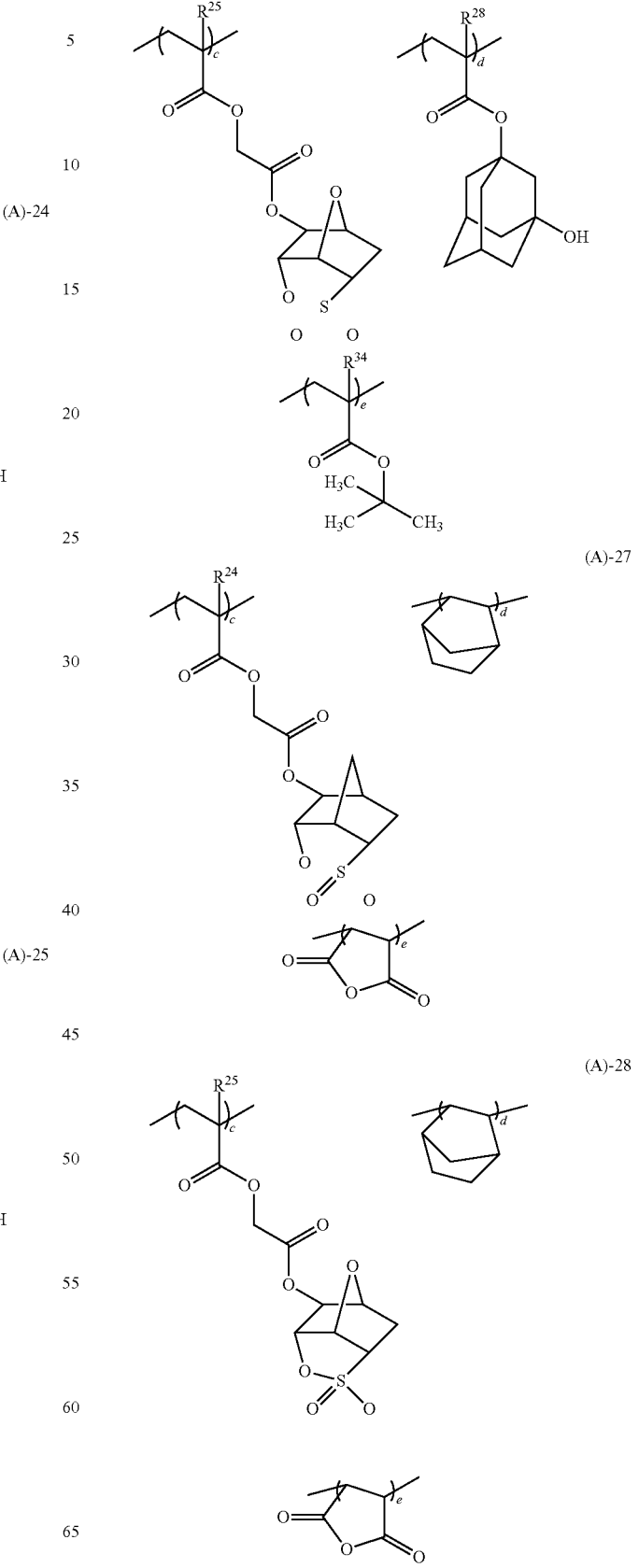

(A)-29
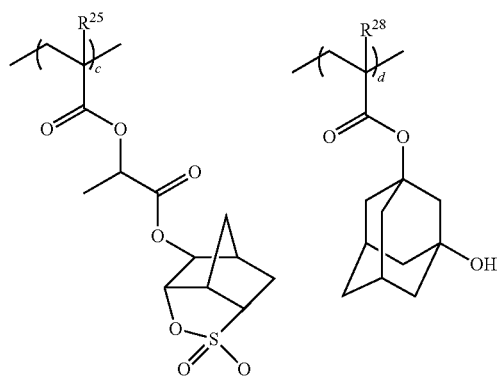
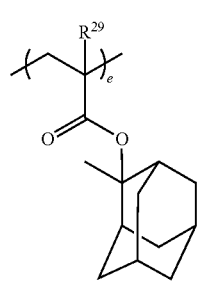
(A)-30
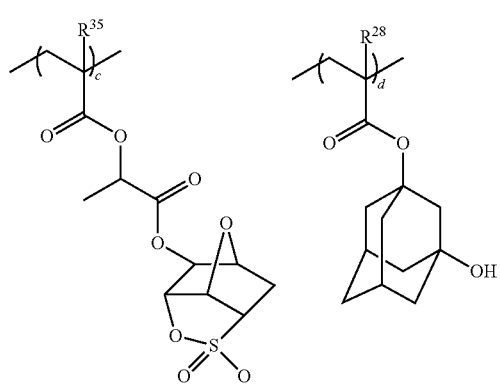
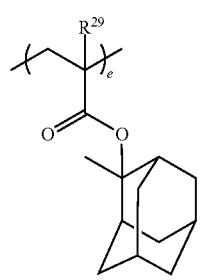
(A)-31
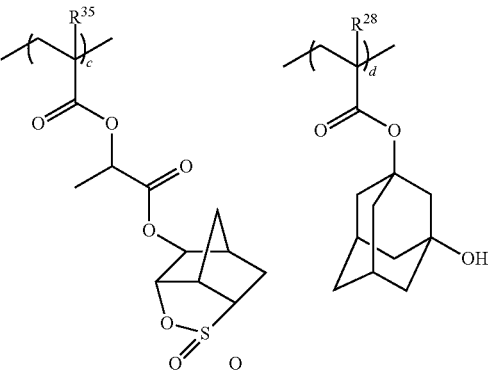
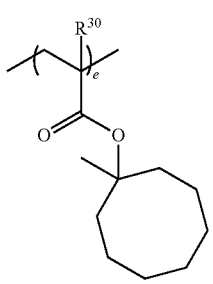
(A)-32

(A)-33
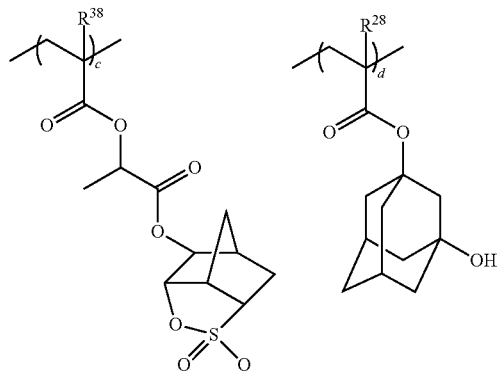
(A)-35
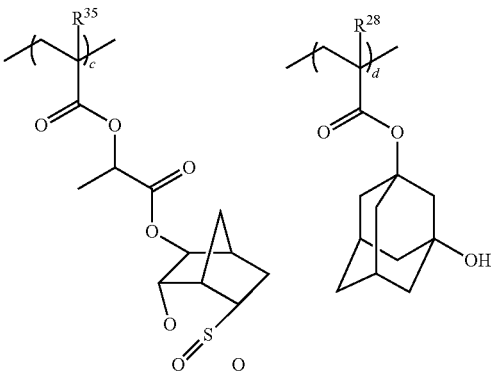
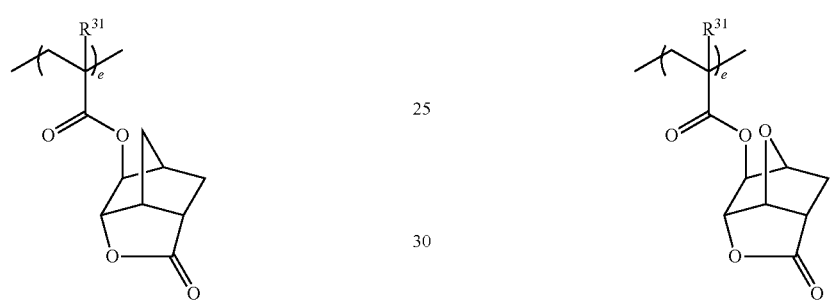
(A)-34
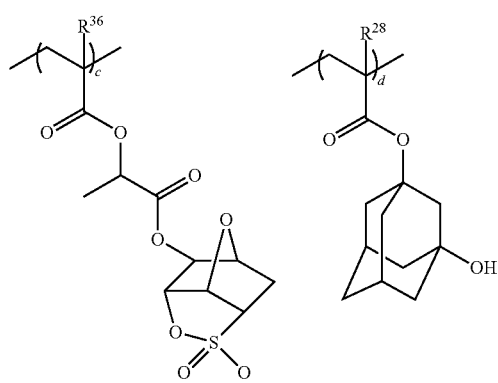
(A)-36
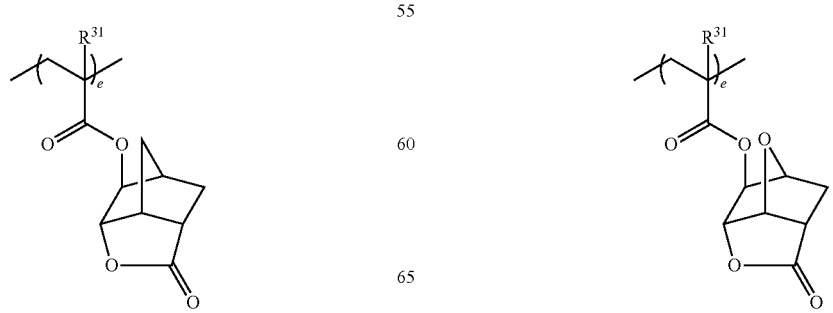

(A)-37
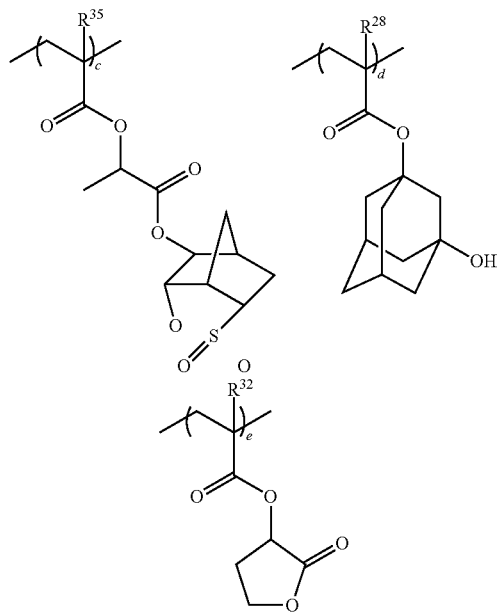
(A)-38
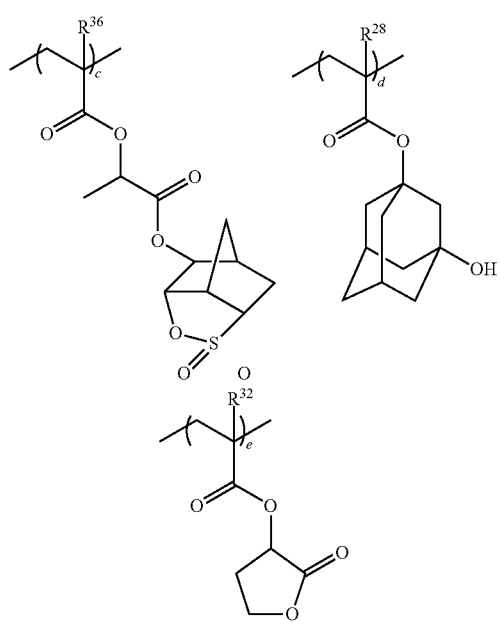
(A)-39
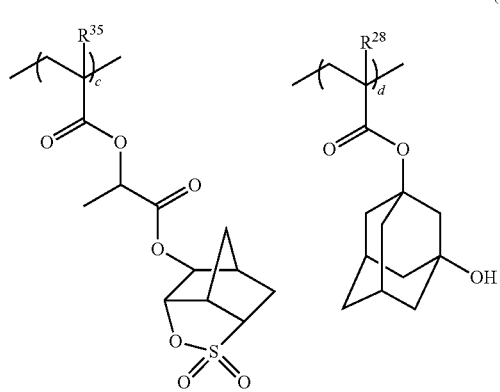
(A)-40
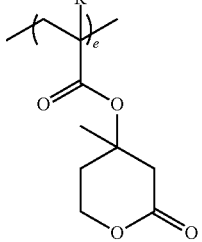
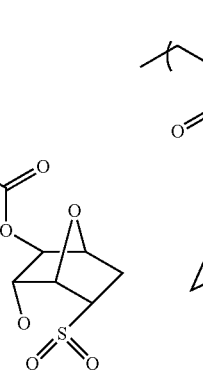
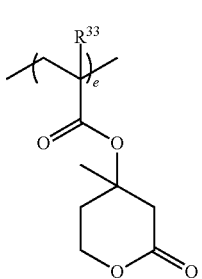
(A)-41
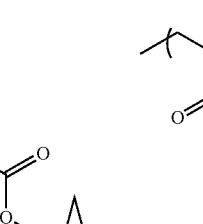
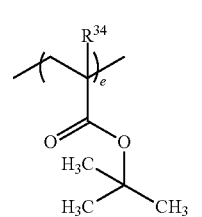

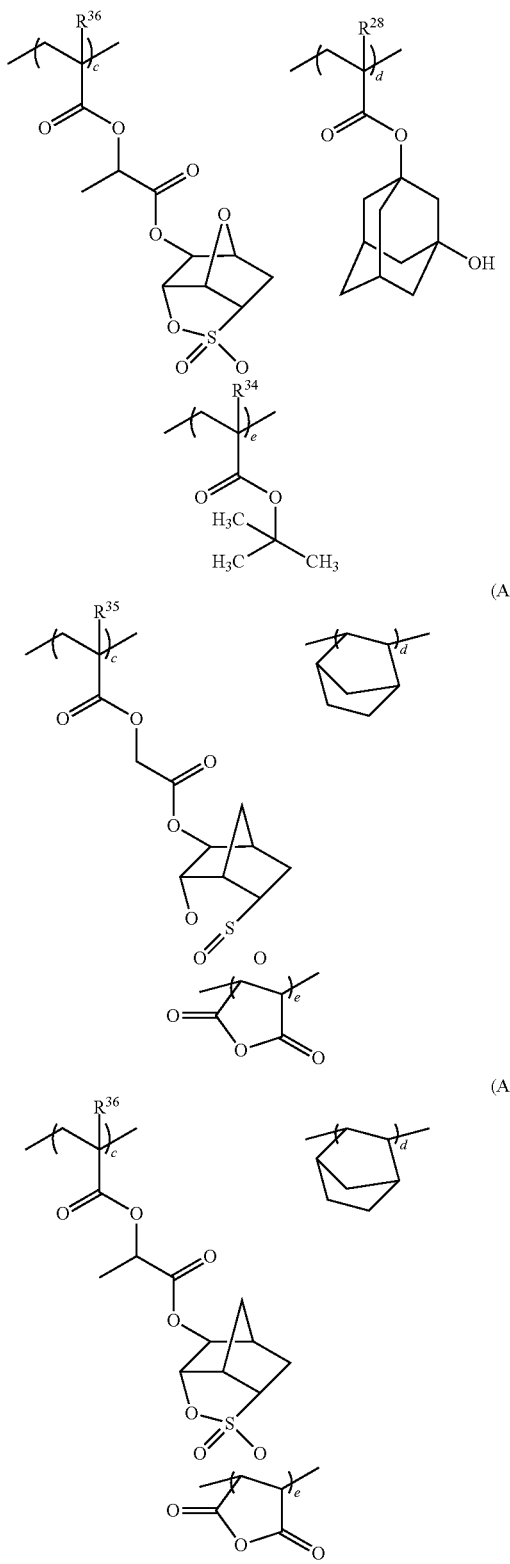

When a weight average molecular weight (Mw) of the polymer compound (A) is not particularly limited, when it is in the range of from 500 to 50,000, and preferably in the range of from 1,000 to 30,000, the resulting polymer compound (A) is useful as a component of a photoresist composition as described later. Such Mw and a number average molecular weight (Mn) are those calculated by the method described in the working examples. Also, a degree of dispersion of molecular weight (Mw/Mn) can be determined by dividing the weight average molecular weight (Mw) by the number average molecular weight (Mn).

[Photoresist Composition]

A photoresist composition is prepared by blending the foregoing polymer compound (A) and an organic solvent and a photo acid generator as described later and optionally, a basic compound and an additive.

Examples of the organic solvent which is blended in the photoresist composition include glycol ethers such as propylene glycol monoethyl ether, propylene glycol monomethyl ether acetate, ethylene glycol monomethyl ether, ethylene glycol monomethyl ether acetate, ethylene glycol monoethyl ether propionate, ethylene glycol monobutyl ether, ethylene glycol monobutyl ether acetate, diethylene glycol dimethyl ether, etc.; esters such as ethyl lactate, methyl 3-methoxypropionate, methyl acetate, ethyl acetate, propyl acetate, etc.; ketones such as acetone, methyl ethyl ketone, methyl isopropyl ketone, methyl isobutyl ketone, methyl amyl ketone, cyclopentanone, cyclohexanone, etc.; ethers such as diethyl ether, diisopropyl ether, dibutyl ether, tetrahydrofuran, 1,4-dioxane, etc.; and so forth. The organic solvent may be used singly or in combinations of two or more kinds thereof.

The organic solvent is preferably a glycol ether, a ketone or an ester; more preferably propylene glycol monomethyl ether acetate, cyclohexanone or ethyl lactate; further preferably a combination of a glycol ether and a ketone; and especially preferably a combination of propylene glycol monomethyl ether acetate and cyclohexanone.

A blending amount of the organic solvent is in general in the range of from 1 to 50 parts by mass, and preferably in the range of from 2 to 25 parts by mass per part by mass of the polymer compound (A).

As the photo acid generator, photo acid generators which have hitherto been usually used for chemical amplification type resists can be used, and examples thereof include nitrobenzyl derivatives such as 2-nitrobenzyl p-toluenesulfonate, 2,6-dinitrobenzyl p-toluenesulfonate, 2,4-dinitrobenzyl p-toluenesulfonate, etc.; sulfonic acid esters such as 1,2,3-tris(methanesulfonyloxy)benzene, 1,2,3-tris(trifluoromethanesulfonyloxy)benzene, 1,2,3-tris(p-toluenesulfonyloxy)benzene, etc.; diazomethane derivatives such as bis(benzenesulfonyl)diazomethane, bis(p-toluenesulfonyl)diazomethane, bis(2,4-dimethylphenylsulfonyl)diazomethane, bis(1,1-dimethylethylsulfonyl)diazomethane, bis(cyclohexylsulfonyl)diazomethane, bis(n-butylsulfonyl)diazomethane, etc.; onium salts such as triphenylsulfonium trifluoromethanesulfonate, triphenylsulfonium nanofluoro-n-butanesulfonate, (p-tert-butoxyphenyl)diphenylsulfonium trifluoromethanesulfonate, tris(p-tert-butoxyphenyl)sulfonium trifluoromethanesulfonate, triphenylsulfonium p-toluenesulfonate, (p-tert-butoxyphenyl)diphenylsulfonium p-toluenesulfonate, tris(p-tert-butoxyphenyl)sulfonium p-toluenesulfonate, trinaphthylsulfonium trifluoromethanesulfonate, cyclohexylmethyl(2-oxocyclohexyl)sulfonium trifluoromethanesulfonate, (2-norbornyl)methyl(2-oxocyclohexyl)sulfonium trilfluoromethanesulfonate, 1,2'-naphthylcarbonylmethyl-tetrahydrothiophenium triflate, etc.; glyoxime derivatives such as bis-O-(p-toluenesulfonyl)-α-dimethylglyoxime, bis-O-(n-butanesulfonyl)-α-dimethylglyoxime, etc.; sulfonic acid ester derivatives of a N-hydroxyimide compound such as N-hydroxysuccinimide methanesulfonic acid ester, N-hydroxysuccinimide trifluoromethanesulfonic acid ester, N-hydroxysuccinimide 1-propanesulfonic acid ester, N-hydroxyimide p-toluenesulfonic acid ester, N-hydroxynaphthalimide methanesulfonic acid ester, N-hydroxynaphthalimide benzenesulfonic acid ester, etc.; halogen-containing triazine compounds such as 2-(4-methoxyphenyl)-4,6-bis(trichloromethyl)-1,3,5-triazine, 2-(4-methoxynaphthyl)-4,6-bis(trichloromethyl)-1,3,5-triazine, 2-[2-(2-furyl)ethenyl]-4,6-bis(trichloromethyl)-1,3,5-triazine, 2-[2-(5-methyl-2-furyl)ethenyl]-4,6-bis(trichloromethyl)-1,3,5-triazine, 2-[2-(3,5-dimethoxyphenyl)ethenyl]-4,6-bis(trichloromethyl)-1,3,5-triazine, etc.; and so forth. Such a photo acid generator may be used singly or in combinations of two or more kinds thereof.

From the viewpoint of ensuring sensitivity and developability of the photoresist composition, in general, a blending amount of the photo acid generator is preferably in the range of from 0.1 to 30 parts by mass, and more preferably in the range of from 0.5 to 10 parts by mass based on 100 parts by mass of the foregoing polymer compound (A).

For the purpose of controlling a diffusion rate of the acid in the photoresist film to enhance the resolution, if desired, the photoresist composition of the present invention can be blended with a basic compound in an amount in the range where the characteristics of the photoresist composition of the present invention are not impaired.

Examples of such a basic compound include amides such as formamide, N-methylformamide, N,N-dimethylformamide, acetamide, N-methylacetamide, N,N-dimethylacetamide, N-(1-adamantyl)acetamide, benzamide, N-acetylethanolamine, 1-acetyl-3-methylpiperidine, pyrrolidone, N-methylpyrrolidone, ε-caprolactam, δ-valerolactam, 2-pyrrolidinone, acrylamide, methacrylamide, t-butyl acrylamide, methylenebisacrylamide, methylenebismethacrylamide, N-methylolacrylamide, N-methoxyacrylamide, diacetone-acrylamide, etc.; and amines such as pyridine, 2-methylpyridine, 4-methylpyridine, nicotine, quinoline, acridine, imidazole, 4-methylimidazole, benzimidazole, pyrazine, pyrazole, pyrrolidine, piperidine, tetrazole, morpholine, 4-methylmorpholine, piperazine, 1,4-diazabicyclo[2.2.2]octane, tributylamine, tripentylamine, trihexylamine, triheptylamine, trioctylamine, triethanolamine, etc. These may be used singly or in combinations of two or more kinds thereof.

In the case of blending the basic compound, though its blending amount varies depending upon the kind of the basic compound to be used, it is in general in the range of from 0.01 to 10 moles, and preferably in the range of from 0.05 to 1 mole per mole of the photo acid generator.

For the purpose of enhancing coating properties, if desired, the photoresist composition of the present invention can be further blended with a surfactant in an amount in the range where the characteristics of the photoresist composition of the present invention are not impaired.

Examples of such a surfactant include polyoxyethylene lauryl ether, polyoxyethylene stearyl ether, polyoxyethylene oleyl ether, polyoxyethylene n-octylphenyl ether and so forth.

The surfactant may be used singly or in combinations of two or more kinds thereof.

In the case of using the surfactant, its use amount is in general not more than 2 parts by mass based on 100 parts by mass of the polymer compound (A).

Furthermore, the photoresist composition of the present invention can be blended with, as other additive, a sensitizer, an anti-halation agent, a shape modifier, a storage stabilizer, a defoaming agent or the like in an amount in the range where the characteristics of the photoresist composition of the present invention are not impaired.

(Photoresist Pattern Formation)

A formation method of a photoresist pattern includes a step of forming a resist film on a support using the foregoing photoresist composition; a step of exposing the foregoing resist film; and a step of developing the foregoing resist film to form a resist pattern.

Specifically, first of all, the foregoing photoresist composition is coated on a support using a spinner or the like; prebaking is carried out for from 1 minute to 10 minutes under a temperature condition of from 70 to 160° C.; this is selectively exposed with a radiation via a desired mask pattern; and post exposure baking is then carried out for from 1 to 5 minutes under a temperature condition of from 70 to 160° C. Subsequently, this is developed with an alkaline developer, for example, a 0.1 to 10% by mass tetramethylammonium hydroxide aqueous solution and preferably subjected to water rinsing using pure water, followed by drying, so that a resist pattern can be formed.

In this connection, an organic or inorganic antireflection film can also be provided between the substrate and the coating layer of the photoresist composition.

Also, a wavelength of the radiation which is used for the exposure is not particularly limited, and the exposure can be carried out using a radiation such as an ArF excimer laser, a KrF excimer laser, an $F_2$ excimer laser, EUV (extreme ultraviolet ray), VUV (vacuum ultraviolet ray), EB (electron beam), an X-ray, a soft X-ray, etc. The photoresist composition according to the present invention is especially effective against an ArF excimer laser. An exposure dose is preferably in the range of from 0.1 to 1,000 mJ/cm$^2$.

Also, the photoresist composition composed of a polymer compound containing the acrylate derivative (1) according to the present invention can be applied to immersion lithography. The immersion lithography as referred to herein is an exposure technology in which a liquid having a higher refractive index of light than the air is injected between a projection lens of an exposure apparatus and the resist film, thereby increasing the resolution.

In the ArF immersion lithography, pure water is used as such a liquid. Specifically, by injecting pure water between the resist film after prebaking and the projection lens and conducting the exposure, in the case of conducting the exposure with an ArF excimer laser having a wavelength of 193 nm, the radiation having passed through the resist film has a wavelength of 135 nm, thereby achieving shortening of the wavelength, so that it becomes possible to obtain a high resolution.

EXAMPLES

The present invention is hereunder described in more detail with reference to the following Examples, but it should be construed that the present invention is not limited to these Examples at all. In this connection, a measurement method of Mw and Mn and a calculation method of a degree of dispersion in each of the Examples are as follows.

(Measurement of Mw and Mn and Calculation of Degree of Dispersion)

A weight average molecular weight (Mw) and a number average molecular weight (Mn) were determined as a values converted according to a calibration curve prepared using standard polystyrene by conducting gel permeation chromatography (GPC) measurement with tetrahydrofuran (THF) as an eluent using a differential refractometer as a detector under the following condition. Also, a degree of dispersion (Mw/Mn) was determined by dividing the weight average molecular weight (Mw) by the number average molecular weight (Mn).

GPC measurement: The measurement was carried out using three connected columns of "TSK-gel supermultipore HZ-M" (a trade name, manufactured by Tosoh Corporation, 4.6 mm×150 mm) connected under a condition at a column temperature of 40° C., a differential refractometer temperature of 40° C. and a flow rate of the eluent of 0.35 mL/min.

Example 1

Production of 2-chloroacetoxy-4,5-oxathiatricyclo[4.2.1.0$^{3,7}$]nonane-5,5-dioxide In a four-necked flask having an internal volume of 200 mL and having a dropping funnel, a thermometer and a stirrer installed therein, 12.0 g (63.1 moles) of 5-hydroxy-3-oxa-2-thiatricyclo[4.2.1.0$^{4,8}$]nonane-2,2-dione and 63 g of tetrahydrofuran were charged, 7.0 g (88.4 moles) of pyridine was subsequently added, and the mixture was stirred at room temperature for 15 minutes.

Subsequently, the obtained mixed solution was cooled to from 0 to 5° C., 9.38 g (97%, 80.6 mmoles) of chloroacetic acid chloride was added dropwise under stirring, and the reaction mixture was stirred at from 5 to 10° C. for 2 hours. To the reaction mixture, 38.0 g of distilled water and 37.3 g of ethyl acetate were added, and the mixture was stirred and then separated into an organic phase and an aqueous phase. The organic phase was successively washed with 37.8 g of an 8% sodium hydrogencarbonate aqueous solution and 37.3 g of distilled water and then concentrated under reduced pressure.

The obtained residue was recrystallized from ethyl acetate/toluene, thereby obtaining 12.9 g (48.4 moles, yield: 76.7%) of 2-chloroacetoxy-4,5-oxathiatricyclo[4.2.1.0]nonane-5,5-dioxide having the following physical properties.

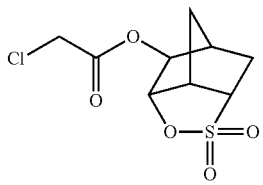 [SMILES: O=C(CCl)OC1C2CC3C1OS(=O)(=O)C3C2]

$^1$H-NMR (300 MHz, CDCl$_3$, TMS, ppm) δ: 4.74 to 4.81 (m, 2H), 4.07 (d, 2H), 3.47 to 3.62 (m, 2H), 2.63 (s, 1H), 2.06 to 2.23 (m, 3H), 1.78 to 1.83 (m, 1H)

Example 2

Production of 2-methacryloyloxyacetoxy-4,5-oxathiatricyclo[4.2.1.0$^{3,7}$]nonane-5,5-dioxide In a four-necked flask having an internal volume of 200 mL and having a stirrer, a thermometer and a reflux condenser installed therein, 12.1 g (45.3 mmoles) of 2-chloroacetoxy-4,5-oxathiatricyclo[4.2.1.0$^{3,7}$]nonane-5,5-dioxide obtained in Example 1, 4.5 mg of phenothiazine, 63.5 g of tetrahydrofuran, 5.00 g (36.2 mmoles) of potassium carbonate and 0.163 g (0.44 mmoles) of tetrabutylammonium iodide were charged, and the mixture was stirred at 40° C. Subsequently, 4.68 g (54.4 mmoles) of methacrylic acid was added at 40° C. under stirring, and the temperature was then increased to 50° C. The reaction mixture was stirred at an internal temperature of 50° C. for 3 hours, followed by cooling to room temperature.

To the reaction mixture, 64.2 g of toluene and 38.1 g of distilled water were added, and the mixture was stirred and then separated into an organic phase and an aqueous phase. The organic phase was washed twice with 38.0 g of distilled water and then concentrated.

The obtained residue was recrystallized from toluene/diisopropyl ether, thereby obtaining 12.3 g (38.7 mmoles, yield: 85.4%) of 2-methacryloyloxyacetoxy-4,5-oxathiatricyclo[4.2.1.0$^{3,7}$]nonane-5,5-dioxide having the following physical properties.

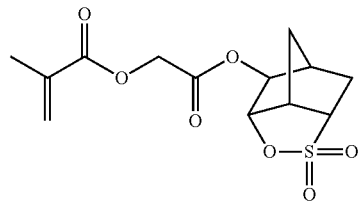 [SMILES: C=C(C)C(=O)OCC(=O)OC1C2CC3C1OS(=O)(=O)C3C2]

$^1$H-NMR (300 MHz, CDCl$_3$, TMS, ppm) δ: 6.21 (s, 1H), 5.67 to 5.68 (m, 1H), 4.71 to 4.80 (m, 2H), 4.66 (d, 2H), 3.47 to 3.56 (m, 2H), 2.61 (s, 1H), 2.00 to 2.17 (m, 3H), 1.97 (s, 3H), 1.76 to 1.80 (m, 1H)

Example 3

Production of 5-chloroacetoxy-3,7-dioxa-2-thiatricyclo[4.2.1.0$^{4,8}$]nonane-2,2-dioxide In a four-necked flask having an internal volume of 200 mL and having a dropping funnel, a thermometer and a stirrer installed therein, 12.1 g (63.1 mmoles) of 5-hydroxy-3,7-dioxa-2-thiatricyclo[4.2.1.0$^{4,8}$]nonane-2,2-dioxide and 63 g of tetrahydrofuran were charged, 7.0 g (88.4 mmoles) of pyridine was subsequently added, and the mixture was stirred at room temperature for 15 minutes.

Subsequently, the obtained mixed solution was cooled to from 0 to 5° C., 9.38 g (97%, 80.6 moles) of chloroacetic acid chloride was added dropwise under stirring, and the reaction mixture was stirred at from 5 to 10° C. for 2 hours. To the reaction mixture, 38.0 g of distilled water and 37.3 g of ethyl acetate were added, and the mixture was stirred and then separated into an organic phase and an aqueous phase. The organic phase was successively washed with 37.8 g of an 8% sodium hydrogencarbonate aqueous solution and 37.3 g of distilled water and then concentrated under reduced pressure.

The obtained residue was recrystallized from ethyl acetate/toluene, thereby obtaining 13.4 g (49.9 mmoles, yield: 79.0%) of 5-chloroacetoxy-3,7-dioxa-2-thiatricyclo[4.2.1.0$^{4,8}$]nonane-2,2-dioxide having the following physical properties.

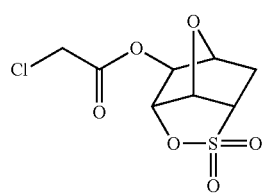 [SMILES: O=C(CCl)OC1C2CC3C(O2)C1OS3(=O)=O]

$^1$H-NMR (400 MHz, CDCl$_3$, TMS, ppm) δ: 5.84 (dd, J=4.8, 1.2 Hz, 1H), 5.75 (dd, J=4.8, 4.8 Hz, 1H), 4.80 to 4.84 (m, 1H), 4.14 (s, 1H), 4.07 (s, 2H), 3.87 to 3.92 (m, 1H), 2.44 to 2.47 (m, 2H)

Example 4

Production of 5-methacryloyloxyacetoxy-3,7-dioxa-2-thiatricyclo[4.2.1.0$^{4,8}$]nonane-2,2-dioxide In a four-necked flask having an internal volume of 200 mL and having a stirrer, a thermometer and a reflux condenser installed therein, 12.2 g (45.3 mmoles) of 5-chloroacetoxy-3,7-dioxa-2-thiatricyclo[4.2.1.0$^{4,8}$]nonane-2,2-dioxide obtained in Example 3, 4.5 mg of phenothiazine, 63.5 g of tetrahydrofuran, 5.00 g (36.2 moles) of potassium carbonate and 0.163 g (0.44 mmoles) of tetrabutylammonium iodide were charged, and the mixture was stirred at 40° C. Subsequently, 4.68 g (54.4 mmoles) of methacrylic acid was added at 40° C. under stirring, and the temperature was then increased to 50° C. The reaction mixture was stirred at an internal temperature of 50° C. for 3 hours, followed by cooling to room temperature.

To the reaction mixture, 64.2 g of ethyl acetate and 38.1 g of distilled water were added, and the mixture was stirred and then separated into an organic phase and an aqueous phase. The organic phase was washed twice with 38.0 g of distilled water and then concentrated.

The obtained residue was recrystallized from ethyl acetate/diisopropyl ether, thereby obtaining 12.8 g (40.2 mmoles, yield: 88.8%) of 5-methacryloyloxyacetoxy-3,7-dioxa-2-thiatricyclo[4.2.1.0"]nonane-2,2-dioxide having the following physical properties.

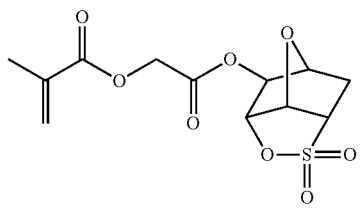 [SMILES: C=C(C)C(=O)OCC(=O)OC1C2CC3C(O2)C1OS3(=O)=O]

$^1$H-NMR (400 MHz, CDCl$_3$, TMS, ppm) δ: 6.21 (s, 1H), 5.67 to 5.68 (m, 1H), 5.83 (dd, J=4.8, 1.2 Hz, 1H), 5.72 (dd, J=4.8, 4.8 Hz, 1H), 4.78 to 4.82 (m, 1H), 4.12 (s, 1H), 4.69 (s, 2H), 3.85 to 3.92 (m, 1H), 2.44 to 2.45 (m, 2H), 1.97 (s, 3H)

Example 5

Production of Polymer Compound a

In a three-necked flask having an internal volume of 50 mL and having an electromagnetic stirrer, a reflux condenser and a thermometer, 2.34 g (10 mmoles) of 2-methacryloyloxy-2-methyladamantane, 3.15 g (10 moles) of 2-methacryloyloxy-acetoxy-4,5-oxathiatricyclo[4.2.1.0$^{3,7}$]nonane-5,5-dioxide obtained in Example 2 and 22.6 g of methyl ethyl ketone were charged, and the mixture was subjected to bubbling with nitrogen for 10 minutes. Furthermore, 0.23 g (1.4 mmoles) of 2,2'-azobisisobutyronitrile was charged in a nitrogen atmosphere, and the mixture was subjected to a polymerization reaction at from 78 to 80° C. for 5 hours.

The obtained reaction mixture solution was added dropwise to methanol in an amount of about 20 times by mass the reaction mixture solution at room temperature while stirring, and a formed precipitate was collected by filtration. The subject precipitate was dried under reduced pressure (26.7 Pa) at 50° C. for 5 hours, thereby obtaining 3.48 g of a polymer compound composed of the following repeating units (hereinafter referred to as "Polymer Compound a"). The obtained Polymer Compound a had a weight average molecular weight (Mw) of 6,800 and a degree of dispersion of 1.67.

Polymer Compound a

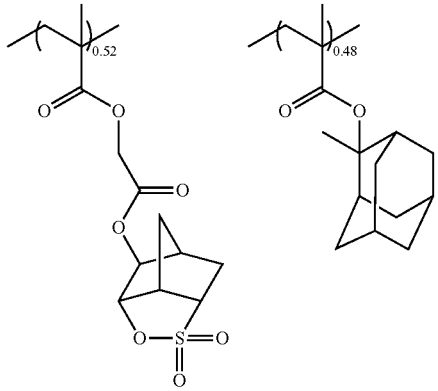

Example 6

Production of Polymer Compound a'

The experiment was carried out in the same manner as in Example 5, except that in Example 5, 3.18 g (10 mmoles) of 5-methacryloyloxyacetoxy-3,7-dioxa-2-thiatricyclo[4.2.1.0$^{4,8}$]nonane-2,2-dioxide obtained in Example 4 was used in place of 3.15 g (10 mmoles) of 2-methacryloyloxy-acetoxy-4,5-oxathiatricyclo[4.2.1.0$^{3,7}$]nonane-5,5-dioxide, thereby obtaining 3.55 g of a polymer compound composed of the following repeating units (hereinafter referred to as "Polymer Compound a'"). The obtained Polymer Compound a' had a mass average molecular weight (Mw) of 7,000 and a degree of dispersion of 1.66.

Polymer Compound a'

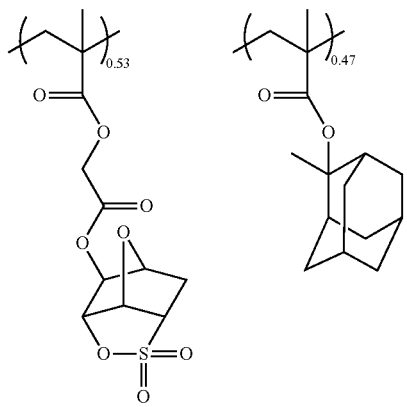

Comparative Synthesis Example 1

Synthesis of Polymer Compound b

In a three-necked flask having an internal volume of 50 mL and having an electromagnetic stirrer, a reflux condenser and a thermometer, 2.40 g (10 mmoles) of 2-methacryloyloxy-2-methyladamantane, 2.82 g (10 mmoles) of 2-methacryloy-loxyacetoxy-2-oxo-4-oxahexahydro-3,5-methano-2H-cyclopenta[b]furan-6-yl and 25.4 g of methyl ethyl ketone were charged, and the mixture was subjected to bubbling with nitrogen for 10 minutes. Furthermore, 0.24 g (1.4 mmoles) of 2,2'-azobisisobutyronitrile was charged in a nitrogen atmosphere, and the mixture was subjected to a polymerization reaction at from 79 to 81° C. for 5 hours.

The obtained reaction mixture solution was added dropwise to methanol in an amount of about 20 times by mass at room temperature while stirring, thereby obtaining a white precipitate. The subject precipitate was dried under reduced pressure (26.7 Pa) at 50° C. for 5 hours, thereby obtaining 2.91 g of a polymer compound composed of the following repeating units (hereinafter referred to as "Polymer Compound b"). The obtained Polymer Compound b had a mass average molecular weight (Mw) of 5,800 and a degree of dispersion of 1.61.

Polymer Compound b

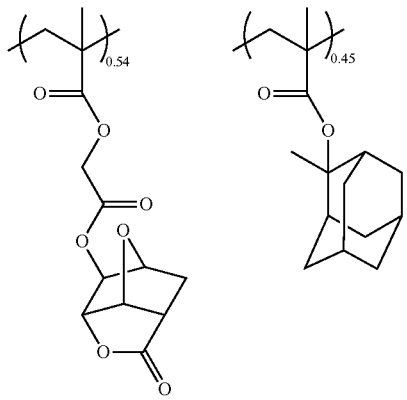

Example 7

Evaluation of Solubility

A solubility of 2-methacryloyloxyacetoxy-4,5-oxathiatricyclo[4.2.1.0$^{3,7}$]nonane-5,5-dioxide obtained in Example 2 in tetrahydrofuran was measured according to the following operation. The results are shown in Table 1.

(Measurement Method of Solubility)

1 g of a sample to be used for the evaluation of solubility was prepared. 1 g of an organic solvent described in Table 1 and the foregoing sample were mixed at 25° C., and the mixture was stirred at 25° C. for 10 minutes as it was. An insoluble matter was filtered out from the obtained mixed solution, and the organic solvent was distilled off from the filtrate. Subsequently, the residue was dried under reduced pressure for 5 hours, thereby obtaining the sample in the saturated solution. A mass of the subject sample was measured, and its solubility was calculated according to the following expression.

Solubility(% by mass)=100×(Mass of the sample in the saturated solution)/(Mass of the saturated solution)

Examples 8 to 16 and Comparative Examples 1 to 5

Evaluation of Solubility

The experiment and evaluation of solubility were carried out in the same manner as in Example 7, except that in Example 7, the sample and the organic solvent were changed to those shown in Table 1 or Table 2. The results are shown in Table 1 or Table 2.

TABLE 1

| Evaluation of solubility at 25° C. | | | |
|---|---|---|---|
| | Sample | Organic solvent | Solubility (% by mass) |
| Example 7 | (structure) | Tetrahydrofuran | 48.1 |
| Example 8 | (structure) | Tetrahydrofuran | 31.9 |
| Comparative Example 1 | (structure) | Tetrahydrofuran | 7.8 |

TABLE 1-continued

Evaluation of solubility at 25° C.

| Sample | | Organic solvent | Solubility (% by mass) |
|---|---|---|---|
| Example 9 | (structure) | Methyl ethyl ketone | 45.5 |
| Example 10 | (structure) | Methyl ethyl ketone | 30.8 |
| Comparative Example 2 | (structure) | Methyl ethyl ketone | 4.2 |

TABLE 2

Evaluation of solubility at 25° C.

| Sample | | Organic solvent | Solubility (% by mass) |
|---|---|---|---|
| Example 11 | Polymer Compound a | Propylene glycol monomethyl ether acetate/cyclohexanone (mass ratio: 1/1) | 17.8 |
| Example 12 | Polymer Compound a' | Propylene glycol monomethyl ether acetate/cyclohexanone (mass ratio: 1/1) | 12.2 |
| Comparative Example 3 | Polymer Compound b | Propylene glycol monomethyl ether acetate/cyclohexanone (mass ratio: 1/1) | 5.8 |
| Example 13 | Polymer Compound a | Cyclohexanone | 12.6 |
| Example 14 | Polymer Compound a' | Cyclohexanone | 8.8 |
| Comparative Example 4 | Polymer Compound b | Cyclohexanone | 2.3 |
| Example 15 | Polymer Compound a | Ethyl lactate | 15.0 |
| Example 16 | Polymer Compound a' | Ethyl lactate | 9.8 |
| Comparative Example 5 | Polymer Compound b | Ethyl lactate | 3.6 |

Example 17

Exposure Evaluation by Double Beam Interference Method 100 parts by mass of Polymer Compound a obtained in Example 5, 3 parts by mass of "TPS-109" (a trade name, component: triphenylsulfonium nanofluoro-n-butane-sulfonate, manufactured by Midori Kagaku Co., Ltd.) as a photo acid generator and an organic solvent [a mixed solvent of propylene glycol monomethyl ether acetate/cyclohexanone (mass ratio: 1/1)] were mixed to prepare a photoresist composition having a concentration of Polymer Compound a of 10% by mass. This photoresist composition was filtered using a filter [made of a tetrafluoroethylene resin (PTFE), pore size: 0.2 μm], thereby obtaining a filtrate.

A propylene glycol monomethyl ether acetate solution of a cresol type novolak resin "PS-6937" (a trade name, manufactured by Gunei Chemical Industry Co., Ltd.) in a concentration of 6% by mass was coated on a silicon wafer having a diameter of 10 cm by a spin coating method and baked on a hot plate at 200° C. for 90 seconds to form an antireflection film (base film) having a film thickness of about 100 nm. The foregoing filtrate was coated on this antireflection film by a spin coating method and prebaked on a hot plate at 130° C. for 90 seconds, thereby forming a resist film having a film thickness of about 300 nm.

This resist film was exposed with an ArF excimer laser having a wavelength of 193 nm by a double beam interference method.

Subsequently, the exposed resist film was post-exposure baked at 130° C. for 90 seconds and then developed with a 2.38% by mass tetramethylammonium hydroxide aqueous solution for 60 seconds, thereby forming a 1:1 line-and-space pattern.

The developed wafer was cut and observed by a scanning electron microscope (SEM). As a result, resolution of a 1:1 line-and-space resist pattern having a line width of 100 nm was confirmed at an optimal exposure dose.

Example 18

Exposure Evaluation by Double Beam Interference Method 100 parts by mass of Polymer Compound a' obtained in Example 6, 3 parts by mass of "TPS-109" (a trade name, component: triphenylsulfonium nanofluoro-n-butane-sulfonate, manufactured by Midori Kagaku Co., Ltd.) as a photo acid generator and an organic solvent [a mixed solvent of propylene glycol monomethyl ether acetate/cyclohexanone (mass ratio: 1/1)] were mixed to prepare a photoresist composition having a concentration of Polymer Compound a' of 10% by mass. This photoresist composition was filtered using a filter [made of a tetrafluoroethylene resin (PTFE), pore size: 0.2 μm], thereby obtaining a filtrate.

A propylene glycol monomethyl ether acetate solution of a cresol type novolak resin "PS-6937" (a trade name, manufactured by Gun Ei Chemical Industry Co., Ltd.) in a concentration of 6% by mass was coated on a silicon wafer having a diameter of 10 cm by a spin coating method and baked on a hot plate at 200° C. for 90 seconds to form an antireflection film (base film) having a film thickness of about 100 nm. The foregoing filtrate was coated on this antireflection film by a spin coating method and prebaked on a hot plate at 130° C. for 90 seconds, thereby forming a resist film having a film thickness of about 300 nm.

This resist film was exposed with an ArF excimer laser having a wavelength of 193 nm by a double beam interference method.

Subsequently, the exposed resist film was post-exposure baked at 130° C. for 90 seconds and then developed with a 2.38% by mass tetramethylammonium hydroxide aqueous solution for 60 seconds, thereby forming a 1:1 line-and-space pattern.

The developed wafer was cut and observed by a scanning electron microscope (SEM). As a result, resolution of a 1:1 line-and-space resist pattern having a line width of 100 nm was confirmed at an optimal exposure dose.

INDUSTRIAL APPLICABILITY

The acrylate derivative obtained by the present invention is useful as a raw material of a polymer compound to be blended in a photoresist composition.

The invention claimed is:

1. A method for producing an acrylate derivative of formula (1):

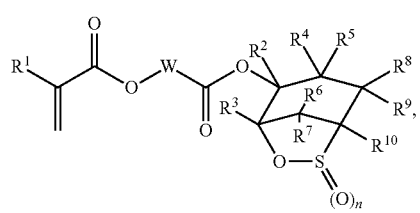

(1)

wherein:
$R^1$ represents a hydrogen atom, a methyl group, or a trifluoromethyl group;
each of $R^2$, $R^3$, $R^5$, $R^7$, $R^8$, $R^9$, and $R^{10}$ independently represents a hydrogen atom, an alkyl group having from 1 to 6 carbon atoms, a cycloalkyl group having from 3 to 6 carbon atoms, or an alkoxy group having from 1 to 6 carbon atoms;

each of $R^4$ and $R^6$ independently represents a hydrogen atom, an alkyl group having from 1 to 6 carbon atoms, a cycloalkyl group having from 3 to 6 carbon atoms or an alkoxy group having from 1 to 6 carbon atoms, or $R^4$ and $R^6$ are bonded to each other to represent an alkylene group having from 1 to 3 carbon atoms, —O—, or —S—;

n represents 0, 1, or 2; and

W represents an alkylene group having from 1 to 10 carbon atoms or a cycloalkylene group having from 5 to 10 carbon atoms, the method comprising:

(A) reacting an alcohol of formula (2):

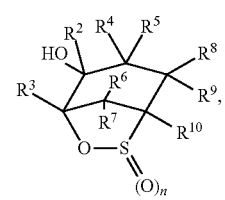

(2)

and a halocarboxylic acid halide of formula (3):

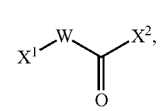

(3)

wherein each of $X^1$ and $X^2$ independently represents a chlorine atom, a bromine atom, or an iodine atom, with each other in the presence of a basic substance, to obtain a haloester derivative of formula (4):

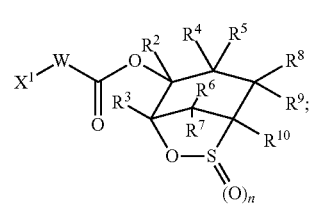

(4)

and (B) reacting the haloester derivative (4) with an acrylic acid based compound of formula (5):

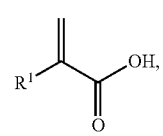

(5)

in the presence of a basic substance.

2. The method of claim 1, wherein in formula (1):
$R^1$ is a hydrogen atom or a methyl group;
W is a methylene group or an ethane-1,1-diyl group;
n is 2;
all of $R^2$, $R^3$, $R^5$, $R^7$, $R^8$, $R^9$, and $R^{10}$ are a hydrogen atom; and
$R^4$ and $R^6$ are bonded to each other to form a methylene group or —O—.

3. A method for producing an acrylate derivative of formula (1):

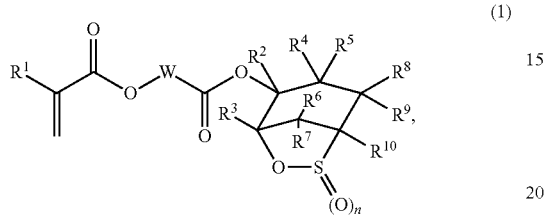

(1)

wherein:
$R^1$ represents a hydrogen atom, a methyl group, or a trifluoromethyl group;
each of $R^2$, $R^3$, $R^5$, $R^7$, $R^8$, $R^9$, and $R^{10}$ independently represents a hydrogen atom, an alkyl group having from 1 to 6 carbon atoms, a cycloalkyl group having from 3 to 6 carbon atoms, or an alkoxy group having from 1 to 6 carbon atoms;
each of $R^4$ and $R^6$ independently represents a hydrogen atom, an alkyl group having from 1 to 6 carbon atoms, a cycloalkyl group having from 3 to 6 carbon atoms or an alkoxy group having from 1 to 6 carbon atoms, or $R^4$ and $R^6$ are bonded to each other to represent an alkylene group having from 1 to 3 carbon atoms, —O—, or —S—;
n represents 0, 1, or 2; and
W represents an alkylene group having from 1 to 10 carbon atoms or a cycloalkylene group having from 5 to 10 carbon atoms,
the method comprising:
reacting a haloester derivative of formula (4):

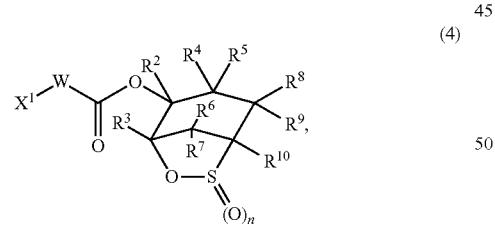

(4)

wherein $X^1$ is a chlorine atom, a bromine atom, or an iodine atom,
with an acrylic acid based compound of formula (5):

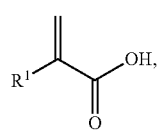

(5)

in the presence of a basic substance.

4. The method of claim 3, wherein in formula (1):
$R^1$ is a hydrogen atom or a methyl group;
W is a methylene group or an ethane-1,1-diyl group;
n is 2;
all of $R^2$, $R^3$, $R^5$, $R^7$, $R^8$, $R^9$, and $R^{10}$ are a hydrogen atom; and
$R^4$ and $R^6$ are bonded to each other to form a methylene group or —O—.

5. A method for producing a haloester derivative of formula (4):

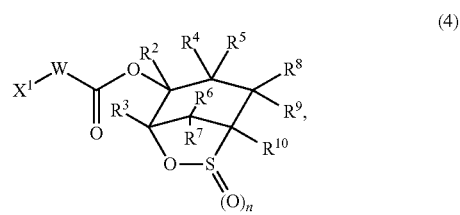

(4)

wherein:
$R^1$ represents a hydrogen atom, a methyl group, or a trifluoromethyl group;
each of $R^2$, $R^3$, $R^5$, $R^7$, $R^8$, $R^9$, and $R^{10}$ independently represents a hydrogen atom, an alkyl group having from 1 to 6 carbon atoms, a cycloalkyl group having from 3 to 6 carbon atoms, or an alkoxy group having from 1 to 6 carbon atoms;
each of $R^4$ and $R^6$ independently represents a hydrogen atom, an alkyl group having from 1 to 6 carbon atoms, a cycloalkyl group having from 3 to 6 carbon atoms or an alkoxy group having from 1 to 6 carbon atoms, or $R^4$ and $R^6$ are bonded to each other to represent an alkylene group having from 1 to 3 carbon atoms, —O—, or —S—;
n represents 0, 1, or 2;
$X^1$ is a chlorine atom, a bromine atom, or an iodine atom; and
W represents an alkylene group having from 1 to 10 carbon atoms or a cycloalkylene group having from 5 to 10 carbon atoms,
the method comprising:
reacting an alcohol of formula (2):

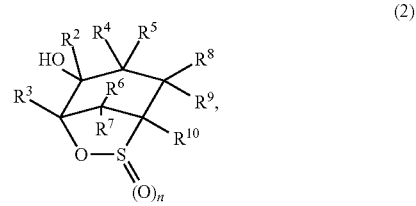

(2)

and a halocarboxylic acid halide of formula (3):

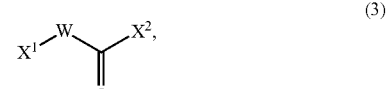

(3)

wherein $X^2$ independently represents a chlorine atom, a bromine atom, or an iodine atom,
with each other in the presence of a basic substance.

6. The method of claim 5, wherein in formula (4),
$X^1$ is a chlorine atom or a bromine atom;
W is a methylene group or an ethane-1,1-diyl group;
n is 2;
all of $R^2$, $R^3$, $R^5$, $R^7$, $R^8$, $R^9$, and $R^{10}$ are a hydrogen atom; and
$R^4$ and $R^6$ are bonded to each other to form a methylene group or —O—.

7. An acrylate derivative of formula (1):

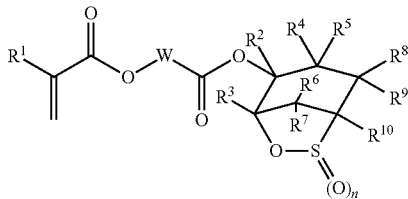

(1)

wherein:
$R^1$ represents a hydrogen atom, a methyl group, or a trifluoromethyl group;
each of $R^2$, $R^3$, $R^5$, $R^7$, $R^8$, $R^9$, and $R^{10}$ independently represents a hydrogen atom, an alkyl group having from 1 to 6 carbon atoms, a cycloalkyl group having from 3 to 6 carbon atoms, or an alkoxy group having from 1 to 6 carbon atoms;
each of $R^4$ and $R^6$ independently represents a hydrogen atom, an alkyl group having from 1 to 6 carbon atoms, a cycloalkyl group having from 3 to 6 carbon atoms or an alkoxy group having from 1 to 6 carbon atoms, or $R^4$ and $R^6$ are bonded to each other to represent an alkylene group having from 1 to 3 carbon atoms, —O—, or —S—;
n represents 0, 1, or 2; and
W represents an alkylene group having from 1 to 10 carbon atoms or a cycloalkylene group having from 5 to 10 carbon atoms.

8. The acrylate derivative according to claim 7, wherein in formula (1):
$R^1$ is a hydrogen atom or a methyl group;
W is a methylene group or an ethane-1,1-diyl group;
n is 2;
all of $R^2$, $R^3$, $R^5$, $R^7$, $R^8$, $R^9$, and $R^{10}$ are a hydrogen atom; and
$R^4$ and $R^6$ are bonded to each other to form a methylene group or —O—.

9. A polymer compound, obtained by a process comprising polymerizing a raw material comprising the acrylate derivative according to claim 8.

10. A photoresist composition, comprising the polymer compound of claim 9, an organic solvent and a photo acid generator.

11. The acrylate derivative of claim 8, wherein in formula (1):
W is a methylene group.

12. The acrylate derivative of claim 8, wherein in formula (1):
W is an ethane-1,1-diyl group.

13. The acrylate derivative of claim 8, wherein in formula (1):
$R^1$ is a methyl group.

14. The acrylate derivative of claim 8, wherein in formula (1):
$R^1$ is a hydrogen atom.

15. The acrylate derivative of claim 8, wherein in formula (1):
$R^4$ and $R^6$ are bonded to each other to form a methylene group.

16. The acrylate derivative of claim 8, wherein in formula (1):
$R^4$ and $R^6$ are bonded to each other to form —O—.

17. A polymer compound obtained by a process comprising polymerizing a raw material comprising the acrylate derivative according to claim 7.

18. A photoresist composition, comprising the polymer compound of claim 17, an organic solvent and a photo acid generator.

19. A haloester derivative of formula (4):

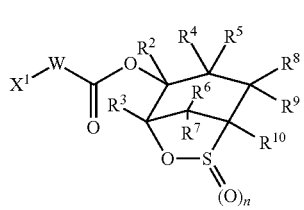

(4)

wherein:
$R^1$ represents a hydrogen atom, a methyl group, or a trifluoromethyl group;
each of $R^2$, $R^3$, $R^5$, $R^7$, $R^8$, $R^9$, and $R^{10}$ independently represents a hydrogen atom, an alkyl group having from 1 to 6 carbon atoms, a cycloalkyl group having from 3 to 6 carbon atoms, or an alkoxy group having from 1 to 6 carbon atoms;
each of $R^4$ and $R^6$ independently represents a hydrogen atom, an alkyl group having from 1 to 6 carbon atoms, a cycloalkyl group having from 3 to 6 carbon atoms or an alkoxy group having from 1 to 6 carbon atoms, or $R^4$ and $R^6$ are bonded to each other to represent an alkylene group having from 1 to 3 carbon atoms, —O—, or —S—;
n represents 0, 1, or 2;
$X^1$ is a chlorine atom, a bromine atom, or an iodine atom; and
W represents an alkylene group having from 1 to 10 carbon atoms or a cycloalkylene group having from 5 to 10 carbon atoms.

20. The haloester derivative according to claim 19, wherein in formula (4),
$X^1$ is a chlorine atom or a bromine atom;
W is a methylene group or an ethane-1,1-diyl group;
n is 2;
all of $R^2$, $R^3$, $R^5$, $R^7$, $R^8$, $R^9$, and $R^{10}$ are a hydrogen atom; and
$R^4$ and $R^6$ are bonded to each other to form a methylene group or —O—.

* * * * *